US012806008B2

(12) United States Patent
Salim

(10) Patent No.: US 12,806,008 B2
(45) Date of Patent: Nov. 24, 2026

(54) METHOD FOR REDUCING PROFILE OF A VASCULAR PROSTHESIS

(71) Applicant: MIRus LLC, Marietta, GA (US)

(72) Inventor: Md Tausif Salim, Decatur, GA (US)

(73) Assignee: MiRus LLC, Marietta, GA (US)

( * ) Notice: Subject to any disclaimer, the term of this patent is extended or adjusted under 35 U.S.C. 154(b) by 358 days.

(21) Appl. No.: 18/663,990

(22) Filed: May 14, 2024

(65) Prior Publication Data

US 2025/0041088 A1 Feb. 6, 2025

Related U.S. Application Data

(60) Provisional application No. 63/530,610, filed on Aug. 3, 2023.

(51) Int. Cl.

| | |
|---|---|
| ***A61F 2/24*** | (2006.01) |
| ***A61F 2/95*** | (2013.01) |
| ***B23P 11/00*** | (2006.01) |

(52) U.S. Cl.

CPC .......... *A61F 2/2412* (2013.01); *A61F 2/2418* (2013.01); *A61F 2/2427* (2013.01); *A61F 2/9524* (2020.05); *B23P 11/005* (2013.01); *A61F 2230/0006* (2013.01); *A61F 2230/0008* (2013.01)

(58) Field of Classification Search

CPC .... A61F 2/2418; A61F 2/2427; A61F 2/2436; A61F 2/2439; A61F 2/9522; A61F 2/9525; A61F 2/2433; A61F 2/243; A61F 2/2466; A61F 2/95; A61F 2/9517; A61F 2/958; A61F 2002/9505; A61F 2/966

See application file for complete search history.

(56) References Cited

U.S. PATENT DOCUMENTS

| | | | | |
|---|---|---|---|---|
| 5,411,522 | A | 5/1995 | Trott | |
| 6,730,118 | B2 | 5/2004 | Spenser et al. | |
| 7,749,266 | B2 * | 7/2010 | Forster .................. | A61F 2/2433 623/2.11 |
| 10,729,543 | B2 | 8/2020 | Levi et al. | |
| 10,820,993 | B2 | 11/2020 | Tabor et al. | |
| 10,856,970 | B2 | 12/2020 | Tuval et al. | |
| 10,869,761 | B2 | 12/2020 | Creaven et al. | |
| 10,952,852 | B2 | 3/2021 | Barbarino et al. | |
| 10,980,632 | B2 | 4/2021 | Burriesci et al. | |
| 10,980,633 | B2 | 4/2021 | Dienno et al. | |
| 2014/0088680 | A1 * | 3/2014 | Costello ................ | A61F 2/2436 623/1.2 |
| 2015/0336150 | A1 * | 11/2015 | Peterson ............... | A61F 2/2418 72/429 |
| 2016/0302921 | A1 * | 10/2016 | Gosal .................... | A61F 2/2418 |
| 2020/0405482 | A1 | 12/2020 | Hariton et al. | |

(Continued)

FOREIGN PATENT DOCUMENTS

| | | | |
|---|---|---|---|
| WO | 2023238006 | A2 | 12/2023 |

OTHER PUBLICATIONS

Kim, Harry; International Search Report and Written Opinion of the International Searching Authority issued in International Application No. PCT/US2025/041017; mailed Dec. 23, 2025; 18 pages.

*Primary Examiner* — Seema Mathew

(74) *Attorney, Agent, or Firm* — UB Greensfelder LLP; Brian E. Turung

(57) ABSTRACT

A method of crimping a prosthetic heart valve.

59 Claims, 18 Drawing Sheets

(56) References Cited

U.S. PATENT DOCUMENTS

| | | | | |
|---|---|---|---|---|
| 2021/0228343 | A1 | 7/2021 | Scheinblum et al. | |
| 2022/0273476 | A1* | 9/2022 | Ung | A61F 2/9522 |
| 2023/0139876 | A1* | 5/2023 | Bowe | A61F 2/2418 623/2.11 |
| 2024/0366371 | A1* | 11/2024 | Bukin | A61F 2/243 |
| 2025/0041052 | A1 | 2/2025 | Salim et al. | |
| 2025/0041088 | A1* | 2/2025 | Salim | A61F 2/2412 |
| 2025/0127615 | A1* | 4/2025 | Okafor | A61F 2/2436 |
| 2025/0143878 | A1* | 5/2025 | Johnson | A61F 2/2436 |
| 2025/0248833 | A1* | 8/2025 | Qureshi | A61M 25/104 |
| 2025/0312177 | A1* | 10/2025 | Murad | A61F 2/9524 |
| 2025/0332012 | A1* | 10/2025 | Ryan | A61F 2/9524 |
| 2025/0345197 | A1* | 11/2025 | Mayo | A61F 2/966 |
| 2026/0047922 | A1* | 2/2026 | Jimenez | A61F 2/2412 |
| 2026/0083559 | A1* | 3/2026 | Peckels | A61F 2/2433 |
| 2026/0114980 | A1* | 4/2026 | Yadav | A61F 2/011 |
| 2026/0174558 | A1* | 6/2026 | Lei | A61F 2/2436 |

* cited by examiner

3-Arm Hollow
Insert

| | Expanded OD (mm) | Fully Crimped OD (mm) | % Reduction |
|---|---|---|---|
| Without Leaflet Folding Guidance | 22.10 | 7.86 | 64.4 |
| With Leaflet Folding Guidance | 22.84 | 5.98 | 73.8 |

FIG. 17

METHOD FOR REDUCING PROFILE OF A VASCULAR PROSTHESIS

REFERENCED APPLICATIONS

The present application claims priority to U.S. Provisional Application Ser. No. 63/530,610 filed Aug. 3, 2023, which is fully incorporated herein by reference.

FIELD OF DISCLOSURE

The present disclosure relates generally to methods for reducing the crimped profile of a medical device, particularly to methods for reducing the crimped profile of a prosthetic heart valve, and even more particularly to methods that facilitate in the desired folding profile of the leaflets of a prosthetic heart valve during the crimping of the frame of the prosthetic heart valve to reduce the number and volume of void spaces between and about the leaflets and to reduce the crimped outer diameter profile of the prosthetic heat valve, while reducing the risk of damage to the leaflets and other components of the prosthetic heart valve during the crimping process. The method for reducing the crimped profile of a prosthetic heart valve can be accomplished by the non-simultaneous and/or non-uniform crimping of the valve frame during the crimping process.

BACKGROUND OF DISCLOSURE

Many cardiovascular devices such as stents, expandable heart valves and the like are inserted into a patient via the vascular system of a patient and then expanded at the treatment site. These devices are typically crimped onto catheter prior to insertion into a patient. The minimum diameter to which the cardiovascular device can be crimped onto the catheter will set a limit to the size of the cardiovascular passageway (e.g., blood vessel) to which the cardiovascular device can be inserted. Smaller crimp diameters can result in reduced damage to a blood vessel and/or organ (e.g., heart, etc.) when inserting into or to and/or placing the cardiovascular device at the treatment site. Smaller crimp diameters can also allow the cardiovascular device to be placed in smaller diameter blood vessels (e.g., blood vessels located in the brain, etc.).

The crimp diameter of the expandable cardiovascular device can be reduced by reducing the thickness and/or size of the frame, struts, etc. of the cardiovascular device. However, such reduction in size also affects the strength of the cardiovascular device after being expanded. After the cardiovascular device is expanded, it must retain its expanded shape at the treatment area, otherwise the cardiovascular device could become dislodged from the treatment area, could damage the treatment area, and/or fail to properly function at the treatment area. As such, cardiovascular devices formed of tradition materials such as stainless steel (e.g., 316L: 17-19 wt. % chromium, 13-15 wt. % nickel, 2-4 wt. % molybdenum, 2 wt. % max manganese, 0.75 wt. % max silicon, 0.03 wt. % max carbon, balance iron) and cobalt-chromium alloys (e.g., MP35N: 19-21 wt. % chromium, 34-36 wt. % nickel, 9-11 wt. % molybdenum, 1 wt. % max iron, 1 wt. % max titanium, 0.15 wt. % max manganese, 0.15 wt. % max silicon, 0.025 wt. % max carbon, balance cobalt) are required to maintain a frame and/or strut size/thickness that limits how small of crimping diameter can be obtained by the crimped cardiovascular device. Other types of CoCr alloys that have been used are Phynox and Elgiloy alloy (38-42 wt. % cobalt, 18-22 wt. % chromium, 14-18 wt. % iron, 13-17 wt. % nickel, 6-8 wt. % molybdenum), and L605 alloy (18-22 wt. % chromium, 14-16 wt. % W, 9-11 wt. % nickel, balance cobalt).

Medical devices such as Transcatheter aortic valves (TAVs) represent a significant advancement in prosthetic heart valve technology. TAVs bring the benefit of heart valve replacement to patients that would otherwise not be operated on. Transcatheter aortic valve replacement (TAVR) can be used to treat aortic valve stenosis in patients who are classified as high-risk for open heart surgical aortic valve replacement (SAVR). Non-limiting TAVs are disclosed in U.S. Pat. Nos. 5,411,522; 6,730,118; 10,729,543; 10,820,993; 10,856,970; 10,869,761; 10,952,852; 10,980,632; 10,980,633; and US Pub. No. 2020/0405482, all of which are incorporated fully herein by reference.

A TAV is designed to be compressed into a small diameter catheter, remotely placed within a patient's diseased aortic valve to take over the function of the native valve. Some TAVs are balloon-expandable, while others are self-expandable. In both cases, the TAVs are deployed within a calcified native valve that is forced permanently open and becomes the surface against which the frame is held in place by friction. TAVs can also be used to replace failing bioprosthetic or transcatheter valves, commonly known as a valve in valve procedure. Major TAVR advantages to the traditional surgical approaches include refraining from cardiopulmonary bypass, aortic cross-clamping and sternotomy which significantly reduces patients' morbidity.

However, several complications are associated with current TAV devices such as serious vascular injury or bleeding due to the large delivery profiles, mispositioning, crimp-induced leaflet damage, paravalvular leak, thrombosis, conduction system abnormalities and prosthesis-patient mismatch.

TAVR involves delivery, deployment, and implantation of a crimped, framed valve within a diseased aortic valve or degenerated bioprosthesis. Some limitation of the current procedure for TAVR include a) vascular complications such as dissection or severe bleeding due to the large size of the delivery system, b) high incidence of conduction system injury leading to permanent pacemaker implantation or sudden cardiac death; the conduction abnormalities are worsened by the frame recoil which necessitates that the operator reach a higher balloon inflation diameter to obtain a physiologic effective orifice area after balloon deflation, c) damage to the leaflets and/or frame during crimping of the frame of the prosthetic heart valve, and d) device failure. TAVR involves delivery, deployment, and implantation of a crimped valve frame within a diseased aortic valve or degenerated bioprosthesis. One limitation of these types of procedures is the diameter to which the valve frame can be crimped without damaging the leaflet tissues within, and vascular complications such as dissection due to the size of the delivery system.

As such, there has been an ongoing need for an improved medical device that can a) form smaller crimping diameters, b) obtain crimped diameter reductions while minimizing the damage to the leaflets during the crimping process, and/or c) addresses some of the deficiencies of prior art expandable devices such as, but not limited to, stents, TAVs and the like.

SUMMARY OF THE DISCLOSURE

The present disclosure relates to crimper systems, devices, and methods for reducing the crimped profile of a medical such as, but not limited to, a prosthetic heart valve, and more particularly to crimper systems, devices, and methods that facilitate in the desired folding profile of the leaflets of a prosthetic heart valve during the crimping of the frame of the prosthetic heart valve to reduce the number and volume of void spaces between and about the leaflets and to reduce the crimped outer diameter profile of the prosthetic heat valve, while reducing the risk of damage to the leaflets and other components of the prosthetic heart valve during the crimping process. The crimper systems, devices, and methods for reducing the crimped profile of a prosthetic heart valve can be accomplished by the non-simultaneous and/or non-uniform crimping of the valve frame during the crimping process. Although the present disclosure will particularly discuss crimper systems, devices, and methods for use with prosthetic heart valves, it will be appreciated that the crimper systems, devices, and methods in accordance with the present disclosure can be used with other types of medical devices (e.g., stent, etc.) that include a frame that needs to be crimped, plastically deformed, etc. to a smaller profile.

In one non-limiting aspect of the present disclosure, there is provided a crimper device that is configured to reduce the outer diameter of the frame of the prosthetic heart valve along a longitudinal length of the prosthetic heart valve, wherein the crimper device reduces the frame either a) gradually (in a continuous manner) or b) stepwise (in a discreet manner) from i) the inflow side to the outflow side, or ii) from the outflow side to the inflow side, thereby causing a desired and/or uniform folding pattern of the leaflets in the prosthetic heart valve, and which desired and/or uniform leaflet folding pattern results in a reduced volume profile of the leaflets, which in turn results in a reduced outer diameter or profile of the crimped prosthetic heart valve. In either the continuous or stepwise crimping method, the inflow side portion or the outflow side portion can be partially or fully crimped prior to crimping the other portions of the frame of the prosthetic heart valve. In one non-limiting embodiment, the crimper device is used to reduce the outer diameter of the frame of the prosthetic heart valve along a longitudinal length of the prosthetic heart valve in a gradual or continuous manner from the inflow side to the outflow side of the prosthetic heart valve. In another non-limiting embodiment, the crimper device is used to reduce the outer diameter of the frame of the prosthetic heart valve along a longitudinal length of the prosthetic heart valve in stepwise manner from the inflow side to the outflow side of the prosthetic heart valve.

In another one non-limiting aspect of the present disclosure, there is provided a crimper device that is configured to provide a linear or non-linear relationship between the amount a handle is moved (e.g., distance handle is moved, etc.) and the diameter or cross-sectional area of the opening. In one non-limiting configuration, the handle is configured to rotate about a handle axis. As the handle is rotated from the initial position (0° position) to the final position (e.g., 30-360° and all values and ranges therebetween), the movement of the handle about the handle axis causes a reduction in the diameter or cross-sectional area of the opening of the crimper device. In such an arrangement, for each degree of movement of the handle about the handle axis, the diameter or cross-sectional area of the opening of the crimper device can be caused proportionally reduce in size (e.g., a linear relationship between the handle rotational position and the size of the diameter or cross-sectional area of the opening) or reduce at some other rate (e.g., non-linear relationship between the handle rotational position and the size of the diameter or cross-sectional area of the opening). In another non-limiting configuration, the crimper device is configured to a) cause the inflow side portion of the prosthetic heart valve to be first partially or fully crimped, and thereafter the outflow side portion of the prosthetic heart valve to be partially or fully crimped, or b) cause the prosthetic heart valve to be progressively and continuously crimped along its longitudinal axis starting from the inflow end and thereafter progressing to and end at the outflow end of the prosthetic heart valve.

In another one non-limiting aspect of the present disclosure, there is provided a crimper device that is configured to a) progressively crimp a frame of the prosthetic heart valve from one end to the other end, b) progressively crimp a frame of the prosthetic heart valve from one portion to another portion of the frame, and c) batch crimping of different portions of the frame at different times during the crimping process (e.g., crimping a front portion of the frame prior to crimping the rear portion of the frame, etc.). Such crimping process has been found to facilitate in the folding of the leaflets in a prosthetic heart valve in an organized manner so that the frame can be crimped to smaller crimped profiles and damage to the leaflets during the crimping process is reduced.

In another one non-limiting aspect of the present disclosure, there is provided a crimper device that is configured to batch crimp the frame of the prosthetic heart valve at different portions of the frame at different times during the crimping process.

In another one non-limiting aspect of the present disclosure, there is provided a leaflet folding device that can optionally be used with the crimper device in accordance with the present disclosure to facilitate in obtaining a leaflet folding configuration during the crimping of the frame of a prosthetic heart valve so as to obtain a desired folded leaflet configuration after the frame has been fully crimped. In one non-limiting embodiment, the leaflet folding device is configured to inwardly bend one or more or all of the end portions of the leaflets that are located at or near the outflow end of the prosthetic heart valve toward the central axis of the frame of the prosthetic heart valve. Such bending of the one or more leaflets by the leaflet folding device occurs a) prior to the initial crimping of the frame of the prosthetic heart valve, and/or b) during the crimping of the frame of the prosthetic heart valve. In another non-limiting method of use, prior to and/or during the crimping of the frame, a portion or all of the leaflet folding device is rotated (e.g., 2-180° and all values and ranges therebetween) about the longitudinal axis of the frame (e.g., central longitudinal axis of the frame, etc.) so as to facilitate in the folding of the leaflets during the crimping of the frame. Such rotation of the is used to facilitate in the folding of the leaflets. Such rotation of the one or more leaflets by the leaflet folding device occurs a) prior to the initial crimping of the frame of the prosthetic heart valve, and/or b) during the crimping of the frame of the prosthetic heart valve. One or more portions of the leaflet folding device can include a coating to a) limit or prevent damage to the frame and/or leaflets when one or more portions of the leaflet folding device engages the frame and/or leaflets during the crimping process, b) limit or prevent contamination of the frame and/or leaflets when one or more portions of the leaflet folding device engages the frame and/or leaflets during the crimping process, c) reduce friction between one or more portions of the leaflet folding device and the frame and/or leaflets during the crimping process, and/or d) form a surface color on one or more portions of the leaflet folding device to facilitate in visually positioning and using the leaflet folding device during the crimping process. The type and thickness of the coating, when used, is non-limiting.

In another one non-limiting aspect of the present disclosure, there is provided a leaflet folding device that can optionally be used with the crimper device in accordance with the present disclosure to facilitate in obtaining a leaflet folding configuration during the crimping of the frame of a prosthetic heart valve so as to obtain a desired folded leaflet configuration after the frame has been fully crimped and wherein the leaflet folding device is removed from or disengaged from the one or more leaflets prior to the outflow end of the frame of the prosthetic heart valve being 5-99% fully crimped (and all values and ranges therebetween). In another non-limiting method, the leaflet folding device is removed from or disengaged from the one or more leaflets prior to the outflow end of the frame of the prosthetic heart valve being 25-99% fully crimped. In another non-limiting method, the leaflet folding device is removed from or disengaged from the one or more leaflets prior to the outflow end of the frame of the prosthetic heart valve being 30-75% fully crimped. In another non-limiting method, the leaflet folding device is removed from or disengaged from the one or more leaflets after the outflow end of the frame of the prosthetic heart valve is fully crimped.

In accordance with another non-limiting aspect of the present disclosure, there is provided another device and method for folding the leaflets on a prosthetic heart valve that includes the step of inserting a radially collapsible insert inside the prosthetic heart valve prior to the partial crimping of the prosthetic heart valve. The prosthetic heart valve is then partially crimped (10-90% fully crimped and all values and ranges therebetween) while the radially collapsible insert is inside the prosthetic heart valve. Generally, the radially collapsible insert is inserted 50-100% (and all values and ranges therebetween) along the longitudinal length of the prosthetic heart valve. After the prosthetic heart valve is partially crimped, the radially collapsible insert is removed from the prosthetic heart valve and the prosthetic heart valve is then subjected to further crimping by the crimping device until the prosthetic heart valve is fully crimped. The radially collapsible insert can be designed to be reusable or be designed for a single use. The material used to form the radially collapsible insert is non-limiting (e.g., metal, plastic, paper, composite material, etc.). The cross-sectional shape of the radially collapsible insert prior to the insertion of the radially collapsible insert into the prosthetic heart valve can be constant or variable along the longitudinal length of the radially collapsible insert. During the crimping process involving the radially collapsible insert, the type of crimping process used to partially crimp the prosthetic heart valve while the radially collapsible insert is partially or fully inserted in the prosthetic heart valve is non-limiting. Such crimping processes can include a) a traditional prior art crimping process wherein the complete prosthetic heart valve is subjected to crimping forces, b) a stepwise crimping process wherein one portion of the prosthetic heart valve is subjected to crimping forces and then other portions of the prosthetic heart valve are subjected to crimping forces, and/or c) a progressive continuous crimping process wherein the crimping of the prosthetic heart valve starts at the inflow end or the outflow end and the crimping continuously progresses along the longitudinal length of the prosthetic heart valve to the opposite end of the prosthetic heart valve. After the radially collapsible insert is removed from the prosthetic heart valve, the crimping process used to complete the crimping of the prosthetic heart valve can include a) a traditional prior art crimping process wherein the complete prosthetic heart valve is subjected to crimping forces, b) a stepwise crimping process wherein one portion of the prosthetic heart valve is subjected to crimping forces and then other portions of the prosthetic heart valve are subjected to crimping forces, and/or c) a progressive continuous crimping process wherein the crimping of the prosthetic heart valve starts at the inflow end or the outflow end and the crimping continuously progresses along the longitudinal length of the prosthetic heart valve to the opposite end of the prosthetic heart valve. In one non-limiting method, during use of the radially collapsible insert while it is at least partially inserted in the prosthetic heart valve, the radially collapsible insert can be held or mounted to not rotate during the partial crimping of the prosthetic heart valve. In another non-limiting method, during use of the radially collapsible insert while it is at least partially inserted in the prosthetic heart valve, the radially collapsible insert can be rotated during the partial crimping of the prosthetic heart valve.

In accordance with another non-limiting aspect of the present disclosure, there is provided another device and method for folding the leaflets on a prosthetic heart valve that includes the step of inserting a radially collapsible insert inside the prosthetic heart valve prior to the partial crimping of the prosthetic heart valve wherein the cross-sectional shape of the radially collapsible insert prior to the insertion of the radially collapsible insert into the prosthetic heart valve is constant along the longitudinal length of the radially collapsible insert. The cross-sectional area of the radially collapsible insert prior to the insertion of the radially collapsible insert into the prosthetic heart valve can be constant or variable along the longitudinal length of the radially collapsible insert. In one non-limiting configuration, the cross-sectional area of the radially collapsible insert prior to the insertion of the radially collapsible insert into the prosthetic heart valve is constant along the longitudinal length of the radially collapsible insert.

In accordance with another non-limiting aspect of the present disclosure, there is provided another device and method for folding the leaflets on a prosthetic heart valve that includes the step of inserting a radially collapsible insert inside the prosthetic heart valve prior to the partial crimping of the prosthetic heart valve wherein the radially collapsible insert has a generally circular or oval cross-sectional shape along the longitudinal length of the radially collapsible insert. The radially collapsible insert can have a generally circular or oval cross-sectional shape along a portion (e.g., 10-99% and all values and ranges therebetween) or full longitudinal length of the radially collapsible insert. In one non-limiting configuration, the generally circular or oval cross-sectional shape of the radially collapsible insert has a generally constant cross-sectional size along 20-100% (and all values and ranges therebetween) the longitudinal length of the radially collapsible insert. In another non-limiting configuration, the radially collapsible insert has a hollow interior cavity along 20-100% (and all values and ranges therebetween) of the longitudinal length of the radially collapsible insert. In another non-limiting configuration, the hollow interior cavity has a generally circular or oval cross-sectional shape along a portion (e.g., 10-99% and all values and ranges therebetween) or full longitudinal length of the radially collapsible insert. The shape and/or cross-sectional area of the hollow interior cavity along the longitudinal length of the radially collapsible insert is generally constant; however, this is not required. The thickness of the walls and the material used to form the radially collapsible insert is selected such that the radially collapsible insert is caused to at least partially collapse when the prosthetic heart valve is partially crimped by a crimping device. Generally, the thickness of the wall of the radially collapsible insert is 0.1-10% (and all values and ranges therebetween) of the longest cross-sectional length or diameter of the radially collapsible insert. The radially collapsible insert is configured such that as the prosthetic heart valve is crimped, the leaflets will engage in the outer surface of the radially collapsible insert and be caused to initially fold in a certain way based on the engagement with the radially collapsible insert and the radial reduction of the frame of the prosthetic heart valve. During the partial crimping of the prosthetic heart valve, the radially collapsible insert is also caused to partially collapse due to the inwardly radial forces on the outer surface of the radially collapsible insert by the leaflets and the frame of the prosthetic heart valve. The partially collapsed shape of the radially collapsible insert also facilitates in the desired folding patterning of the leaflets as the prosthetic heart valve is crimped. Once the prosthetic heart valve is partially crimped, the radially collapsible insert is fully removed from the interior of the prosthetic heart valve and thereafter the prosthetic heart valve is subjected to a final crimping process to fully crimp the prosthetic heart valve. During the final crimping process, the leaflets are continued to be caused to fold in a desired manner to reduce or minimize the volume of the leaflets after the prosthetic heart valve is fully crimped. This continued desired leaflet folding is at least partially or fully the result of the initial folding of the leaflets when using the radially collapsible insert.

In accordance with another non-limiting aspect of the present disclosure, there is provided another device and method for folding the leaflets on a prosthetic heart valve that includes the step of inserting a radially collapsible insert inside the prosthetic heart valve prior to the partial crimping of the prosthetic heart valve wherein the radially collapsible insert has a plurality of arms extending outwardly from the outer surface of the radially collapsible insert. Generally, the number of arms on the radially collapsible insert is the same as the number of leaflets in the prosthetic heart valve; however, this is not required. The shape and/or cross-sectional area of the hollow interior cavity along the longitudinal length of the radially collapsible insert is generally constant; however, this is not required. The body and/or arms can optionally include a hollow interior cavity. When the body and/or arms include a hollow interior cavity, the hollow interior cavity extends 10-100% (and all values and ranges therebetween) of the longitudinal length of the radially collapsible insert. The thickness of the walls and the material used to form the radially collapsible insert is selected such that the radially collapsible insert is caused to at least partially collapse when the prosthetic heart valve is partially crimped by a crimping device. Generally, the thickness of the wall of the radially collapsible insert is 0.1-10% (and all values and ranges therebetween) of the longest cross-sectional length or diameter of the radially collapsible insert. Each of the arms can have the same or different size, shape, thickness, length, width, and/or configuration. Generally, two or more or all adjacently positioned arms can be equally spaced from one another about the outer circumference of the body of the radially collapsible insert; however, this is not required. Generally, the arms are formed of the same material as the body of the radially collapsible insert; however, this is not required. The length of each arm is generally 2-40 mm (and all values and ranges therebetween; 3-30 mm, etc.). Generally, one or more or all of the arms extend 60-100% (and all values and ranges therebetween) the longitudinal length of the radially collapsible insert. The angle $\alpha$ at which each arm initially extends from the outer surface of the body of the radially collapsible insert is 5-175° (and all values and ranges therebetween). The angle $\alpha$ for two or more or all arms can be the same or different. The shape of the arms extending from the outer surface of the body can be straight curved, wavy, etc. The number, shape, size, and configuration of the arms on the radially collapsible insert are selected to facilitate in the desired folding of the leaflets as the prosthetic heart valve is initially crimped. The radially collapsible insert with the one or more arms can be configured such that as the prosthetic heart valve is crimped, the leaflets will engage in the arms and the outer surface of the radially collapsible insert and be caused to initially fold in a certain way based on the engagement with the arms and outer surface of radially collapsible insert and the radial reduction of the frame of the prosthetic heart valve. During the partial crimping of the prosthetic heart valve, the radially collapsible insert is also caused to partially collapse due to the inwardly radial forces on the arm and/or outer surface of the radially collapsible insert by the leaflets and the frame of the prosthetic heart valve. The partially collapsed shape of the radially collapsible insert also facilitates in the desired folding patterning of the leaflets as the prosthetic heart valve is crimped. Once the prosthetic heart valve is partially crimped, the radially collapsible insert is fully removed from the interior of the prosthetic heart valve and thereafter the prosthetic heart valve is subjected to a final crimping process to fully crimp the prosthetic heart valve. During the final crimping process, the leaflets are continued to be caused to fold in a desired manner to reduce or minimize the volume of the leaflets after the prosthetic heart valve is fully crimped. This continued desired leaflet folding is at least partially or fully the result of the initial folding of the leaflets when using the radially collapsible insert. In one non-limiting configuration, the radially collapsible insert includes three arms. Each of the three arms has generally the same shape, thickness, length, width, and configuration. The three arms are spaced such that adjacently positioned arms are equally spaced from one another about the outer circumference of the body of the radially collapsible insert. Each of the arms extends 80-100% (and all values and ranges therebetween) the longitudinal length of the radially collapsible insert. Each of the arms has a slightly curve shape, a length of 3-10 mm (and all values and ranges therebetween), and an angle $\alpha$ that is 15-60° (and all values and ranges therebetween).

In accordance with another non-limiting aspect of the present disclosure, there is provided another device and method for folding the leaflets on a prosthetic heart valve that includes the step of inserting a forming shaft inside the prosthetic heart valve prior to the partial crimping of the prosthetic heart valve wherein the forming shaft has a plurality of arms extending outwardly from the outer surface of the forming shaft. Generally, the number of arms on the forming shaft is the same as the number of leaflets in the prosthetic heart valve; however, this is not required. One non-limiting embodiment, a portion of the forming shaft (e.g., the end portion, mid-portion, front portion, etc.) includes the plurality of arms. The plurality of arms can extend 1-100% (and all values and ranges therebetween) along the longitudinal length of the forming shaft. The forming shaft can have a body that is not limited in shape. Each of the arms can have the same or different size, shape, thickness, length, width, and/or configuration. Generally, two or more or all adjacently positioned arms are equally spaced from one another about the outer circumference of the body of the forming shaft; however, this is not required. Generally, the arms are formed of the same material as the body of the forming shaft; however, this is not required. The length of each arm is generally 2-40 mm (and all values and ranges therebetween; 3-30 mm, etc.). The angle at which each arm initially extends from the outer surface of the body of the radially collapsible insert is 5-175° (and all values and ranges therebetween). The angle for two or more or all arms can be the same or different. The shape of the arms that extend from the outer surface of the body can be straight curved, wavy, etc. The number, shape, size, and configuration of the arms on the forming shaft are selected to facilitate in the desired folding of the leaflets as the prosthetic heart valve is initially crimped. The forming shaft and/or one or more of the arms can be formed of a non-flexible or rigid material such that during the crimping of the prosthetic heart valve, the shaft and/or one or more of the arms flexes or bends 0-10% (and all values and ranges therebetween). In one non-limiting configuration, the shaft and/or one or more of the arms is formed of a hard plastic material, ceramic material, metal material, and/or composite material. The forming shaft with the one or more arms is configured such that as the prosthetic heart valve is crimped, the leaflets will engage in the arms and be caused to initially fold in a certain way based on the engagement with the arms and the radial reduction of the frame of the prosthetic heart valve. Once the prosthetic heart valve is partially crimped, the forming shaft is fully removed from the interior of the prosthetic heart valve and thereafter the prosthetic heart valve is subjected to a final crimping process to fully crimp the prosthetic heart valve. During the final crimping process, the leaflets are continued to be caused to fold in a desired manner to reduce or minimize the volume of the leaflets after the prosthetic heart valve is fully crimped. This continued desired leaflet folding is at least partially or fully the result of the initial folding of the leaflets when using the radially collapsible insert. In one non-limiting configuration, the forming shaft includes three arms. Each of the three arms has generally the same shape, thickness, length, width, and configuration. The three arms are spaced such that adjacently positioned arms are equally spaced from one another about the outer circumference of the body of the forming shaft. Each of the arms extends 5-50% (and all values and ranges therebetween) the longitudinal length of the forming shaft. Each of the arms has a slightly curve shape, a length of 3-10 mm (and all values and ranges therebetween), and an angle $\alpha$ that is 15-60° (and all values and ranges therebetween). After the forming shaft is removed from the prosthetic heart valve, the crimping processes that can be used to complete the crimping of the prosthetic heart valve can include a) a traditional prior art crimping process wherein the complete prosthetic heart valve is subjected to crimping forces, b) a stepwise crimping process wherein one portion of the prosthetic heart valve is subjected to crimping forces and then other portions of the prosthetic heart valve are subjected to crimping forces, and/or c) a progressive continuous crimping process wherein the crimping of the prosthetic heart valve starts at the inflow end or the outflow end and the crimping continuously progresses along the longitudinal length of the prosthetic heart valve to the opposite end of the prosthetic heart valve. In one non-limiting method, during use of the forming shaft while it is at least partially inserted in the prosthetic heart valve, the forming shaft can be held or mounted to not rotate during the partial crimping of the prosthetic heart valve. In another non-limiting method, during use of the forming shaft while it is at least partially inserted in the prosthetic heart valve, the forming shaft can be allowed to rotate during the partial crimping of the prosthetic heart valve.

In accordance with another non-limiting aspect of the present disclosure, there is provided another device and method for folding the leaflets on a prosthetic heart valve that includes the step of inserting a fold guide instrument at least partially in the interior of the prosthetic heart valve prior to the crimping of the prosthetic heart valve. The fold guide instrument includes two or more prongs that are configured to engage a portion of two or more leaflets as the prosthetic heart valve is partially crimped. The prongs of the fold guide instrument can be configured such that one or more or all of the prongs can be inserted 10-100% (and all values and ranges therebetween) along the longitudinal length of the prosthetic heart valve. The prongs can be configured that two or more or all of the prongs have the same shape, size, length, width, cross-sectional shape, and/or configuration. The prongs can be oriented that two or more of the adjacently positioned prongs have the same spacing from one another. In one non-limiting arrangement, the width and/or thickness of one or more or all of the prongs is 0.02-8 mm (and all values and ranges therebetween; 0.05-5 mm, etc.). The one or more prongs are generally configured to be flexible so the one or more prongs bend as the prosthetic heart valve is partially crimped. The material used to form the fold guide instrument is non-limiting (e.g., metal, plastic, paper, composite material, etc.). During use, the prongs of the fold guide instrument are inserted into the interior of the prosthetic heart valve along a portion or the complete longitudinal length of the prosthetic heart valve prior to crimping the prosthetic heart valve. As the prosthetic heart valve is partially crimped, the prongs on the fold guide instrument engage one or more leaflets and cause the leaflets to initially fold in a certain way based on the engagement of the leaflets with the prongs of the fold guide instrument. During the partial crimping of the prosthetic heart valve, the prongs of the fold guide instrument are caused to partially bend due to the inwardly radial forces on the prongs by the leaflets and/or the frame of the prosthetic heart valve. Once the prosthetic heart valve is partially crimped, the fold guide instrument is removed from the interior of the prosthetic heart valve and thereafter the prosthetic heart valve is subjected to a final crimping process to fully crimp the prosthetic heart valve. During the final crimping process, the leaflets are continued to be caused to fold in a desired manner to reduce or minimize the volume of the leaflets after the prosthetic heart valve is fully crimped. This continued desired leaflet folding is at least partially or fully the result of the initial folding of the leaflets when using the fold guide instrument. During the crimping process that involves the use of the fold guide instrument, the type of crimping process used to partially crimp the prosthetic heart valve while the radially collapsible insert is partially or fully inserted in the prosthetic heart valve is non-limiting. Such crimping processes can include a) a traditional prior art crimping process wherein the complete prosthetic heart valve is subjected to crimping forces, b) a stepwise crimping process wherein one portion of the prosthetic heart valve is subjected to crimping forces and then other portions of the prosthetic heart valve are subjected to crimping forces, and/or c) a progressive continuous crimping process wherein the crimping of the prosthetic heart valve starts at the inflow end or the outflow end and the crimping continuously progresses along the longitudinal length of the prosthetic heart valve to the opposite end of the prosthetic heart valve.

After the fold guide instrument is removed from the prosthetic heart valve, the crimping processes that can be used to complete the crimping of the prosthetic heart valve can include a) a traditional prior art crimping process wherein the complete prosthetic heart valve is subjected to crimping forces, b) a stepwise crimping process wherein one portion of the prosthetic heart valve is subjected to crimping forces and then other portions of the prosthetic heart valve are subjected to crimping forces, and/or c) a progressive continuous crimping process wherein the crimping of the prosthetic heart valve starts at the inflow end or the outflow end and the crimping continuously progresses along the longitudinal length of the prosthetic heart valve to the opposite end of the prosthetic heart valve. In one non-limiting method, during use of the fold guide instrument while it is at least partially inserted in the prosthetic heart valve, the fold guide instrument can be held or mounted to not rotate during the partial crimping of the prosthetic heart valve. In another non-limiting method, during use of the fold guide instrument while it is at least partially inserted in the prosthetic heart valve, the fold guide instrument can be allowed to rotate during the partial crimping of the prosthetic heart valve. In non-limiting embodiment, the fold guide instrument includes three prongs. Each of the three prongs has generally the same shape, thickness, length, width, and configuration. The three prongs are spaced such that adjacently positioned prongs are equally spaced from one another. Each of the prongs is configured to extend 10-100% (and all values and ranges therebetween) the longitudinal length of the interior of the prosthetic heart valve. Each of the prongs has a thickness and/or width of 0.05-3 mm (and all values and ranges therebetween).

In another non-limiting aspect of the present disclosure, there is provided a leaflet folding device that can optionally be used with the crimper device in accordance with the present disclosure to facilitate in obtaining a leaflet folding configuration during the crimping of the frame of a prosthetic heart valve, and wherein the leaflet folding device includes a handle portion and one or more leaflet engagement members that are attached to and extend from the handle portion. In one non-limiting configuration, the handle portion is sized and shaped such that it can be grasped by a user to enable the user to position the one or more leaflet engagement members into a portion of the prosthetic heart valve to cause the bending of the one or more leaflets. The shape and length and material and size of the handle portion are non-limiting. In one non-limiting specific configuration, the handle portion has a cylindrical shape and a length of 1-12 inches (and all values and ranges therebetween) and a cross-sectional area that is 10-95% (and all values and ranges therebetween) of the cross-sectional area of the outflow end of the frame prior to the crimping of the frame (e.g., the cross-sectional area of the outflow end of the frame in the fully expanded position, etc.). In another non-limiting configuration, the one or more leaflet engagement members that are attached to the distal end or distal end portion of the handle portion. The type of connection used to attach the one or more leaflet engagement members to the handle is non-limiting. In one non-limiting configuration, the one or more leaflet engagement members extend radially outwardly (e.g., 5-45° radially outwardly and all values and ranges therebetween) from the central longitudinal axis of the handle portion. When the leaflet folding device includes two or more leaflet engagement members, two or more or all of the leaflet engagement members can have the same size, shape, and/or be formed of the same material; however, this is not required. In another non-limiting configuration, one or more of the leaflet engagement members are formed of a flexible material that enables the one or more leaflet engagement members to flex and/or bend a) when positioning the one or more leaflet engagement members about one or more leaflets, and/or b) during the crimping of the frame of the prosthetic heart valve and while the one or more leaflet engagement members are still engaged with the one or more leaflets during the crimping of the frame. In another non-limiting configuration, the one or more leaflet engagement members are each formed of a wire loop (e.g., metal wire loop, plastic wire loop, etc.). In another non-limiting embodiment, the leaflet folding device is moved along the longitudinal axis of the frame and toward the frame until the one or more leaflet engagement members engage the end or end portion of the one or more leaflets. Thereafter, the leaflet folding device continued to be moved along the longitudinal axis of the frame such that the end or end portion of the one or more leaflet engagement members move between the one or more leaflets and the inner surface of the frame. As the leaflet folding device is continued to be moved along the longitudinal axis of the frame, the angular orientation of the one or more leaflet engagement members relative to the central axis of the handle portion of the leaflet folding device causes the end and end portions of the leaflets to be bent toward the central axis of the frame. Generally, the size and configuration of the end region of the one or more leaflet engagement members inhibits or prevents the end or end region of the one or more leaflet engagement members from passing through the side openings in the frame of the prosthetic heart valve. Furthermore, the one or more leaflet engagement members generally are inserted only through a portion of the longitudinal length of the frame (e.g., 1-80% of the longitudinal length and all values and ranges therebetween). In one non-limiting method of use, one or more leaflet engagement members are inserted only through a portion of the longitudinal length of the frame and are spaced form the region of the frame wherein the one or more leaflets are connected to the frame.

In another non-limiting aspect of the present disclosure, there is provided a leaflet folding device that can optionally be used with the crimper device in accordance with the present disclosure to facilitate in obtaining a leaflet folding configuration during the crimping of the frame of a prosthetic heart valve so as to obtain a desired folded leaflet configuration after the frame has been fully crimped, and wherein the leaflet folding device includes a cylindrical body portion that is configured to be partially or fully inserted into the prosthetic device a) prior to the initial crimping of the frame of the prosthetic heart valve, and/or b) during the crimping of the frame of the prosthetic heart valve. The cylindrical body portion can be a) a solid structure, b) a hollow structure that includes a cavity that extends partially or fully along the longitudinal length of the cylindrical body, or c) a cylindrical body that includes one or more internal void spaces and/or surface cavities. The diameter and/or cross-sectional area of the portion of the cylindrical body portion that is configured to be inserted into the prosthetic heart valve and can a) be constant along 50-100% (and all values and ranges therebetween) of the longitudinal length of such cylindrical body portion, or b) vary along the longitudinal length of such cylindrical body portion. The cylindrical body portion can optionally be formed of a flexible material (e.g., plastic material, foam material, etc.). In one non-limiting configuration, the outer diameter of the cylindrical body portion of the leaflet folding device that is configured to be partially or fully inserted into the prosthetic device is about 5-90% (and all values and ranges therebetween) of the inner diameter of the frame of the prosthetic heart valve prior to being crimped. In another non-limiting method, the cylindrical body portion of the leaflet folding device is removed from the frame of the prosthetic heart valve prior to the inner diameter of the frame of the prosthetic heart being reduced during the crimping process to a diameter that is 0-20% (and all values and ranges therebetween) greater than the outer diameter of the cylindrical body portion of the leaflet folding device. In one non-limiting method of use, the cylindrical body portion of the leaflet folding device is positioned within the region of the leaflets such that the leaflets are located between the cylindrical body portion of the leaflet folding device and the frame. During the crimping of the frame of the prosthetic heart valve, the cylindrical body portion of the leaflet folding device can be a) moved along the longitudinal axis of the frame, and/or b) rotated about the longitudinal axis of the frame.

In another non-limiting aspect of the present disclosure, the medical device is a valve (e.g., heart valve, TAVR valve, aortic, mitral valve replacement, tricuspid valve replacement, pulmonary valve replacement, etc.). In one non-limiting embodiment, the medical device includes an expandable frame, more particularly the medical device is in the form of a cardiovascular implant for the treatment of structural heart disease wherein the cardiovascular implant includes an expandable frame, and still more particularly to a medical device is in the form of a prosthetic heart valve for the for the treatment of structural heart disease wherein the prosthetic heart valve includes an expandable frame that is optionally formed of a rhenium containing metal alloy.

In another non-limiting aspect of the present disclosure, the medical device is a valve that includes a frame that is formed of a rhenium containing metal alloy that allows for a novel structural prosthetic heart valve frame geometry. The combination of the rhenium containing metal alloy and the novel geometry of the frame of the prosthetic heart valve addresses the current deficiencies of prosthetic heart valves that are discussed above. The novel geometry of the frame of the prosthetic heart valve in combination with the frame being partially (e.g., 10-99.99 wt. % and all values and ranges therebetween) or fully formed of the rhenium containing alloy enable the formation of a frame that a) has an open cell geometry that can be used to reduce delivery system size thereby reducing vascular and neurological complications, b) has an open cell pattern that has high radial strength due to the high yield strength and ultimate tensile strength of the rhenium containing metal alloy, c) has improved restoration of the physiologic EOA in challenging, heavily calcified valves that exert high force on the bioprosthetic valve, while also allowing a reduced crimp diameter for vascular access, d) has improved restoration of the physiologic EOA that results in greater longevity of the bioprosthetic valve, c) has lower recoil than traditional materials used to form frames such as stainless steel, chromium-cobalt, or titanium alloys, thereby resulting in less recoil of the frame when expanded which leads to decreased risk of valve embolization, decreased paravalvular leak due to improved conformability of the native anatomy, more accurate restoration of the physiologic EOA, and decrease conduction system injury due to a lower balloon inflation diameter required to obtain the physiologic EOA after balloon inflation, f) has an open cell geometry that is configured to have little (e.g., 0-20% longitudinal foreshortening along a longitudinal axis of the expandable frame and all values and ranges therebetween) or no foreshortening when expanded, which allows for more accurate placement of the valve in the native annulus, and wherein a frame that has little or no longitudinal foreshortening when expanded can be expanded with a shorter balloon, which use of a shorter balloon for frame expansion can decrease conduction system injury, g) has commissural alignment markers and an open cell between the commissures that allows for proper placement of the bioprosthetic valve in relation to the native commissures of the valve for proper hemodynamic function in regard to wash out of the valve and blood flow to the coronaries, which leads to better durability and longevity of the valve, and access and re-intervention of the coronaries preventing future adverse events, h) has an open cell geometry with radial symmetry, longitudinal symmetry, and little or no longitudinal foreshortening which allows for symmetrical and cylindrical expansion of the prosthetic valve resulting in lower rates of leaflet thrombosis and structural valve deterioration, and i) is formed of a rhenium containing metal alloy with no nickel content that prevents allergic response due to the presence of nickel and restenosis associated with nickel content.

In one non-limiting aspect of the disclosure, the prosthetic heart valve (e.g., heart valve, TAVR valve, mitral valve replacement, tricuspid valve replacement, pulmonary valve replacement, etc.) includes a radially collapsible and expandable frame and a leaflet structure that comprises a plurality of leaflets. In another non-limiting embodiment, the prosthetic heart valve optionally includes an annular skirt or cover member that is disposed on and partially or fully covering or overlaid over the cells of at least a portion of the frame. In another non-limiting embodiment, the frame of the prosthetic heart valve comprises a plurality of interconnected axial longitudinal member, angular articulating members and strut joints that define a plurality of open cells in the frame.

In another and/or alternative non-limiting aspect of the disclosure, the frame of the prosthetic heart valve is optionally partially or fully formed of a) a refractory metal alloy and/or b) a metal alloy that includes at least 15 atomic weight percent (awt. %) or atomic percent (awt. %) rhenium so as to create a "rhenium effect" in the metal alloy. As used herein, atomic weight percent (awt. %) or atomic percentage (awt. %) or atomic percent (awt. %) are used interchangeably. As defined herein, the weight percentage (wt. %) of an element is the weight of that element measured in the sample divided by the weight of all elements in the sample multiplied by 100. The atomic percentage or atomic weight percent (awt. %) is the number of atoms of that element, at that weight percentage, divided by the total number of atoms in the sample multiplied by 100. The use of the terms weight percentage (wt. %) and atomic percentage or atomic weight percentage (awt. %) are two ways of referring to metallic alloy and its constituents. It has been found that for several metal alloys the inclusion of at least 15 awt. % rhenium results in the ductility and/or tensile strength of the metal alloy to improve as compared to a metal alloy is that absent rhenium. Such improvement in ductility and/or tensile strength due to the inclusion of at least 15 awt. % rhenium in the metal alloy is referred to as the "rhenium effect." As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. As defined herein, a refractory metal alloy is a metal alloy that includes at least 20 wt. % of one or more of molybdenum, rhenium, niobium, tantalum or tungsten. Non-limiting refractory metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc. In one non-limiting arrangement, 50-100 wt. % (and all values and ranges therebetween) of the expandable frame of the prosthetic heart valve is formed of a refractory metal alloy or a metal alloy that includes at least 15 awt. % rhenium. In another non-limiting arrangement, the metal alloy that is used to partially or fully form the expandable frame of the prosthetic heart valve includes at least 30 wt. % (e.g., 30-99 wt. % and all values and ranges therebetween) of one or more of molybdenum, rhenium, niobium, tantalum or tungsten. In another non-limiting embodiment, the refractory metal alloy or the metal alloy that includes at least 15 awt. % rhenium can be used to 1) increase the radiopacity of the frame of the prosthetic heart valve, 2) increase the radial strength of the frame of the prosthetic heart valve, 3) increase the yield strength and/or ultimate tensile strength of the frame of the prosthetic heart valve, 4) improve the stress-strain properties of the frame of the prosthetic heart valve, 5) improve the crimping and/or expansion properties of the frame of the prosthetic heart valve, 6) improve the bendability and/or flexibility of the frame of the prosthetic heart valve, 7) improve the strength and/or durability of the frame of the prosthetic heart valve, 8) increase the hardness of the frame of the prosthetic heart valve, 9) improve the biostability and/or biocompatibility properties of the frame of the prosthetic heart valve, 10) increase fatigue resistance of the frame of the prosthetic heart valve, 11) resist cracking in the frame of the prosthetic heart valve, 12) resist propagation of cracks in the frame of the prosthetic heart valve, 13) enable smaller, thinner, and/or lighter weight frames of the prosthetic heart valve to be made, 14) facilitate in the reduction of the outer diameter of a crimped prosthetic heart valve, 15) improve the conformity of the frame of the prosthetic heart valve to the shape of the treatment area when the prosthetic heart valve is expanded in the treatment area, 16) reduce the amount of recoil of the frame of the prosthetic heart valve after the frame is expanded in the treatment area, 17) reduce adverse tissue reactions with the frame of the prosthetic heart valve, 18) reduce metal ion release from the frame after implantation of the prosthetic heart valve, 19) reduce corrosion of the frame of the prosthetic heart valve after implantation of the prosthetic heart valve, 20) reduce allergic reaction with the frame of the prosthetic heart valve after implantation of the prosthetic heart valve (e.g., reduce nickel content of metal alloy, etc.), 21) improve hydrophilicity of the frame of the prosthetic heart valve, 22) reduce magnetic susceptibility of the frame of the prosthetic heart valve, 23) reduced longitudinal foreshortening the frame of the prosthetic heart valve when the frame of the prosthetic heart valve is expanded, and/or 24) reduce toxicity of the frame of the prosthetic heart valve after implantation of the prosthetic heart valve.

In another and/or alternative non-limiting aspect of the disclosure, the frame of the prosthetic heart valve is optionally partially (e.g. 1-99.999 wt. % and all values and ranges therebetween) or fully formed of a metal material that includes a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) titanium-nickel alloy, 1) refractory metal alloy, or m) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 atomic weight percent (awt. %) or atomic percent (awt. %) rhenium (e.g., 5-99 awt. % rhenium and all values and ranges therebetween). As defined herein, a stainless-steel alloy (SS alloy) includes at least 50 wt. % (weight percent) iron, 10-28 wt. % chromium, 0-35 wt. % nickel, and optionally one or more of 0-4 wt. % molybdenum, 0-2 wt. % manganese, 0-0.75 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Sc, 0-2 wt. % vanadium, and 0-2 wt. % tungsten. A 316L alloy that falls within a stainless-steel alloy includes 17-19 wt. % chromium, 13-15 wt. % nickel, 2-4 wt. % molybdenum, 2 wt. % max manganese, 0.75 wt. % max silicon, 0.03 wt. % max carbon, balance iron. As defined herein, a cobalt-chromium alloy (CoCr alloy) includes 30-68 wt. % cobalt, 15-32 wt. % chromium, and optionally one or more of 1-38 wt. % nickel, 2-18 wt. % molybdenum, 0-18 wt. % iron, 0-1 wt. % titanium, 0-0.15 wt. % manganese, 0-0.15 wt. % silver, 0-0.25 wt. % carbon, 0-16 wt. % tungsten, 0-2 wt. % silicon, 0-2 wt. % aluminum, 0-1 wt. % iron, 0-0.1 wt. % boron, 0-0.15 wt. % silver, and 0-2 wt. % titanium. As a MP35N alloy that falls within a CoCr alloy includes 18-22 wt. % chromium, 32-38 wt. % nickel, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. %, 0-0.1 wt. % boron, 0-0.15 wt. % silver, and balance cobalt. As defined herein, a Phynox and Elgiloy alloy that falls within a CoCr alloy includes 38-42 wt. % cobalt, 18-22 wt. % chromium, 14-18 wt. % iron, 13-17 wt. % nickel, 6-8 wt. % molybdenum. As defined herein, a L605 alloy that falls within a CoCr alloy includes 18-22 wt. % chromium, 14-16 wt. % tungsten, 9-11 wt. % nickel, balance cobalt. As defined herein, a titanium-aluminum-vanadium alloy (TiAlV alloy) includes 4-8 wt. % aluminum, 3-6 wt. % vanadium, 80-93 wt. % titanium, and optionally one or more of 0-0.4 wt. % iron, 0-0.2 wt. % carbon, 0-0.5 wt. % yttrium. A Ti-6Al-4V alloy that falls with a TiAlV alloy includes incudes 3.5-4.5 wt. % vanadium, 5.5-6.75 wt. % aluminum, 0.3 wt. % max iron, 0.08 wt. % max carbon, 0.05 wt. % max yttrium, balance titanium. As defined herein, an aluminum alloy includes 80-99 wt. % aluminum, and optionally one or more 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper. As defined herein, a nickel alloy includes 30-98 wt. % nickel, and optionally one or more 5-25 wt. % chromium, 0-65 wt. % iron, 0-30 wt. % molybdenum, 0-32 wt. % copper, 0-32 wt. % cobalt, 2-2 wt. % aluminum, 0-6 wt. % tantalum, 0-15 wt. % tungsten, 0-5 wt. % titanium, 0-6 wt. % niobium, 0-3 wt. % silicon. As defined herein, a titanium alloy includes 80-99 wt. % titanium, and optionally one of more of 0-6 wt. % aluminum, 0-3 wt. % tin, 0-1 wt. % palladium, 0-8 wt. % vanadium, 0-15 wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron. As defined herein, a tungsten alloy includes 85-98 wt. % tungsten, and optionally one or more of 0-8 wt. % nickel, 0-5 wt. % copper, 0-5 wt. % molybdenum, 0-4 wt. % iron. As defined herein, a molybdenum alloy includes 90-99.5 wt. % molybdenum, and optionally one or more of 0-1 wt. % nickel, 0-1 wt. % titanium, 0-1 wt. % zirconium, 0-30 wt. % tungsten, 0-2 wt. % hafnium, 0-2 wt. % lanthanum. As defined herein, a copper alloy includes 55-95 wt. % copper, and optionally one or more of 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 wt. % cobalt, 0-20 wt. % nickel. As defined herein, a beryllium-copper alloy includes 95-98.5 wt. % copper, 1-4 wt. % beryllium, and optionally one or more of 0-1 wt. % cobalt, and 0-0.5 wt. % silicon. As defined herein, a titanium-nickel alloy (e.g., Nitinol alloy) includes 42-58 wt. % nickel and 42-58 wt. % titanium.

In accordance with another and/or alternative aspect of the present disclosure, the metal alloy that is used to partially or fully form the frame of the prosthetic heart valve includes at least 5 awt. % (e.g., 5-99 awt. % and all values and ranges therebetween) rhenium, and 0.1-96 wt. % (and all values and ranges therebetween) of one or more additives selected from the group of aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other components other than the additives (e.g., carbon, oxygen, phosphorous, sulfur, hydrogen, lead, nitrogen, etc.), and which metal alloy exhibits a rhenium effect. In one non-limiting embodiment, the metal alloy that is used to partially or fully form the frame of the prosthetic heart valve is a stainless-steel alloy that has been modified to include at least 15 awt. % rhenium. In another non-limiting embodiment, the metal alloy that is used to partially or fully form the frame of the prosthetic heart valve is a cobalt chromium alloy that has been modified to include at least 15 awt. % rhenium. In another non-limiting embodiment, the metal alloy that is used to partially or fully form the frame of the prosthetic heart valve is a TiAlV alloy that has been modified to include at least 15 awt. % rhenium. In another non-limiting embodiment, the metal alloy that is used to partially or fully form the frame of the prosthetic heart valve is an aluminum alloy that has been modified to include at least 15 awt. % rhenium. In another non-limiting embodiment, the metal alloy that is used to partially or fully form the frame of the prosthetic heart valve is a nickel alloy that has been modified to include at least 15 awt. % rhenium. In another non-limiting embodiment, the metal alloy that is used to partially or fully form the frame of the prosthetic heart valve is a titanium alloy that has been modified to include at least 15 awt. % rhenium. In another non-limiting embodiment, the metal alloy that is used to partially or fully form the frame of the prosthetic heart valve is a tungsten alloy that has been modified to include at least 15 awt. % rhenium. In another non-limiting embodiment, the metal alloy that is used to partially or fully form the frame of the prosthetic heart valve is a molybdenum alloy that has been modified to include at least 15 awt. % rhenium. In another non-limiting embodiment, the metal alloy that is used to partially or fully form the frame of the prosthetic heart valve is a copper alloy that has been modified to include at least 15 awt. % rhenium. In another non-limiting embodiment, the metal alloy that is used to partially or fully form the frame of the prosthetic heart valve is a beryllium-copper alloy that has been modified to include at least 15 awt. % rhenium.

In accordance with another and/or alternative aspect of the present disclosure, the metal alloy that is used to partially or fully form the frame of the prosthetic heart valve includes rhenium and molybdenum, and the weight percent of rhenium in the metal alloy is optionally greater than the weight percent of molybdenum in the metal alloy, and the weight percent of one or more additive (e.g., aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium) in the metal alloy is optionally greater that the weight percent of molybdenum in the metal alloy, and the metal alloy optionally includes 0-2 wt. % of a combination of other components other than the additives (e.g., carbon, oxygen, phosphorous, sulfur, hydrogen, lead, nitrogen, etc.). In one non-limiting embodiment, the metal alloy that is used to partially or fully form the frame of the prosthetic heart valve includes rhenium and molybdenum, and the weight percent of rhenium plus the combined weight percent of additives is greater than the weight percent of molybdenum, and the metal alloy optionally includes 0-2 wt. % of a combination of other components other than the additives (e.g., carbon, oxygen, phosphorous, sulfur, hydrogen, lead, nitrogen, etc.).

In accordance with another and/or alternative aspect of the present disclosure, the metal alloy that is used to partially or fully form the frame of the prosthetic heart valve includes rhenium and molybdenum, and the atomic weight percent of rhenium to the atomic weight percent of the combination of one or more of bismuth, niobium, tantalum, tungsten, titanium, vanadium, chromium, manganese, yttrium, zirconium, technetium, ruthenium, rhodium, hafnium, osmium, copper, and iridium is 0.4:1 to 2.5:1 (and all values and ranges therebetween).

In accordance with another and/or alternative aspect of the present disclosure, the metal alloy that is used to partially or fully form the frame of the prosthetic heart valve includes at least 5 awt. % (e.g., 5-99 awt. % and all values and ranges therebetween) rhenium plus at least two metals selected from the group of molybdenum, bismuth, chromium, iridium, niobium, tantalum, titanium, yttrium, and zirconium, and the content of the metal alloy that includes other elements and compounds is 0-0.1 wt. %. In another non-limiting embodiment, the metal alloy includes rhenium, molybdenum, and chromium. In another non-limiting embodiment, the metal alloy includes at least 35 wt. % (e.g., 35-75 wt. % and all values and ranges therebetween) rhenium, and the metal alloy also includes chromium. In one non-limiting embodiment, the metal alloy includes at least 35 wt. % rhenium and at least 25 wt. % (e.g., 25-49.9 wt. % and all values and ranges therebetween) of the metal alloy includes chromium, and optionally 0.1-40 wt. % (and all values and ranges therebetween) of the metal alloy includes one or more of aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other metals, carbon, oxygen, phosphorous, sulfur, hydrogen and/or nitrogen. In another non-limiting embodiment, the metal alloy includes 15-50 awt. % rhenium (and all values and ranges therebetween) and 0.5-70 awt. % chromium (and all values and ranges therebetween). In another non-limiting embodiment, the metal alloy includes 15-50 awt. % rhenium (and all values and ranges therebetween) and 0.5-70 awt. % tantalum (and all values and ranges therebetween). In another non-limiting embodiment, the metal alloy includes 15-50 awt. % rhenium (and all values and ranges therebetween) and 0.5-70 awt. % niobium (and all values and ranges therebetween). In another non-limiting embodiment, the metal alloy includes 15-50 awt. % rhenium (and all values and ranges therebetween) and 0.5-70 awt. % titanium (and all values and ranges therebetween). In another non-limiting embodiment, the metal alloy includes 15-50 awt. % rhenium (and all values and ranges therebetween) and 0.5-70 awt. % zirconium (and all values and ranges therebetween). In another non-limiting embodiment, the metal alloy includes 15-50 awt. % rhenium (and all values and ranges therebetween) and 0.5-70 awt. % molybdenum (and all values and ranges therebetween). In another non-limiting embodiment, the metal alloy includes at least 15 awt. % rhenium, greater than 50 wt. % titanium (e.g., 51-80 wt. % and all values and ranges therebetween), 15-45 wt. % (and all values and ranges therebetween) niobium, 0-10 wt. % (and all values and ranges therebetween) zirconium, 0-15 wt. % (and all values and ranges therebetween) tantalum, and 0-8 wt. % molybdenum (and all values and ranges therebetween).

In accordance with another and/or alternative aspect of the present disclosure, the metal alloy that is used to partially or fully form the medical device is partially for fully formed of a refractory metal alloy, and wherein the refractory metal alloy includes at least 20 wt. % of one or more of niobium, tantalum or tungsten, and wherein the refractory metal alloy includes 0-30 wt. % molybdenum (and all values and ranges therebetween), and wherein the refractory metal alloy includes at least 5 awt. % rhenium (e.g., 5-80 awt. % rhenium and all values and ranges therebetween).

In accordance with another and/or alternative aspect of the present disclosure, the metal alloy that is used to partially or fully form the medical device is partially for fully formed of a metal alloy includes at least 5 awt. % rhenium (e.g., 5-99 awt. % rhenium and all values and ranges therebetween), and at least 0.1 wt. % of one or more additive metals selected from aluminum, bismuth, chromium, cobalt, copper, hafnium, iridium, iron, magnesium, manganese, nickel, niobium, osmium, rhodium, ruthenium, silicon, silver, tantalum, technetium, titanium, tungsten, vanadium, yttrium, and zirconium, and wherein the metal alloy includes 0-30 wt. % molybdenum (and all values and ranges therebetween), and wherein a combined weight percent of rhenium and the additive metals is 70-100 wt. % (and all values and ranges therebetween).

In accordance with another and/or alternative aspect of the present disclosure, the metal alloy that is used to partially or fully form the medical device is partially for fully formed of a metal alloy of stainless steel that has been modified with at least 5 awt. % rhenium (e.g., 5-50 awt. % rhenium and all values and ranges therebetween), and wherein a combined weight percent of iron, chromium, nickel, tantalum, niobium, copper, manganese, aluminum, titanium, selenium, vanadium, tungsten and rhenium is 70-100 wt. % (and all values and ranges therebetween).

In accordance with another and/or alternative aspect of the present disclosure, the metal alloy that is used to partially or fully form the medical device is partially for fully formed of a metal alloy of cobalt-chromium alloy that has been modified with at least 5 awt. % rhenium (e.g., 5-50 awt. % rhenium and all values and ranges therebetween), and wherein a combined weight percent of cobalt, chromium, nickel, iron, titanium, manganese, silver, tungsten, silicon, aluminum, iron, boron, silver, titanium, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium-aluminum-vanadium alloy that has been modified with at least 5 awt. % rhenium (e.g., 5-50 awt. % rhenium and all values and ranges therebetween), and wherein a combined weight percent of aluminum, vanadium, titanium, iron, yttrium and rhenium is 70-100 wt. % (and all values and ranges therebetween).

In accordance with another and/or alternative aspect of the present disclosure, the metal alloy that is used to partially or fully form the medical device is partially for fully formed of a metal alloy of aluminum alloy that has been modified with at least 5 awt. % rhenium (e.g., 5-50 awt. % rhenium and all values and ranges therebetween), and wherein a combined weight percent of aluminum, silicon, magnesium, manganese, scandium, beryllium, yttrium, cerium, chromium, iron, zinc, titanium, lithium, silver, calcium, zirconium, cadmium, bismuth, nickel, vanadium, gallium, copper, and rhenium is 70-100 wt. % (and all values and ranges therebetween).

In accordance with another and/or alternative aspect of the present disclosure, the metal alloy that is used to partially or fully form the medical device is partially for fully formed of a metal alloy of nickel alloy that has been modified with at least 5 awt. % rhenium (e.g., 5-50 awt. % rhenium and all values and ranges therebetween), and wherein a combined weight percent of nickel, chromium, iron, copper, cobalt, aluminum, tantalum, tungsten, titanium, niobium, silicon, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium alloy that has been modified with at least 5 awt. % rhenium (e.g., 5-50 awt. % rhenium and all values and ranges therebetween), and wherein a combined weight percent of titanium, aluminum, tin, palladium, vanadium, nickel, ruthenium, chromium, zirconium, niobium, silicon, cobalt, iron, and rhenium is 70-100 wt. % (and all values and ranges therebetween).

In accordance with another and/or alternative aspect of the present disclosure, the metal alloy that is used to partially or fully form the medical device is partially for fully formed of a metal alloy of tungsten alloy that has been modified with at least 5 awt. % rhenium (e.g., 5-50 awt. % rhenium and all values and ranges therebetween), and wherein a combined weight percent of tungsten, nickel, copper, iron, and rhenium is 70-100 wt. % (and all values and ranges therebetween).

In accordance with another and/or alternative aspect of the present disclosure, the metal alloy that is used to partially or fully form the medical device is partially for fully formed of a metal alloy of copper alloy that has been modified with at least 5 awt. % rhenium (e.g., 5-50 awt. % rhenium and all values and ranges therebetween), and wherein a combined weight percent of copper, zinc, tin, iron, silicon, manganese, aluminum, beryllium, cobalt, nickel, and rhenium is 70-100 wt. % (and all values and ranges therebetween).

In accordance with another and/or alternative aspect of the present disclosure, the metal alloy that is used to partially or fully form the medical device is partially for fully formed of a metal alloy of beryllium-copper alloy that has been modified with at least 5 awt. % rhenium (e.g., 5-50 awt. % rhenium and all values and ranges therebetween), and wherein a combined weight percent of copper, beryllium, cobalt, silicon, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium-nickel alloy that has been modified with at least 5 awt. % rhenium (e.g., 5-50 awt. % rhenium and all values and ranges therebetween), and wherein a combined weight percent of nickel, titanium, and rhenium is 70-100 wt. % (and all values and ranges therebetween).

In accordance with one non-limiting aspect of the present disclosure, there is provided a medical device in the non-limiting form of a prosthetic heart valve (e.g., TAV valve, mitral valve replacement, tricuspid valve replacement, pulmonary valve replacement) that includes a radially collapsible and expandable frame and a leaflet structure comprising a plurality of leaflets. The prosthetic heart valve can optionally include an annular skirt or cover member disposed on and covering the cells of at least a portion of the frame. The frame can comprise a plurality of interconnected struts defining a plurality of open cells in the frame.

In accordance with another and/or alternative non-limiting aspect of the present disclosure, there is provided a prosthetic heart valve that includes a frame, a leaflet structure supported by the frame, and an optional inner skirt secured to the surface of the frame and/or leaflet structure. The prosthetic heart valve can be implanted in the annulus of the native aortic valve; however, the prosthetic heart valve also can be configured to be implanted in other valves of the heart (e.g., tricuspid valve, pulmonary valve, mitral valve). The prosthetic heart valve has a “lower” end and an “upper” end, wherein the lower end of the prosthetic heart valve is the inflow end and the upper end of the prosthetic heart valve is the outflow end.

In accordance with another and/or alternative non-limiting aspect of the present disclosure, at least a portion of the medical device is configured to be radially collapsible to a collapsed or crimped state for introduction into the body (e.g., on a delivery catheter, etc.) and radially expandable to an expanded state for implanting the medical device at a desired location in the body. The frame of the medical device can be formed of a plastically-expandable material that permits crimping of the frame to a smaller profile for delivery and expansion of the frame. The expansion of the crimped frame of the medical device can be by an expansion device such as, but not limited to, a balloon of on a balloon catheter.

In accordance with another and/or alternative non-limiting aspect of the present disclosure, there is provided a medical device that includes a frame at least partially formed of a plurality of angularly spaced, vertically extending posts, or struts. The posts or struts can optionally be interconnected via a lower row of circumferentially extending struts and an upper row of circumferentially extending struts. The struts can be arrangement in a variety of patterns (e.g., zig-zag pattern, saw-tooth pattern, triangular pattern, polygonal pattern, oval pattern, etc.). One or more of the posts and/or struts can have the same or different thicknesses and/or cross-sectional shape and/or cross-sectional area.

In accordance with another and/or alternative non-limiting aspect of the present disclosure, there is provided a medical device that includes a frame that can be optionally coated with a polymer material (e.g., silicone, PTFE, ePTFE, polyurethane, polyolefins, hydrogels, biological materials (e.g., pericardium or biological polymers such as collagen, gelatin, or hyaluronic acid derivatives), etc.). The coating can be used to partially or fully encapsulate the struts on the frame and/or to fill-in the openings between the struts on the frame.

In accordance with another and/or alternative non-limiting aspect of the present disclosure, there is provided a medical device in the form of a prosthetic heart valve that includes an inner skirt that can be formed of a variety of flexible materials (e.g., polymer [e.g., polyethylene terephthalate (PET), polyester, nylon, Kevlar,®, silicon, etc.], composite material, metal, fabric material, etc.). In one non-limiting embodiment, the material used to partially or fully form the inner skirt can optionally be substantially non-elastic (i.e., substantially non-stretchable and non-compressible). In another non-limiting embodiment, the material used to partially or fully form the inner skirt can optionally be a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). The inner skirt can optionally be formed from a combination of a cloth or fabric material that is coated with a flexible material or with a stretchable and/or compressible material so as to provide additional structural integrity to the inner skirt. The size, configuration, and thickness of the inner skirt is non-limiting (e.g., thickness of 0.1-20 mils and all values and ranges therebetween). The inner skirt can be secured to the inside and/or outside of the frame using various means (e.g., sutures, clamp arrangement, etc.).

In accordance with another and/or alternative non-limiting aspect of the present disclosure, there is provided a medical device in the formed of a prosthetic heart valve that optionally includes an inner skirt that can be used to 1) at least partially seal and/or prevent perivalvular leakage, 2) at least partially secure the leaflet structure to the frame, 3) at least partially protect the leaflets from damage during the crimping and/or expansion process, and/or 4) at least partially protect the leaflets from damage during the operation of the prosthetic heart valve in the heart.

In accordance with another and/or alternative non-limiting aspect of the present disclosure, there is provided a medical device in the form of a prosthetic heart valve that optionally includes an outer or sleeve that is positioned at least partially about the exterior region of the frame. The outer skirt or sleeve generally is positioned completely around a portion of the outside of the frame. Generally, the outer skirt is positioned about the lower portion of the frame, but does not fully cover the upper half of the frame; however, this is not required. The outer skirt can be connected to the frame by a variety of arrangements (e.g., sutures, adhesive, melted connection, clamping arrangement, etc.). At least a portion of the outer skirt can optionally be located on the interior surface of the frame. Generally, the outer skirt is formed of a more flexible and/or compressible material than the inner skirt; however, this is not required. The outer skirt can be formed of a variety of a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). The outer skirt can optionally be formed from a combination of a cloth or fabric material that is coated with the stretchable and/or compressible material to provide additional structural integrity to the outer skirt. The size, configuration, and thickness of the outer skirt is non-limiting. The thickness of the outer skirt is generally 0.1-20 mils (and all values and ranges therebetween).

In accordance with another and/or alternative non-limiting aspect of the present disclosure, there is provided a medical device in the form of a prosthetic heart valve that includes a leaflet structure that can be can be attached to the frame and/or skirt. The connection arrangement used to secure the leaflet structures to the frame and/or skirt is non-limiting (e.g., sutures, melted bold, adhesive, clamp arrangement, etc.). The material used to form the leaflet structures include bovine pericardial tissue, biocompatible synthetic materials, or various other suitable natural or synthetic materials.

In accordance with another and/or alternative non-limiting aspect of the present disclosure, there is provided a medical device in the form of a prosthetic heart valve that includes a leaflet structure comprised of two or more leaflets (e.g., 2, 3, 4, 5, 6, etc.). In one non-limiting arrangement, the leaflet structure includes three leaflets arranged to collapse in a tricuspid arrangement. The configuration of the leaflet structures is non-limiting.

In accordance with another and/or alternative non-limiting aspect of the present disclosure, there is provided a medical device in the form of a prosthetic heart valve that includes a leaflet structure wherein the leaflets of the leaflet structure can optionally be secured to one another at their adjacent sides to form commissures of the leaflet structure (the edges where the leaflets come together). The leaflet structure can be secured together by a variety of connection arrangement (e.g., sutures, adhesive, melted bond, clamping arrangement, etc.).

In accordance with another and/or alternative non-limiting aspect of the present disclosure, there is provided a medical device in the form of a prosthetic heart valve that includes a leaflet structure wherein one or more of the leaflets can optionally include reinforcing structures or strips to 1) facilitate in securing the leaflets together, 2) facilitate in securing the leaflets to the skirt and/or frame, and/or 3) inhibit or prevent tearing or other types of damage to the leaflets.

In accordance with another and/or alternative non-limiting aspect of the present disclosure, the metal alloy that is used to form at least a portion of the medical device optionally has one or more improved properties (e.g., strength, durability, hardness, biostability, bendability, coefficient of friction, radial strength, flexibility, tensile strength, tensile elongation, longitudinal lengthening, stress-strain properties, reduced recoil, radiopacity, heat sensitivity, biocompatibility, improved fatigue life, crack resistance, crack propagation resistance, reduced magnetic susceptibility, etc.), improved conformity when bent, less recoil, increase yield strength, improved fatigue ductility, improved durability, improved fatigue life, reduced adverse tissue reactions, reduced metal ion release, reduced corrosion, reduced allergic reaction, improved hydrophilicity, reduced toxicity, reduced thickness of metal component, improved bone fusion, and/or lower ion release into tissue. These one or more improved physical properties of the metal alloy can be achieved in the medical device or portion of the medical device (e.g., frame of the medical device, etc.) without having to increase the bulk, volume, and/or weight of the medical device or portion of the medical device (e.g., frame of the medical device, etc.), and in some instances these improved physical properties can be obtained even when the volume, bulk, and/or weight of the medical device or portion of the medical device (e.g., frame of the medical device, etc.) is reduced as compared to medical devices or the frame of the medical device that are at least partially formed from traditional stainless steel, titanium alloy, or cobalt and chromium alloy materials.

In accordance with another and/or alternative non-limiting aspect of the present disclosure, the metal alloy used to at least partially form the medical device or portion of the medical device (e.g., frame of the medical device, etc.) can optionally 1) increase the radiopacity of the medical device or portion of the medical device (e.g., frame of the medical device, etc.), 2) increase the radial strength of the medical device or portion of the medical device (e.g., frame of the medical device, etc.), 3) increase the yield strength and/or ultimate tensile strength of the medical device or portion of the medical device (e.g., frame of the medical device, etc.), 4) improve the stress-strain properties of the medical device or portion of the medical device (e.g., frame of the medical device, etc.), 5) improve the crimping and/or expansion properties of the medical device or portion of the medical device (e.g., frame of the medical device, etc.), 6) improve the bendability and/or flexibility of the medical device or portion of the medical device (e.g., frame of the medical device, etc.), 7) improve the strength and/or durability of the medical device or portion of the medical device (e.g., frame of the medical device, etc.), 8) increase the hardness of the medical device or portion of the medical device (e.g., frame of the medical device, etc.), 9) improve the recoil properties of the medical device or portion of the medical device (e.g., frame of the medical device, etc.), 10) improve the biostability and/or biocompatibility properties of the medical device or portion of the medical device (e.g., frame of the medical device, etc.), 11) increase fatigue resistance of the medical device or portion of the medical device (e.g., frame of the medical device, etc.), 12) resist cracking in the medical device or portion of the medical device (e.g., frame of the medical device, etc.) and resist propagation of cracks, 13) enable smaller, thinner, and/or lighter weight medical device or portion of the medical device (e.g., frame of the medical device, etc.) to be made, 14) reduce the outer diameter of a crimped medical device or portion of the medical device (e.g., frame of the medical device, etc.), 15) improve the conformity of the medical device or portion of the medical device (e.g., frame of the medical device, etc.) to the shape of the treatment area when the medical device or portion of the medical device (e.g., frame of the medical device, etc.) is used and/or expanded in the treatment area, 16) reduce the amount of recoil of the medical device or portion of the medical device (e.g., frame of the medical device, etc.) to the shape of the treatment area when the medical device or portion of the medical device (e.g., frame of the medical device, etc.) is expanded in the treatment area, 17) increase yield strength of the medical device or portion of the medical device (e.g., frame of the medical device, etc.), 18) improve fatigue ductility of the medical device or portion of the medical device (e.g., frame of the medical device, etc.), 18) improve durability of the medical device or portion of the medical device (e.g., frame of the medical device, etc.), 19) improve fatigue life of the medical device or portion of the medical device (e.g., frame of the medical device, etc.), 20) reduce adverse tissue reactions after implant of the medical device or portion of the medical device (e.g., frame of the medical device, etc.), 21) reduce metal ion release after implant of the medical device or portion of the medical device (e.g., frame of the medical device, etc.), 22) reduce corrosion of the medical device or portion of the medical device (e.g., frame of the medical device, etc.) after implant of the medical device or portion of the medical device (e.g., frame of the medical device, etc.), 23) reduce allergic reaction after implant of the medical device or portion of the medical device (e.g., frame of the medical device, etc.), 24) improve hydrophilicity of the medical device or portion of the medical device (e.g., frame of the medical device, etc.), 25) reduce thickness of meta component of medical device or portion of the medical device (e.g., frame of the medical device, etc.), 26) improve bone fusion with medical device or portion of the medical device (e.g., frame of the medical device, etc.), and/or 27) lower ion release from medical device or portion of the medical device (e.g., frame of the medical device, etc.) into tissue, 28) reduce magnetic susceptibility of the medical device or portion of the medical device (e.g., frame of the medical device, etc.) when implanted in a patient, and/or 29) reduce toxicity of the medical device or portion of the medical device (e.g., frame of the medical device, etc.) after implant of the prosthetic medical device.

In accordance with another and/or alternative non-limiting aspect of the present disclosure, the use of the metal alloy to partially or fully form the frame of the prosthetic heart valve can be used to optionally increase the strength, hardness, and/or durability of the medical device or portion of the medical device (e.g., frame of the medical device, etc.) compared with stainless steel, chromium-cobalt alloys, or titanium alloys; thus, a lesser quantity of metal alloy can be used in the medical device or portion of the medical device (e.g., frame of the medical device, etc.) to achieve similar strengths compared to medical devices or frames of medical devices formed of different metals. As such, the resulting medical device can be made smaller and less bulky by use of the metal alloy without sacrificing the strength and durability of the medical device. Such a medical device can have a smaller profile, thus can be inserted in smaller areas, openings, and/or passageways. The metal alloy also can increase the radial strength of the medical device. For example, the thickness of the walls of the medical device or portion of the medical device (e.g., frame of the medical device, etc.) and/or the wires used to at least partially form the medical device or portion of the medical device (e.g., frame of the medical device, etc.) can be made thinner and achieve a similar or improved radial strength as compared with thicker walled medical devices formed of stainless steel, titanium alloys, or cobalt and chromium alloys. The metal alloy also can improve stress-strain properties, bendability, and flexibility of the medical device, thus increasing the life of the medical device. For example, the medical device can be used in regions that subject the medical device to bending. Due to the improved physical properties of the medical device from the metal alloy, the medical device has improved resistance to fracturing in such frequent bending environments. In addition or alternatively, the improved bendability and flexibility of the medical device due to the use of the metal alloy enables the medical device to be more easily inserted into various regions of a body. The metal alloy can also reduce the degree of recoil during the crimping and/or expansion of the medical device. For example, the medical device better maintains its crimped form and/or better maintains its expanded form after expansion due to the use of the metal alloy. As such, when the medical device is to be mounted onto a delivery device when the medical device is crimped, the medical device better maintains its smaller profile during the insertion of the medical device into various regions of a body. Also, the medical device better maintains its expanded profile after expansion to facilitate in the success of the medical device in the treatment area. In addition to the improved physical properties of the medical device by use of the metal alloy, the metal alloy has improved radiopaque properties as compared to standard materials such as stainless steel or cobalt-chromium alloy, thus reducing or eliminating the need for using marker materials on the medical device. For instance, the metal alloy is believed to at least about 10-20% more radiopaque than stainless steel or cobalt-chromium alloy.

In accordance with another and/or alternative non-limiting aspect of the present disclosure, the medical device can include, contain and/or be coated with one or more agents that facilitate in the success of the medical device and/or treated area. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to, viral, fungus and/or bacterial infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; nerve repair; neural regeneration and/or the like. The type and/or amount of agent included in medical device and/or coated on medical device can vary. When two or more agents are included in and/or coated on medical device, the amount of two or more agents can be the same or different. The type and/or amount of agent included on, in and/or in conjunction with medical device are generally selected to address one or more clinical events.

In accordance with another and/or alternative non-limiting aspect of the present disclosure, the amount of agent included on, in and/or used in conjunction with medical device, when the agent is used, is about 0.01-100 μg per mm2 (and all values and ranges wherein between) and/or at least about 0.00001 wt. % of device; however, other amounts can be used. The amount of two of more agents on, in and/or used in conjunction with medical device can be the same or different. The one or more agents can be coated on and/or impregnated in medical device by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition. The amount of two of more agents on, in and/or used in conjunction with medical device, when two one more agents are used, can be the same or different.

In accordance with another and/or alternative non-limiting aspect of the present disclosure, the one or more agents on and/or in the medical device, when used on the medical device, can be released in a controlled manner so the area in question to be treated is provided with the desired dosage of agent over a sustained period of time. As can be appreciated, controlled release of one or more agents on the medical device is not always required and/or desirable. As such, one or more of the agents on and/or in the medical device can be uncontrollably released from the medical device during and/or after insertion of the medical device in the treatment area. It can also be appreciated that one or more agents on and/or in the medical device can be controllably released from the medical device and one or more agents on and/or in the medical device can be uncontrollably released from the medical device. It can also be appreciated that one or more agents on and/or in one region of the medical device can be controllably released from the medical device and one or more agents on and/or in the medical device can be uncontrollably released from another region on the medical device. As such, the medical device can be designed such that 1) all the agent on and/or in the medical device is controllably released, 2) some of the agent on and/or in the medical device is controllably released and some of the agent on the medical device is non-controllably released, or 3) none of the agent on and/or in the medical device is controllably released. The medical device can also be designed such that the rate of release of the one or more agents from the medical device is the same or different. The medical device can also be designed such that the rate of release of the one or more agents from one or more regions on the medical device is the same or different. Non-limiting arrangements that can be used to control the release of one or more agents from the medical device include 1) at least partially coat one or more agents with one or more polymers, 2) at least partially incorporate and/or at least partially encapsulate one or more agents into and/or with one or more polymers, and/or 3) insert one or more agents in pores, passageway, cavities, etc. in the medical device and at least partially coat or cover such pores, passageway, cavities, etc. with one or more polymers. As can be appreciated, other or additional arrangements can be used to control the release of one or more agents from the medical device.

In accordance with another and/or alternative non-limiting aspect of the present disclosure, the one or more polymers used to at least partially control the release of one or more agents from the medical device can be porous or non-porous. The one or more agents can be inserted into and/or applied to one or more surface structures and/or micro-structures on the medical device, and/or be used to at least partially form one or more surface structures and/or micro-structures on the medical device. As such, the one or more agents on the medical device can be 1) coated on one or more surface regions of the medical device, 2) inserted and/or impregnated in one or more surface structures and/or micro-structures, etc. of the medical device, and/or 3) form at least a portion or be included in at least a portion of the structure of the medical device. When the one or more agents are coated on the medical device, the one or more agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. When the one or more agents are inserted and/or impregnated in one or more internal structures, surface structures and/or micro-structures of the medical device, 1) one or more other coating materials can be applied at least partially over the one or more internal structures, surface structures and/or micro-structures of the medical device, and/or 2) one or more polymers can be combined with one or more agents. As such, the one or more agents can be 1) embedded in the structure of the medical device; 2) positioned in one or more internal structures of the medical device; 3) encapsulated between two polymer coatings; 4) encapsulated between the base structure and a polymer coating; and/or 5) mixed in the base structure of the medical device that includes at least one polymer coating. In addition or alternatively, the one or more coating of the one or more polymers on the medical device can include 1) one or more coatings of non-porous polymers; 2) one or more coatings of a combination of one or more porous polymers and one or more non-porous polymers; and/or 3) one or more coating of porous polymer.

In accordance with another and/or alternative non-limiting aspect of the present disclosure, different agents can optionally be located in and/or between different polymer coating layers and/or on and/or the structure of the medical device. As can also be appreciated, many other and/or additional coating combinations and/or configurations can be used. The concentration of one or more agents, the type of polymer, the type and/or shape of internal structures in the medical device and/or the coating thickness of one or more agents can be used to control the release time, the release rate and/or the dosage amount of one or more agents; however, other or additional combinations can be used. As such, the agent and polymer system combination and location on the medical device can be numerous. As can also be appreciated, one or more agents can be deposited on the top surface of the medical device to provide an initial uncontrolled burst effect of the one or more agents prior to 1) the controlled release of the one or more agents through one or more layers of a polymer system that include one or more non-porous polymers and/or 2) the uncontrolled release of the one or more agents through one or more layers of a polymer system. The one or more agents and/or polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition.

In accordance with another and/or alternative non-limiting aspect of the present disclosure, the thickness of each polymer layer and/or layer of agent is generally at least about 0.01 μm and is generally less than about 150 μm (e.g., 0.01-149.9999 μm and all values and ranges therebetween). In one non-limiting embodiment, the thickness of a polymer layer and/or layer of agent is about 0.02-75 μm, more particularly about 0.05-50 μm, and even more particularly about 1-30 μm. As can be appreciated, other thicknesses can be used.

In accordance with another and/or alternative non-limiting aspect of the present disclosure, a variety of polymers can be coated on the medical device and/or be used to form at least a portion of the medical device. When one or more layers of polymer are coated onto at least a portion of the medical device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers that can be coated on the medical device and/or used to at least partially form the medical device can be polymers that are considered to be biodegradable, bioresorbable, or bioerodable; polymers that are considered to be biostable; and/or polymers that can be made to be biodegradable and/or bioresorbable with modification. The one or more polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition.

In accordance with another and/or alternative non-limiting aspect of the present disclosure, the medical device, when including and/or is coated with one or more agents, can include and/or can be coated with one or more agents that are the same or different in different regions of the medical device and/or have differing amounts and/or concentrations in differing regions of the medical device. For instance, the medical device can be 1) coated with and/or include one or more biologicals on at least one portion of the medical device and at least another portion of the medical device is not coated with and/or includes agent, 2) coated with and/or include one or more biologicals on at least one portion of the medical device that is different from one or more biologicals on at least another portion of the medical device, and/or 3) coated with and/or include one or more biologicals at a concentration on at least one portion of the medical device that is different from the concentration of one or more biologicals on at least another portion of the medical device; etc.

In accordance with another and/or alternative non-limiting aspect of the present disclosure, one or more portions of the medical device can optionally 1) include the same or different agents, 2) include the same or different amount of one or more agents, 3) include the same or different polymer coatings, 4) include the same or different coating thicknesses of one or more polymer coatings, 5) have one or more portions of the medical device controllably release and/or uncontrollably release one or more agents, and/or 6) have one or more portions of the medical device controllably release one or more agents and one or more portions of the medical device uncontrollably release one or more agents.

In accordance with another and/or alternative non-limiting aspect of the present disclosure, one or more surfaces of the medical device can optionally be treated to achieve the desired coating properties of the one or more agents and one or more polymers coated on the medical device. Such surface treatment techniques include, but are not limited to, cleaning, buffing, smoothing, nitriding, annealing, swaging, cold working, etching (chemical etching, plasma etching, etc.), etc. As can be appreciated, other or additional surface treatment processes can be used prior to the coating of one or more agents and/or polymers on the surface of the medical device. Once one or more surface regions of the medical device been treated, one or more coatings of polymer and/or agent can be applied to one or more regions of the medical device. The one or more layers of agent can be applied to the medical device by a variety of techniques (e.g., dipping, rolling, brushing, spraying, particle atomization, etc.). One non-limiting coating technique is by an ultrasonic mist coating process wherein ultrasonic waves are used to break up the droplet of agent and form a mist of very fine droplets. These fine droplets have an average droplet diameter of about 0.1-3 microns. The fine droplet mist facilitates in the formation of a uniform coating thickness and can increase the coverage area on the medical device.

In accordance with another and/or alternative non-limiting aspect of the present disclosure, the medical device can optionally include a marker material that facilitates enabling the medical device to be properly positioned in a body passageway (e.g., blood vessel, heart valve, etc.). The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion, at ends of medical device, at or near transition of body portion and flaring section, etc.) of the medical device. The location of the marker material can be on one or multiple locations on the medical device. The size of the one or more regions including the marker material can be the same or different. The marker material can be spaced at defined distances from one another to form ruler-like markings on the medical device to facilitate in the positioning of the medical device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. The metal, which at least partially forms the medical device, can function as a marker material; however, this is not required. When the marker material is a flexible material, the marker material typically is formed of one or more polymers that are marker materials in-of-themselves and/or include one or more metal powders and/or metal compounds.

In accordance with another and/or alternative non-limiting aspect of the present disclosure, the medical device or one or more regions of the medical device can optionally be constructed by use of one or more microelectromechanical manufacturing (MEMS) techniques (e.g., micro-machining, laser micro-machining, laser micro-machining, micro-molding, 3D printing, etc.); however, other or additional manufacturing techniques can be used.

In accordance with another and/or alternative non-limiting aspect of the present disclosure, the medical device can optionally include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology (e.g., 3D printing, etc.).

In accordance with another and/or alternative non-limiting aspect of the present disclosure, the medical device can optionally include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie-like structure, etc.) on the surface of the medical device. As defined herein, a "micro-structure" is a structure having at least one dimension (e.g., average width, average diameter, average height, average length, average depth, etc.) that is no more than about 2 mm, and typically no more than about 1 mm. As can be appreciated, when the medical device includes one or more surface structures, 1) all the surface structures can be micro-structures, 2) all the surface structures can be non-micro-structures, or 3) a portion of the surface structures can be micro-structures and a portion can be non-micro-structures. Non-limiting examples of structures that can be formed on the medical device are illustrated in United States Patent Publication Nos. 2004/0093076 and 2004/0093077, which are incorporated herein by reference. Typically, the micro-structures (when formed) extend from or into the outer surface no more than about 400 microns (0.01-400 microns and all values and ranges therebetween), and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and/or be designed to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has been positioned on and/or in a patient; however, this is not required. The one or more surface structures and/or micro-structures can be used to facilitate in forming maintaining a shape of a medical device. In one non-limiting embodiment, the one or more surface structures and/or micro-structures can be at least partially formed of an agent and/or be formed of a polymer. One or more of the surface structures and/or micro-structures can include one or more internal passageways that can include one or more materials (e.g., agent, polymer, etc.); however, this is not required. The one or more surface structures and/or micro-structures can be formed by a variety of processes (e.g., machining, chemical modifications, chemical reactions, MEMS (e.g., micro-machining, etc.), etching, laser cutting, 3D printing, photo-etching, etc.). The one or more coatings and/or one or more surface structures and/or micro-structures of the medical device can be used for a variety of purposes such as, but not limited to, 1) increasing the bonding and/or adhesion of one or more agents, adhesives, marker materials and/or polymers to the medical device, 2) changing the appearance or surface characteristics of the medical device, and/or 3) controlling the release rate of one or more agents. The one or more micro-structures and/or surface structures can be biostable, biodegradable, etc. One or more regions of the medical device that are at least partially formed by MEMS techniques can be biostable, biodegradable, etc. The medical device or one or more regions of the medical device can be at least partially covered and/or filled with a protective material to at least partially protect one or more regions of the medical device, and/or one or more micro-structures and/or surface structures on the medical device from damage. One or more regions of the medical device, and/or one or more micro-structures and/or surface structures on the medical device can be damaged when the medical device is 1) packaged and/or stored, 2) unpackaged, 3) connected to and/or other secured and/or placed on another medical device, 4) inserted into a treatment area, and/or 5) handled by a user. As can be appreciated, the medical device can be damaged in other or additional ways. The protective material can be used to protect the medical device and/or one or more micro-structures and/or surface structures from such damage. The protective material can include one or more polymers previously identified above. The protective material can be 1) biostable and/or biodegradable and/or 2) porous and/or non-porous. In another and/or additional non-limiting design, the protective material includes, but is not limited to, sugar (e.g., glucose, fructose, sucrose, etc.), carbohydrate compound, salt (e.g., NaCl, etc.), parylene, PLGA, POE, PGA, PLLA, PAA, PEG, chitosan and/or derivatives of one or more of these materials; however, other and/or additional materials can be used. In still another and/or additional non-limiting design, the thickness of the protective material is generally less than about 300 microns (e.g., 0.01 microns to 299.9999 microns and all values and ranges therebetween), and typically less than about 150 microns; however, other thicknesses can be used. The protective material can be coated by one or more mechanisms previously described herein.

In accordance with another and/or alternative non-limiting aspect of the present disclosure, the medical device can optionally be an expandable device that can be expanded by use of some other device (e.g., balloon, etc.).

In accordance with another and/or alternative non-limiting aspect of the present disclosure, the medical device can optionally be fabricated from a material having no or substantially no shape-memory characteristics.

In accordance with another and/or alternative non-limiting aspect of the present disclosure, there is provided a prosthetic heart valve that is configured to be inserted into a desired location in the body (e.g., the aortic valve, tricuspid valve, pulmonary valve, mitral valve). The frame of the prosthetic heart valve can be at least partially formed of a plastically-expandable material that permits crimping of the frame to a smaller profile for delivery and expansion of the prosthetic heart valve to a larger profile. The expansion of the crimped frame can be optionally be use of an expansion device such as, but not limited to, a balloon of on a balloon catheter. As can be appreciated, the medical device can be a device other than a prosthetic heart valve (e.g., stent, etc.) that includes a frame that is at least partially formed of a plastically expandable material that permits crimping of the frame to a smaller profile for delivery and expansion of the medical device to a larger profile.

One non-limiting object of the present disclosure is the provision of a device and method for crimping a crimpable or plastically deformable portion of a medical device.

Another and/or alternative non-limiting object of the present disclosure is the provision of a device and method for crimping a crimpable or plastically deformable portion of a medical device that includes one or more leaflets.

Another and/or alternative non-limiting object of the present disclosure is the provision of a device and method for crimping a crimpable or plastically deformable portion of a medical device that includes one or more leaflets so as to reduce void spaces about the leaflets after completion of the crimping of the crimpable or plastically deformable portion of a medical device.

Another and/or alternative non-limiting object of the present disclosure is the provision of a device and method for crimping a crimpable or plastically deformable portion of a medical device that includes one or more leaflets so as to obtains a desired folding profile of the leaflets after completion of the crimping of the crimpable or plastically deformable portion of a medical device.

Another and/or alternative non-limiting object of the present disclosure is the provision of a device and method for crimping a crimpable or plastically deformable portion of a medical device that includes one or more leaflets so as to facilitate in the desired folding profile of the leaflets of a prosthetic heart valve during the crimping of the frame of the prosthetic heart valve to reduce the number and volume of void spaces between and about the leaflets and to reduce the crimped outer diameter profile of the prosthetic heat valve, while reducing the risk of damage to the leaflets and other components of the prosthetic heart valve during the crimping process.

Another and/or alternative non-limiting object of the present disclosure is the provision of a device and method for crimping a crimpable or plastically deformable portion of a medical device that includes one or more leaflets so as to reduce the outer diameter or cross-sectional area of the portion of the crimpable or plastically deformable portion of a medical device that includes the leaflets.

Another and/or alternative non-limiting object of the present disclosure is the provision of a method for reducing the profile of a frame of a medical device comprising a) providing a medical device that includes a crimpable or plastically deformable portion; b) providing a crimping device; the crimping device includes a crimping assembly having a device opening; the device opening is configured to receive at least a portion of the medical device; the device opening is configured to reduce in diameter or cross-sectional area during operation of the crimping device; c) inserting at least a portion of the crimpable or plastically deformable portion of the medical device into the device opening; and d) operating the medical device to cause at least a portion of the device opening to reduce in diameter or cross-sectional area to thereby exert a crimping force initially on only a first portion of the crimpable or plastically deformable portion of the medical device which causes the first portion of the crimpable or plastically deformable portion of the medical device to reduce in cross-sectional area, and thereafter continuing to use the crimping device to subsequently exert a crimping force on a second portion of the crimpable or plastically deformable portion of the medical device which causes the second portion of the crimpable or plastically deformable portion of the medical device to reduce in cross-sectional area.

Another and/or alternative non-limiting object of the present disclosure is the provision of a method for reducing the profile of a frame of a medical device wherein the crimping device is configured to continue to exert the crimping force on both the first and second portions of the crimpable or plastically deformable portion of the medical device after initially exerting the crimping force on the second portion so as to further reduce the diameter or cross-sectional area of both the first and second portions of the crimpable or plastically deformable portion of the medical device.

Another and/or alternative non-limiting object of the present disclosure is the provision of a method for reducing the profile of a frame of a medical device wherein the crimping device is configured to exert the crimping force on the first portion until the diameter or cross-sectional area of the first portion of the crimpable or plastically deformable portion of the medical device is reduced by at least 1% prior to the crimping device initially exerting the crimping force on the second portion of the crimpable or plastically deformable portion of the medical device.

Another and/or alternative non-limiting object of the present disclosure is the provision of a method for reducing the profile of a frame of a medical device wherein the crimping device is configured to exert the crimping force on the first portion until the diameter or cross-sectional area of the first portion of the crimpable or plastically deformable portion of the medical device is reduced by at least 5% prior to the crimping device initially exerting the crimping force on the second portion of the crimpable or plastically deformable portion of the medical device.

Another and/or alternative non-limiting object of the present disclosure is the provision of a method for reducing the profile of a frame of a medical device wherein the crimping device is configured to exert the crimping force on the first portion until the diameter or cross-sectional area of the first portion of the crimpable or plastically deformable portion of the medical device is reduced by at least 25% prior to the crimping device initially exerting the crimping force on the second portion of the crimpable or plastically deformable portion of the medical device.

Another and/or alternative non-limiting object of the present disclosure is the provision of a method for reducing the profile of a frame of a medical device wherein the crimping device is configured to exert the crimping force on the first portion until the diameter or cross-sectional area of the first portion of the crimpable or plastically deformable portion of the medical device is reduced by at least 50% prior to the crimping device initially exerting the crimping force on the second portion of the crimpable or plastically deformable portion of the medical device.

Another and/or alternative non-limiting object of the present disclosure is the provision of a method for reducing the profile of a frame of a medical device wherein the first and second portion of the crimpable or plastically deformable portion of the medical device are both simultaneously positioned in the device opening during reduction of the diameter or cross-sectional area of the first and second portions of the crimpable or plastically deformable portion of the medical device by the crimper device.

Another and/or alternative non-limiting object of the present disclosure is the provision of a method for reducing the profile of a frame of a medical device wherein the first portion of the crimpable or plastically deformable portion of the medical device includes an inflow end portion of the medical device.

Another and/or alternative non-limiting object of the present disclosure is the provision of a method for reducing the profile of a frame of a medical device wherein the second portion of the crimpable or plastically deformable portion of the medical device includes an outflow end portion of the medical device.

Another and/or alternative non-limiting object of the present disclosure is the provision of a method for reducing the profile of a frame of a medical device wherein the medical device includes one or more leaflets that are connected to the crimpable or plastically deformable portion of the medical device.

Another and/or alternative non-limiting object of the present disclosure is the provision of a method for reducing the profile of a frame of a medical device wherein the medical device is a prosthetic heart valve; the crimpable or plastically deformable portion of the medical device includes a frame of the prosthetic heart valve; the one or more leaflets are connected to the frame.

Another and/or alternative non-limiting object of the present disclosure is the provision of a method for reducing the profile of a frame of a medical device further including the step of causing at least a portion of one or more of the leaflets to be bent toward a central longitudinal axis of the crimpable or plastically deformable portion of the medical device a) prior to applying the crimping force on the crimpable or plastically deformable portion of the medical device, and/or b) while applying the crimping force to the crimping of the crimpable or plastically deformable portion of the medical device.

Another and/or alternative non-limiting object of the present disclosure is the provision of a method for reducing the profile of a frame of a medical device further includes the step of applying a rotational force about a central longitudinal axis of the crimpable or plastically deformable portion to one or more of the leaflets a) prior to applying the crimping force on the crimpable or plastically deformable portion of the medical device, and/or b) while applying the crimping force to the crimping of the crimpable or plastically deformable portion of the medical device.

Another and/or alternative non-limiting object of the present disclosure is the provision of a method for reducing the profile of a frame of a medical device further providing a leaflet folding device that is configured to facilitate in folding the one or more of the leaflets during the step of applying the crimping force on the crimpable or plastically deformable portion of the medical device.

Another and/or alternative non-limiting object of the present disclosure is the provision of a method for reducing the profile of a frame of a medical device further providing a leaflet folding device that is configured to facilitate in folding the one or more of the leaflets during the step of applying the crimping force on the crimpable or plastically deformable portion of the medical device, wherein the leaflet folding device is positioned within the leaflets such that the leaflets are positioned between the frame of the prosthetic heat valve and the leaflet folding device.

Another and/or alternative non-limiting object of the present disclosure is the provision of a method for reducing the profile of a frame of a medical device further providing a leaflet folding device that is configured to facilitate in folding the one or more of the leaflets during the step of applying the crimping force on the crimpable or plastically deformable portion of the medical device, wherein the leaflet folding device is positioned within the leaflets such that the leaflets are positioned between the frame of the prosthetic heat valve and the leaflet folding device, and wherein the leaflet folding device includes a) a hollow, collapsible body portion that is configured to be inserted into the prosthetic heart valve during the crimping process, b) one or more arms that radially extend from the body portion of the leaflet folding device, c) a hollow, collapsible body portion that is configured to be inserted into the prosthetic heart valve during the crimping process, and which includes one or more arms that are collapsible and that radially extend from the body portion of the leaflet folding device, d) a hollow, collapsible body portion that is configured to be inserted into the prosthetic heart valve during the crimping process, and which includes one or more arms that are collapsible and that radially extend from the body portion of the leaflet folding device, c) a non-collapsible body portion and one or more non-collapsible arms that radially extend from the body portion of the leaflet folding device, or f) a body portion that includes two or more prongs that are configured to engage a portion of two or more leaflets.

Another and/or alternative non-limiting object of the present disclosure is the provision of a method for reducing the profile of a frame of a medical device further including the step of positioning at least a portion of the leaflet folding device between the one or more leaflets and the crimpable or plastically deformable portion of the medical device to facilitate in a) bending at least a portion of one or more of the leaflets toward the central longitudinal axis of the crimpable or plastically deformable portion, and/or b) rotating at least a portion of one or more of the leaflets about the central longitudinal axis of the crimpable or plastically deformable portion.

Another and/or alternative non-limiting object of the present disclosure is the provision of a method for reducing the profile of a frame of a medical device further includes the step of fully disengaging the leaflet folding device from one or more of the leaflets prior to completion of applying the crimping force on the crimpable or plastically deformable portion of the medical device.

Another and/or alternative non-limiting object of the present disclosure is the provision of a method for reducing the profile of a frame of a medical device wherein the leaflet folding device includes a handle portion and one or more leaflet engagement members that are attached to and extend from the handle portion; the one or more leaflet engagement members are at least partially formed of a flexible material that enables the one or more leaflet engagement members to flex and/or bend a) when positioning the one or more leaflet engagement members about one or more leaflets, and/or b) as the crimpable or plastically deformable portion of the medical device reduces in diameter or cross-sectional area as the crimping force is applied on the crimpable or plastically deformable portion of the medical device.

Another and/or alternative non-limiting object of the present disclosure is the provision of a method for reducing the profile of a frame of a medical device wherein the one or more leaflet engagement members include a wire loop.

Another and/or alternative non-limiting object of the present disclosure is the provision of a method for reducing the profile of a frame of a medical device further including the step of positioning a portion or one or more of the leaflet engagement members between a portion of one or more of the leaflets and the crimpable or plastically deformable portion of the medical device to cause at least a portion of the one or more of the leaflets to bend towards the central longitudinal axis of the crimpable or plastically deformable portion of the medical device.

Another and/or alternative non-limiting object of the present disclosure is the provision of a crimper device that is configured to crimp a crimpable or plastically deformable portion of a medical device; the crimping device includes a crimping assembly having a device opening; the device opening is configured to receive at least a portion of the medical device; the device opening is configured to reduce in diameter or cross-sectional area during operation of the crimping device; a first portion of the device opening is configured to a) reduce in diameter or cross-sectional area at a different rate as compared to a second portion of the device opening during the operation of the crimping device, and/or b) begin reducing in diameter or cross-sectional area at a different time as compared to a second portion of the device opening during the operation of the crimping device.

Another and/or alternative non-limiting object of the present disclosure is the provision of a method for reducing the outer diameter of a crimped prosthetic heart valve comprising a) providing a prosthetic heart valve; the prosthetic heart valve includes a frame, a leaflet structure supported by the frame; the frame in a non-fully crimped state; b) providing a diameter reducing device that is configured to reduce an outer diameter of the prosthetic heart valve; c) at least partially inserting the prosthetic heart valve in the diameter reducing device; and d) initially reducing an outer diameter of the prosthetic heart valve by use of the diameter reducing device; and wherein the step of reducing includes applying a crimping force on the frame of the prosthetic heart valve along the longitudinal length of the prosthetic heart valve; and wherein the step of reducing includes A) gradual application of the crimping force in a continuously progressive manner along a longitudinal length of the frame by i) initially applying the crimping force at an inflow end of the frame and subsequently applying the crimping force at locations that are spaced from the inflow end of the frame until the crimping force is applied to a complete outer surface of the frame; or ii) initially applying the crimping force at an outflow end of the frame and subsequently applying the crimping force at locations that are spaced from the outflow end of the flame until the crimping force is applied to a complete outer surface of the frame; or B) stepwise application of the crimping force along a longitudinal length of the frame by i) initially applying the crimping force at an inflow region of the frame until a portion or all of the inflow region of the frame is crimped to 10-100% (and all values and ranges therebetween) of a fully crimped diameter or cross-sectional area, and then subsequently applying the crimping force at one or more locations that are spaced from the inflow region of the frame to crimped the one or more locations that are spaced from the inflow region of the frame to 10-100% (and all values and ranges therebetween) of a fully crimped diameter or cross-sectional area, and wherein the inflow region of the frame extends from an inflow end of the frame to 0.1-75% (and all values and ranges therebetween) of a longitudinal length of the frame; or ii) initially applying the crimping force at an outflow side of the frame until a portion or all of a outflow region of the frame is crimped to 10-100% (and all values and ranges therebetween) of a fully crimped diameter or cross-sectional area, and then subsequently applying the crimping force at one or more locations that are spaced from the outflow region of the frame to crimped the one or more locations that are spaced from the outflow region of the frame to 10-100% (and all values and ranges therebetween) of a fully crimped diameter or cross-sectional area, and wherein the outflow region of the frame extends from an outflow end of the frame to 0.1-75% (and all values and ranges therebetween) of a longitudinal length of the frame.

Another and/or alternative non-limiting object of the present disclosure is the provision of a method for reducing the profile of a frame of a medical device; the method comprising a) providing a medical device that includes a crimpable or plastically deformable portion; b) providing a crimping device; the crimping device includes a crimping assembly having a device opening; the device opening is configured to receive at least a portion of the medical device; the device opening is configured to reduce in diameter or cross-sectional area during operation of the crimping device; c) inserting at least a portion of the crimpable or plastically deformable portion of the medical device into the device opening; and d) operating the medical device to cause at least a portion of the device opening to reduce in diameter or cross-sectional area to thereby exert a crimping force initially on only a first portion of the crimpable or plastically deformable portion of the medical device which causes the first portion of the crimpable or plastically deformable portion of the medical device to reduce in cross-sectional area, and thereafter continuing to use the crimping device to subsequently exert a crimping force on a second portion of the crimpable or plastically deformable portion of the medical device which causes the second portion of the crimpable or plastically deformable portion of the medical device to reduce in cross-sectional area; the first portion of the crimpable or plastically deformable portion of the medical device constitutes 0.01%-75% of a longitudinal length of the crimpable or plastically deformable portion of the medical device.

These and other advantages will become apparent to those skilled in the art upon the reading and following of this description.

BRIEF DESCRIPTION OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for case of recognition in the drawings. Reference may now be made to the drawings, which illustrate various embodiments that the disclosure may take in physical form and in certain parts and arrangement of parts wherein.

DESCRIPTION OF NON-LIMITING EMBODIMENTS

Figure 1B:
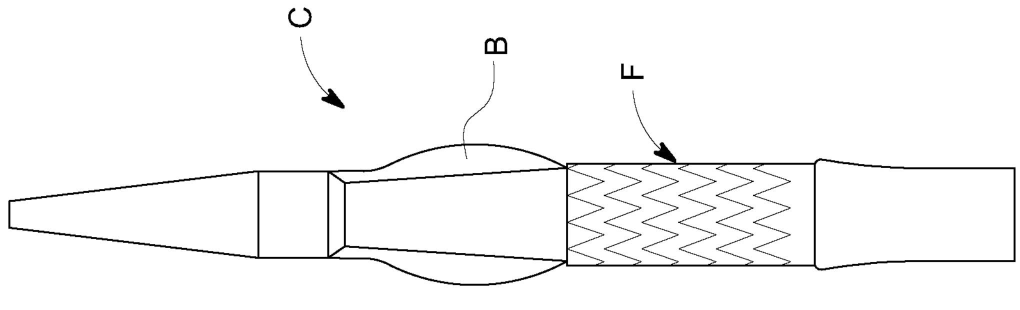
FIG. 1B Prior Art
FIG. 1B is a portion of a prior art catheter.

A more complete understanding of the articles/devices, processes and components disclosed herein can be obtained by reference to the accompanying drawings. These figures are merely schematic representations based on convenience and the case of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g., "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

For the sake of simplicity, the attached figures may not show the various ways (readily discernable, based on this disclosure, by one of ordinary skill in the art) in which the disclosed system, method and apparatus can be used in combination with other systems, methods and apparatuses. Additionally, the description sometimes uses terms such as "produce" and "provide" to describe the disclosed method. These terms are abstractions of the actual operations that can be performed. The actual operations that correspond to these terms can vary depending on the particular implementation and are, based on this disclosure, readily discernible by one of ordinary skill in the art.

Referring now to FIGS. 1A-1E, these figures are illustrations of an implantable prosthetic heart valve 100 (e.g., TAV) and a method for inserting the prosthetic heart valve 100 in a valve region A (e.g., aortic valve, etc.) of a heart H. Prosthetic heart valve 100 can be implanted in the annulus of native aortic valve A; however, prosthetic heart valve 100 also can be configured to be implanted in other valves of the heart. Although the medical device illustrated is a TAV, the present disclosure is not limited to TAVs or any other heart valve replacement.

Figure 1A:
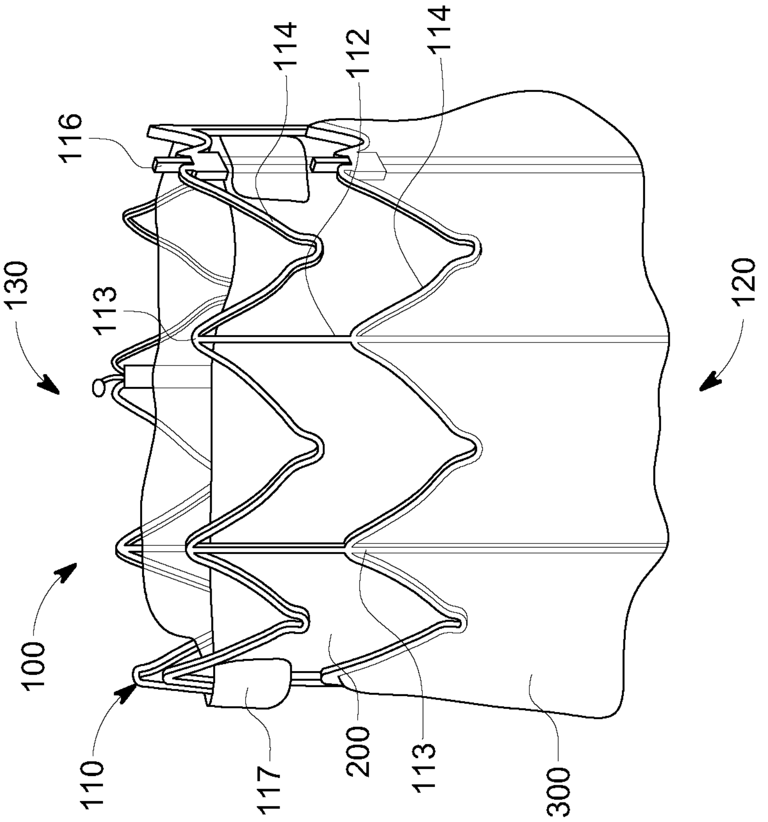
FIG. 1A is an illustration of a TAV in accordance with the present disclosure.

Referring now to FIG. 1A, prosthetic heart valve 100 generally comprises a frame 110 formed of a plurality of axial longitudinal members and angular articulating members 112, 114 strut joints 113, leaflet structure 200 supported by frame 110, and an inner skirt 300 secured to the outer surface of frame 110 and/or leaflet structure 200. The frame can include one or more an orientation structures or commissural markers 116. The frame 110 is partially or fully formed of a rhenium containing metal alloy. Prosthetic heart valve 100 has a "lower" end 120 and an "upper" end 130, wherein lower end 120 of prosthetic heart valve 100 is the inflow end and the upper end 130 of prosthetic heart valve 100 is the outflow end.

Frame 110 can be optionally be coated with a polymer material (e.g., silicone, PTFE, ePTFE, polyurethane, polyolefins, hydrogels, biological materials [e.g., pericardium or biological polymers such as collagen, gelatin, or hyaluronic acid derivatives], etc.). The coating can be used to partially or fully encapsulate one or more of the vertically extending axial longitudinal members 112 and/or non-vertically angular articulating members 114 on frame 110 and/or to partially or fully fill-in one or more of the openings between the non-vertically angular articulating members 114 and/or vertically extending axial longitudinal members 112.

The inner skirt 300 can be formed of a variety of flexible materials (e.g., polymer (e.g., polyethylene terephthalate (PET), polyester, nylon, Kevlar, silicon, etc.), composite material, metal, fabric material, etc. In one non-limiting embodiment, the material used to partially or fully form inner skirt 300 can be substantially non-elastic (i.e., substantially non-stretchable and non-compressible). In another non-limiting embodiment, the material used to partially or fully form inner skirt 300 can be a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). Inner skirt 300 can optionally be formed from a combination of a cloth or fabric material that is coated with a flexible material or with a stretchable and/or compressible material so as to provide additional structural integrity to inner skirt 300. The size, configuration, and thickness of inner skirt 300 is non-limiting (e.g., thickness of 0.1-20 mils and all values and ranges therebetween). The inner skirt 300 can be secured to the inside and/or outside of the frame 110 using various means (e.g., sutures, clips, clamp arrangement, etc.).

Inner skirt 300 can be used to 1) at least partially seal and/or prevent perivalvular leakage, 2) at least partially secure leaflet structure 200 to frame 110, 3) at least partially protect one or more of the leaflets of leaflet structure 200 from damage during the crimping process of prosthetic heart valve 100, 4) at least partially protect one or more of the leaflets of leaflet structure 200 form damage during the operation of prosthetic heart valve 100 in heart H.

Prosthetic heart valve 100 can optionally include an outer skirt or sleeve (not shown) that is positioned at least partially about the exterior region of frame 110. The outer skirt or sleeve (when used) generally is positioned completely around a portion of the outside of frame 110. Generally, the outer skirt is positioned about the lower portion of frame 110 and does not fully cover the upper portion of frame 110; however, this is not required. The outer skirt can be connected to frame 110 by a variety of arrangements (e.g., sutures, adhesive, melted connection, clamping arrangement, etc.). At least a portion of the outer skirt can optionally be located on the interior surface of frame 110; however, this is not required. Generally, the outer skirt is formed of a more flexible and/or compressible material than inner skirt 300; however, this is not required. The outer skirt can be formed of a variety of a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). The outer skirt can optionally be formed from a combination of a cloth or fabric material that is coated with the stretchable and/or compressible material so as to provide additional structural integrity to the outer skirt. The size, configuration, and thickness of the outer skirt is non-limiting. The thickness of the outer skirt is generally 0.1-20 mils (and all values and ranges therebetween).

Leaflet structure 200 can be can be attached to frame 110 and/or inner skirt 300. The connection arrangement used to secure leaflet structure 200 to frame 110 and/or inner skirt 300 is non-limiting (e.g., sutures, melted bold, adhesive, clamp arrangement, etc.). The material used to form the one or more leaflets of leaflet structure 200 include, but are not limited to, bovine pericardial tissue, biocompatible synthetic materials, or various other suitable natural or synthetic materials.

Leaflet structure 200 can be comprised of two or more leaflets (e.g., 2, 3, 4, 5, 6, etc.). In one non-limiting arrangement, leaflet structure 200 includes three leaflets that are arranged to collapse in a tricuspid arrangement. The size, shape and configuration of the one or more leaflets of leaflet structure 200 are non-limiting. In one non-limiting arrangement, the leaflets have generally the same shape, size, configuration and thickness.

Two of more of the leaflets of leaflet structure 200 can optionally be secured to one another at their adjacent sides to form commissures of leaflet structure 200 (the edges where the leaflets come together). Leaflet structure 200 can be secured to frame 110 and/or inner skirt 300 by a variety of connection arrangement (e.g., sutures, adhesive, melted bond, clamping arrangement, etc.).

One or more leaflets of the leaflet structure 200 can optionally include reinforcing structures or strips to 1) facilitate in securing the leaflets together, 2) facilitate in securing the leaflets to the inner skirt 300 and/or frame 110, and/or 3) inhibit or prevent tearing or other types of damage to the leaflets.

Prosthetic heart valve 100 is configured to be radially collapsible to a collapsed or crimped state for introduction into the body on a delivery catheter (FIG. 1B) and radially expandable to an expanded state for implanting prosthetic heart valve 100 at a desired location in heart H (e.g., aortic valve A, etc.) (FIG. 1E). The frame of prosthetic heart valve 100 is made of a plastically-expandable material (e.g., refractory metal alloy) that permits crimping of the frame to a smaller profile for delivery and expansion of prosthetic heart valve 100 using an expansion device. FIG. 1B illustrates a generic frame F of a prosthetic heart valve that is crimped on a generic balloon catheter C. The balloon B on the balloon catheter C can be used to expand the frame F from a crimped state to an expanded state. Various type of crimping apparatus and techniques can be used to crimp the prosthetic heart valve on the balloon delivery catheter. The process of crimping a prosthetic heart valve using a crimping device is known in the art and will not be described herein. During a crimping procedure, damage to leaflets of leaflet structure should be avoided.

Figure 1D:
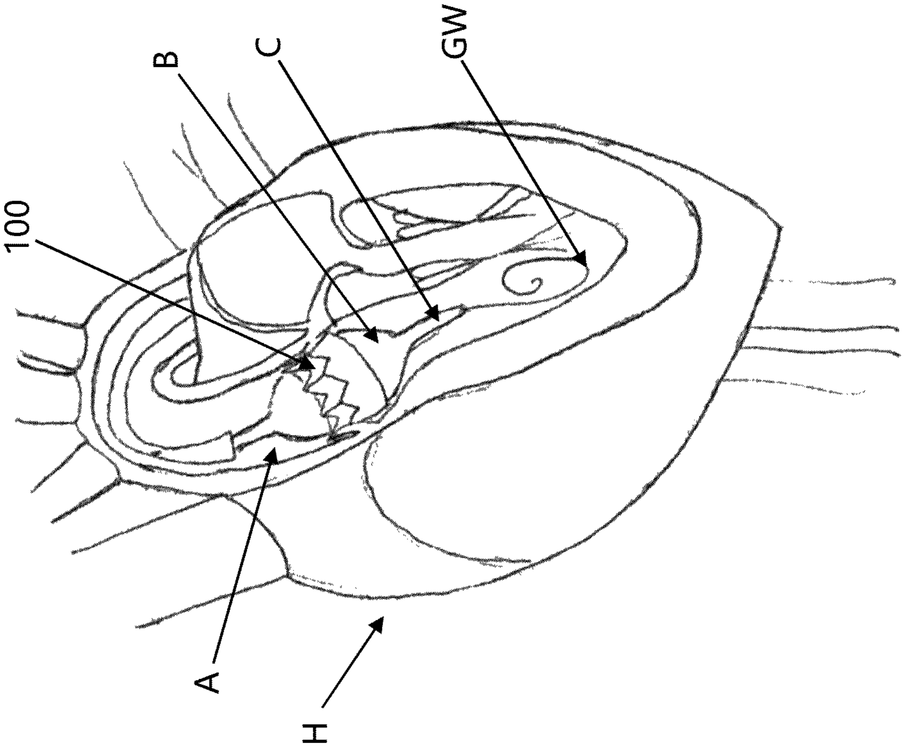
FIG. 1D Prior Art
FIGS. 1C-1E illustrate a typical TAVR procedure for inserting the TAV into a valve of a heart.
Figure 1C:
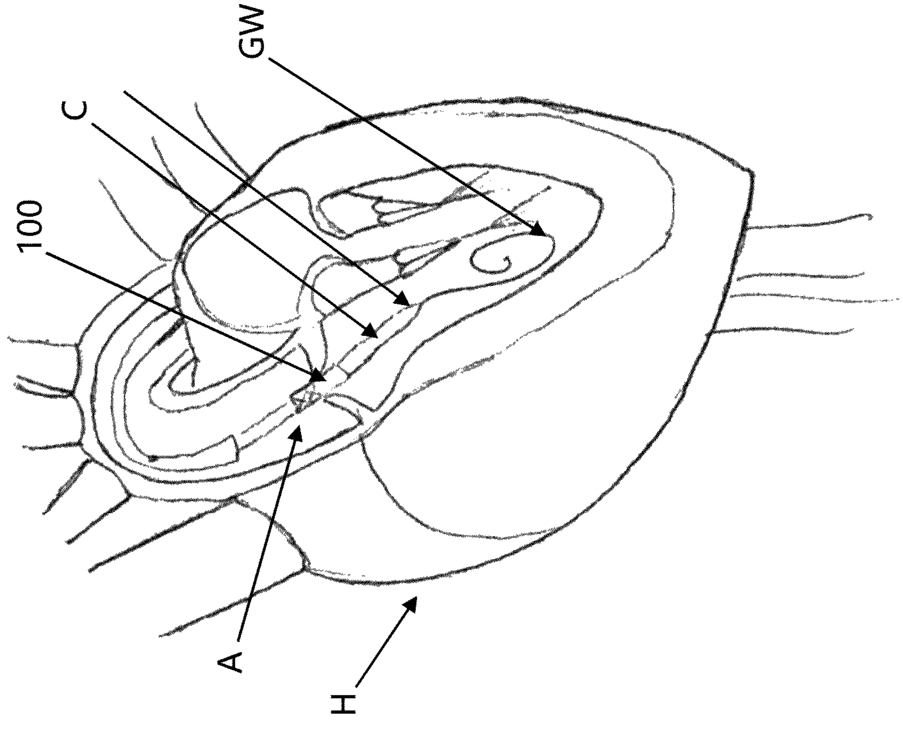
Figure 1E:
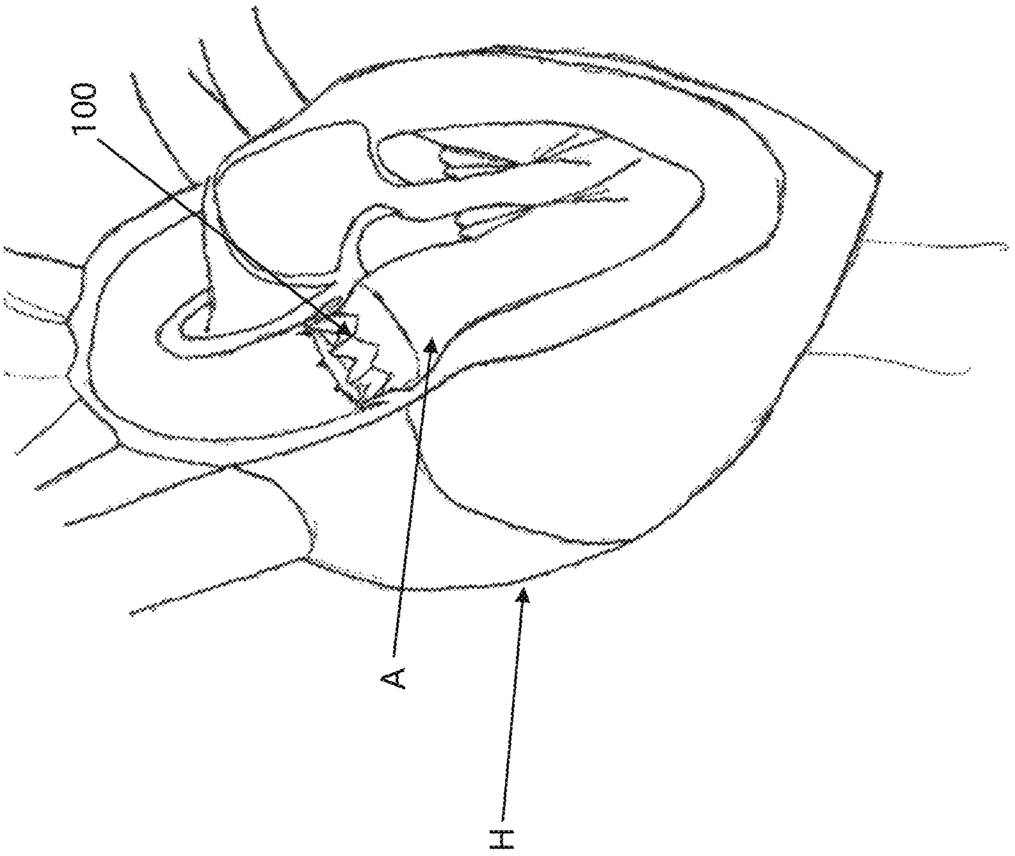

As illustrated in FIGS. 1C-1E, once prosthetic heart valve 100 is crimped on balloon B of a balloon catheter C, balloon catheter C is inserted through a blood vessel and to the location in heart H wherein prosthetic heart valve 100 is to be deployed (See FIG. 1C). At the treatment location, the balloon B on balloon catheter C is expanded to thereby cause prosthetic heart valve 100 to be expanded and secured in a valve region A of heart H (See FIG. 1D). Thereafter, balloon B is deflated and balloon catheter C is removed from the patient (See FIG. 1E).

The frame 110 of the prosthetic heart valve 100 can be configured such that it can be crimped onto a delivery catheter C so that the crimped prosthetic heart valve 100 can be inserted in heart valves that are less than 22 Fr. Commercially available prior art prosthetic heart values can only be crimped to a diameter of about 24-27 FR (8-9 mm) due to the materials used to form the frame of such prosthetic heart valves. As such, the prosthetic heart valve 100 in accordance with the present disclosure can be inserted into smaller sized heart valves that could not previously be treated with prior art prosthetic heart valves. As can be appreciated, the prosthetic heart valve 100 in accordance with the present disclosure can be sized and configured to be inserted in heart valves that are greater than 22 Fr.

The metal alloy frame 110 of the prosthetic heart valve 100 and other types of expandable medical devices (e.g., stents, etc.) that are formed of a refractory metal alloy or an alloy that includes at least 15 awt. % rhenium can be crimped to have a crimped outer diameter that is at least 5% and up to a 33% smaller (e.g., 5-33% smaller and all value and ranges therebetween) than a crimped outer diameter of a frame of the same size, configuration and shape that is formed of Co—Cr alloy (e.g., L605; MP35N; Phynox; Eligory; 35Co-35Ni-20Cr-10Mo; 40Co-20Cr-16Fe-15Ni7Mo; Co-20Cr-15W-10Ni; 15-30 wt. % Cr, 10-20 wt. % W, 5-35 wt. % Ni, 0-3 wt. % Fe, 0-2 wt. % Mn, 0-10 wt. % Mo, 0-1 wt. % Ti, 0.0.5 wt. % Si).

The metal alloy frame 110 of the prosthetic heart valve 100 and other types of expandable medical devices (e.g., stents, etc.) that are formed of a refractory metal alloy or an alloy that includes at least 15 awt. % rhenium can be crimped to have a crimped outer diameter that is at least 5% and up to a 50% smaller (e.g., 5-50% smaller and all value and ranges therebetween) than a crimped outer diameter of a frame of the same size, configuration and shape that is formed of stainless steel (e.g., 316, 316L).

The metal alloy frame 110 of the prosthetic heart valve 100 and other types of expandable medical devices (e.g., stents, etc.) that are formed of a refractory metal alloy or an alloy that includes at least 15 awt. % rhenium can be crimped to have a crimped outer diameter that is at least 5% and up to a 40% smaller (e.g., 5-40% smaller and all value and ranges therebetween) than a crimped outer diameter of a frame of the same size, configuration and shape that is formed of nitinol (self-expanding nickel titanium alloy-50-60 wt. % Ni and 40-60 wt. % Ti).

The metal alloy frame 110 of the prosthetic heart valve 100 and other types of expandable medical devices (e.g., stents, etc.) that are formed of a refractory metal alloy or an alloy that includes at least 15 awt. % rhenium can be crimped to have a crimped outer diameter that is at least 5% and up to a 40% smaller (e.g., 5-40% smaller and all value and ranges therebetween) than a crimped outer diameter of a frame of the same size, configuration and shape that is formed of TiAlV alloys (e.g., Ti-6Al-4V; 5.5-6.5 wt. % Al, 3.5-4.5 wt. % V and balance Ti; 3.5-4.5 wt. % vanadium, 5.5-6.75 wt. % aluminum, 0.3 wt. % max iron, 0.2 wt. % max oxygen, 0.08 wt. % max carbon, 0.05 wt. % max nitrogen, 0.015 wt. % max hydrogen H, 0.05 wt. % max yttrium, balance titanium).

As such, outer crimp diameters of the prosthetic heart valve 100 of 6-7 mm (18-21 FR) for a TAVR that was designed to be expanded to have an effective orifice area (EOA) of at least 585 mm$^2$, which were previously unachievable using stainless steel, CoCr alloy, nitinol, and can now be obtained by using a frame 110 formed of that are formed of a refractory metal alloy or an alloy that includes at least 15 awt. % rhenium.

Figure 2:
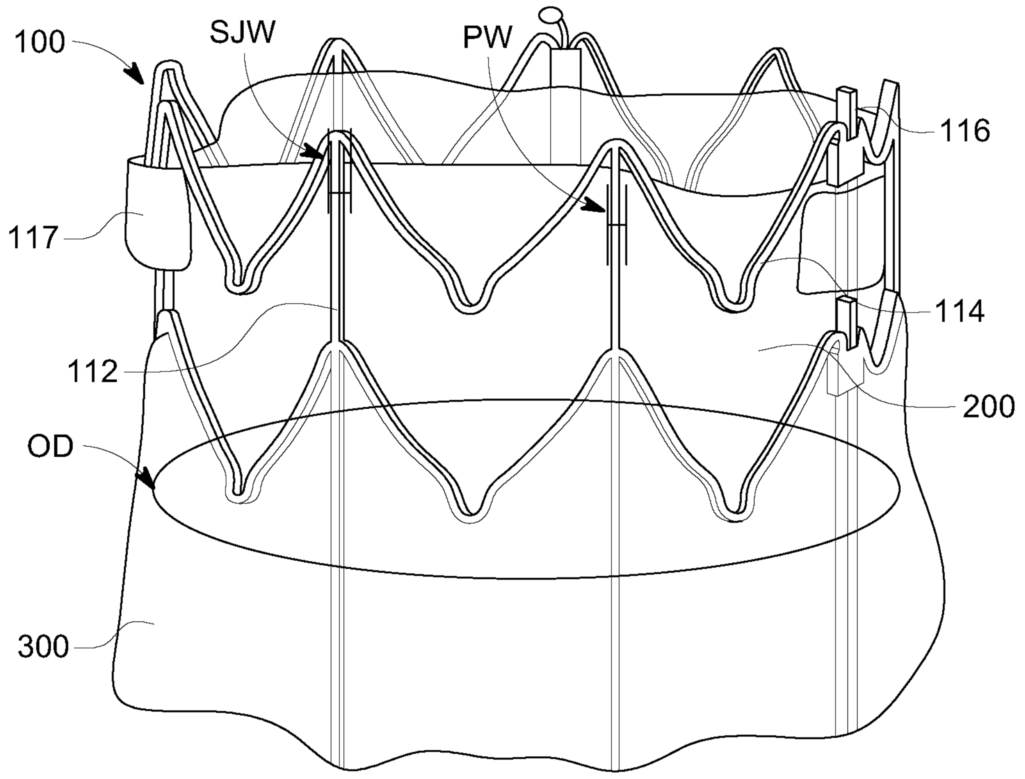
FIG. 2 is an illustration of a TAV that includes an inner skirt and leaflet structure.

Referring now to FIG. 2, the post width PW and/or the strut joint width SJW of a frame 110 that are formed of a refractory metal alloy or an alloy that includes at least 15 awt. % rhenium in accordance with the present disclosure can be smaller than the post width PW and/or the strut joint width SJW of a frame formed of stainless steel, nitinol, Co—Cr alloy or TiAlV alloy, and still have the same or greater radial strength when the frame is expanded as compared to a frame formed of stainless steel, nitinol, Co—Cr alloy or TiAlV alloy. A frame having smaller post widths and strut joint widths can be used in frames formed of that are formed of a refractory metal alloy or an alloy that includes at least 15 awt. % rhenium as compared to frames formed of stainless steel, CoCr, Nitinol, and TiAlV alloy without sacrificing the strength of the frame.

Generally, refractory metal alloys (e.g., 40-60 wt. % Mo, 40-60 wt. % Re, 0-10 wt. % one or more metal additives) used to form struts and posts and strut joint on expandable frames of TAV frames have an average cross-sectional area that is 5-40% (and all values and ranges therebetween) less than the cross-sectional area of the struts and posts and strut joints on TAV frames formed of CoCr alloy (e.g., L605; MP35N), and wherein such struts, post and/or strut joints are formed of a refractory metal alloy or an alloy that includes at least 15 awt. % rhenium have the same or greater strength than such struts, posts and strut joints formed of CoCr alloy.

Generally, refractory metal alloys (e.g., 40-60 wt. % Mo, 40-60 wt. % Re, 0-10 wt. % one or more metal additives) used to form struts and posts and strut joint on expandable frames of TAV frames have an average cross-sectional area that is 5-50% (and all values and ranges therebetween) less than the cross-sectional area of less than the cross-sectional area of the struts and posts and strut joints on TAV frames formed of stainless steel (e.g., 316, 316L), and wherein such refractory metal alloy struts, posts and strut joints have the same or greater strength than such struts, posts and strut joints formed of stainless steel.

Generally, refractory metal alloys (e.g., 40-60 wt. % Mo, 40-60 wt. % Re, 0-10 wt. % one or more metal additives) used to form struts and posts and strut joint on expandable frames of TAV frames have an average cross-sectional area that is 5-40% (and all values and ranges therebetween) less than the cross-sectional area of the struts and posts and strut joints on TAV frames formed of TiAlV alloy (e.g., Ti-6Al-4V), and wherein such refractory metal alloy struts, posts and strut joints have the same or greater strength than such struts, posts and strut joints formed of TiAlV alloy.

Generally, refractory metal alloys (e.g., 40-60 wt. % Mo, 40-60 wt. % Re, 0-10 wt. % one or more metal additives) used to form struts and posts and strut joint on expandable frames of TAV frames have an average cross-sectional area that is 5-40% (and all values and ranges therebetween) less than the cross-sectional area of the struts and posts and strut joints on TAV frames formed of Nitinol (e.g., 50-60 wt. % Ni and 40-60 wt. % Ti), and wherein such refractory metal alloy struts, posts and strut joints have the same or greater strength than such struts, posts and strut joints formed of Nitinol.

The use of a refractory metal alloy or an alloy that includes at least 15 awt. % rhenium to form the frame of TAV frames allows for smaller expandable TAVs to be manufactured. Such smaller expandable TAVs can be inserted into smaller blood vessels or other body passageways that previously could not be accessed using TAVs formed of other types of metal alloys.

Due to the properties of the refractory metal alloy or an alloy that includes at least 15 awt. % rhenium, a TAV frame formed of a refractory metal alloy or an alloy that includes at least 15 awt. % rhenium as compared to a TAV frame formed of TiAlV alloy [wherein both frames have a) the same number of posts and struts, b) the same post and strut configuration and shape, c) the frame formed of a refractory metal alloy or an alloy that includes at least 15 awt. % rhenium can be expanded to the same or greater effective orifice area (EOA) as the expanded frame formed of TiAlV alloy, and d) the frame that is formed of a refractory metal alloy or an alloy that includes at least 15 awt. % rhenium has the same or greater radial strength in an expanded state as the frame formed of TiAlV alloy in an expanded state] can 1) be formed of at least 5% less material (e.g., 5-50% less material and all values and ranges therebetween), 2) have SJWs that are at least 5% thinner (e.g., 5-50% thinner and all values and ranges therebetween), c) have PWs that are at least 5% thinner (e.g., 5-50% thinner and all values and ranges therebetween), and 3) have a crimped outer diameter that is at least 5% smaller (e.g., 5-40% smaller and all values and ranges therebetween).

The post width and strut joint width using a refractory metal alloy or an alloy that includes at least 15 awt. % rhenium can thus be reduced as compared to post widths and strut joint widths on frames formed of TiAlV alloy without a reduction in the strength of the frame in the expanded state. Due to the smaller crimped outer diameter of the frame that is achievable using a refractory metal alloy or an alloy that includes at least 15 awt. % rhenium, the outer crimped diameter of the prosthetic heart valve using a frame formed of a refractory metal alloy or an alloy that includes at least 15 awt. % rhenium is less than a prosthetic heart valve using a frame formed of TiAlV alloy.

A frame formed of a refractory metal alloy or an alloy that includes at least 15 awt. % rhenium was found to have less recoil after being expanded than a frame formed of CoCr alloy. Specifically, it was found that a frame formed of MoRe alloy had a recoil of less than 2% after expansion has compared to a frame formed of CoCr alloy that had 9% or more recoil after expansion. Generally, frames formed of a refractory metal alloy or an alloy that includes at least 15 awt. % rhenium have a recoil that is 1.5-8 times less (and all values and ranges therebetween) than a frame formed of a CoCr alloy, stainless steel, or a TiAlV alloy. As such, a frame formed of a refractory metal alloy or an alloy that includes at least 15 awt. % rhenium will better conform to the shape of the heart passageway wherein the frame is expanded, thus reducing the amount of paravalvular or paraprosthetic leak (PVL) about the prosthetic heart valve after expansion. Furthermore, a frame formed of a refractory metal alloy or an alloy that includes at least 15 awt. % rhenium will expand to its desired expanded state from a single inflation of the balloon of the balloon delivery catheter. Due to the significant recoil of a frame formed of CoCr alloy, stainless steel, and TiAlV alloy after expansion, the balloon of the balloon delivery catheter typically needs to be inflated multiple times to cause the frame to conform to the shape of the heart passageway wherein the frame is expanded. Such multiple inflations of the balloon can result in increased incidence of damage to the prosthetic heart valve and/or to the heart passage way wherein the frame is expanded.

It has been found that wires formed of a refractory metal alloy or an alloy that includes at least 15 awt. % rhenium (e.g., MoRe alloy, ReW alloy, MoReCr alloy, MoReTa alloy, MoReTi alloy, WCu alloy, ReCr alloy, Mo alloy, Re alloy, W alloy, Ta alloy, Nb alloy) have about 15-45% (and all values and ranges therebetween) better conformity to bending to an idea bending shape formed by a die than the same sized wire formed of stainless steel, CoCr alloy, and TiAlV alloy. Such better shape conformity exhibited by a refractory metal alloy or an alloy that includes at least 15 awt. % rhenium is believed to be due in part to the reduced recoil of the refractory metal alloy or an alloy that includes at least 15 awt. % rhenium and one or more other properties of a refractory metal alloy or an alloy that includes at least 15 awt. % rhenium (e.g., strength of alloy, etc.). Such improved shape conformity of a refractory metal alloy or an alloy that includes at least 15 awt. % rhenium results in improved conformity of an expanded TAV frame formed of the refractory metal alloy or an alloy that includes at least 15 awt. % rhenium to the treatment area shape compared to frames formed of traditional metal alloys.

Because the expandable TAV frame formed of a refractory metal alloy or an alloy that includes at least 15 awt. % rhenium betters conform to the shape of a body passageway wherein the TAV frame is expanded, there is a reduction in the amount of paravalvular or paraprosthetic leak (PVL) or other type of leakage about the TAV after expansion. Furthermore, an expandable TAV frame formed of a refractory metal alloy or an alloy that includes at least 15 awt. % rhenium will expand to its desired expanded state from a single inflation of the balloon of a balloon delivery catheter. Due to the significant recoil of an expandable TAV frame formed of stainless steel, CoCr alloy, or TiAlV alloy after expansion, the balloon of the balloon delivery catheter typically needs to be inflated multiple times to cause the expandable frame to conform as close as possible to the shape of the body passageway wherein the expandable frame is expanded. Such multiple inflations of the balloon can result in increased incidence of damage to the medical device and/or to the body passageway wherein the expandable frame is expanded.

The reduced amount of recoil, improved bending conformity and greater radial strength of expanded TAV frames that are at least partially formed of a refractory metal alloy or an alloy that includes at least 15 awt. % rhenium as compared to expandable TAV frames formed of stainless steel, CoCr alloy, and TiAlV alloy results in the following non-limiting advantages: 1) formation of a frame for a medical device having thinner posts, struts, and/or strut joints which results in i) safer vascular access when inserting the medical device through a body passageway and to the treatment area, and/or ii) decreased the risk of bleeding and/or damage to the body passageway and/or the treatment area when the medical device is delivered to the treatment area and/or expanded at the treatment area; 2) easier deliverability of the medical device to the treatment area which can result in i) decreased trauma to the body passageway (e.g., blood vessel, aortic arch trauma, etc.) during the insertion and/or expansion of the medical device at the treatment area, and/or ii) decreased risk of neuro complications-stroke; 3) less recoil which results in i) reduced crimping profile size, ii) increased conformability of the expanded medical device at the treatment area after expansion in the treatment area, iii) increased radial strength of the frame of the medical device after expansion at the treatment area, iv) only require a single crimping cycle to crimp the medical device on a balloon catheter or other type of delivery device, v) reduced incidence of damage to components of the medical device (e.g., struts, posts, strut joints, and/or other components of the expandable frame, leaflets, skirts, coatings, etc.) during the crimping, expansion, and operation of the medical device, vi) greater effective orifice area (EOA) of the medical device after expansion of the medical device, vi) decreased pulmonary valve regurgitation (PVR) after expansion of the medical device in the treatment area, and/or vii) require only a single expansion cycle of the balloon on the balloon catheter or other expansion mechanism to fully expand the medical device; and/or 4) creating a medical device having superior material biologic properties to I) improved tissue adhesion and/or growth on or about medical device, II) reduced adverse tissue reactions with the medical device, III) reduced toxicity of medical device, IV) potentially decreased in-valve thrombosis during the life of the medical device, and/or V) reduced incidence of infection during the life of the medical device.

Medical devices, such as expandable heart valves that are at least partially formed of a refractory metal alloy or an alloy that includes at least 15 awt. % rhenium in accordance with the present disclosure, overcome several unmet needs that exist in expandable medical device formed of CoCr alloys, TiAlV alloys, and stainless steel. Such unmet needs addressed by the medical devices in accordance with the present disclosure include 1) not having to form a large hole in large arterial vessels or other blood vessels for initial insertion of the crimped medical device into the atrial vessel or other blood vessel, thereby reducing the incidence of lethal bleeding during a treatment; 2) enabling the medical device to be delivered and implanted in abnormally shaped heart valves or through an abnormally shaped arterial vessel due to calcination in the prosthetic heart valve and/or calcination and/or plaque in the arterial vessel by creating a medical device (e.g., stent, prosthetic heart valve, etc.) having a reduced crimped profile that is smaller than medical devices formed of CoCr alloys, TiAlV alloys, and stainless steel; 3) reducing the incidence of a perivalvular leak and/or other types of leakage about the implanted medical device when the medical device is expanded in the treatment region by using a frame formed of a refractory metal alloy or an alloy that includes at least 15 awt. % rhenium that better conforms to the shape of the abnormally shaped heart valve orifice upon expansion of the prosthetic heart valve comparted to prior art prosthetic heart valves formed of CoCr alloys, TiAlV alloys, and stainless steel, thereby reducing the incidence of stroke and/or by increasing the incidence of success of the implanted medical device; 4) improving the radial strength of the expanded struts, posts, and/or strut joints in the expandable frame and the strength of the expandable frame itself after expansion the medical device; 5) reducing the amount of recoil of the expandable frame during the crimping and/or expansion of the expandable frame of the medical device; 6) enabling the medical device to be used in a heart that has a permanent pacemaker; 7) reducing the incidence of minor stroke during the insertion and operation of the medical device at the treatment area; 8) reducing the incidence of coronary ostium compromise; 9) improving foreshortening; 10) reducing further aortic valve calcification and/or calcification in a blood vessel after implantation of the medical device; 11) reducing the need for multiple crimping cycles when inserting the medical device on a catheter or other type of delivery system; 12) reducing the incidence of frame fracture during the crimping and/or expansion of the medical device; 13) reducing the incidence of biofilm-endocarditis after implantation of the medical device; 14) reducing allergic reactions to the medical device after implantation of the medical device; 15) improving the hydrophilicity of the medical device to improve tissue growth on and/or about the implanted medical device, 16) reduce the magnetic susceptibility of the medical device, 17) reduce the toxicity of the medical device, 18) reduce the amount of metal ion release from the medical device, and/or 19) increasing the longevity of leaflets and/or frame and/or other components of the medical device after insertion of the medical device.

Figure 3:
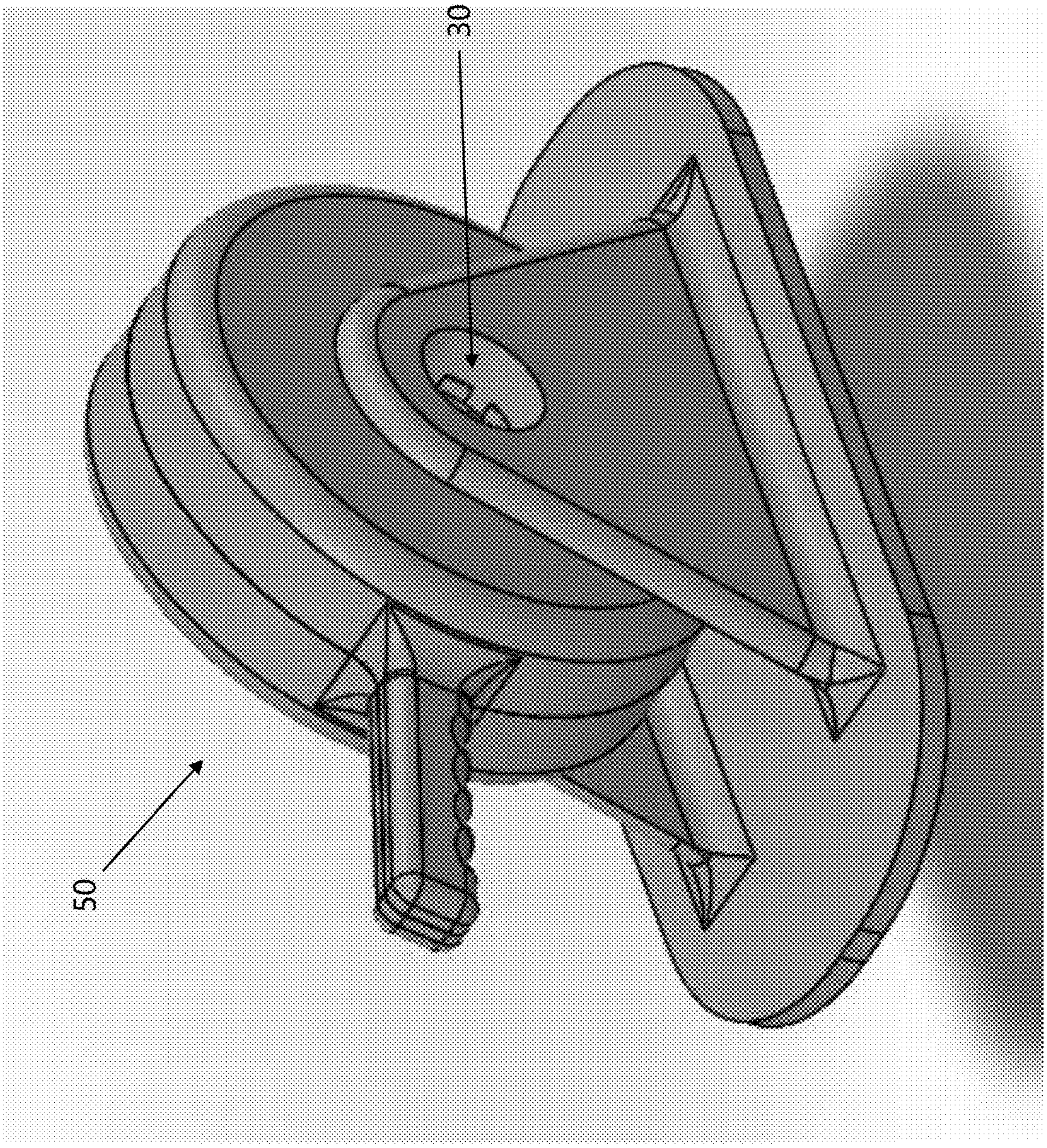
FIGS. 3-4 illustrated a non-limiting crimper device that can be used to crimp a prosthetic heart valve.
Figure 4:
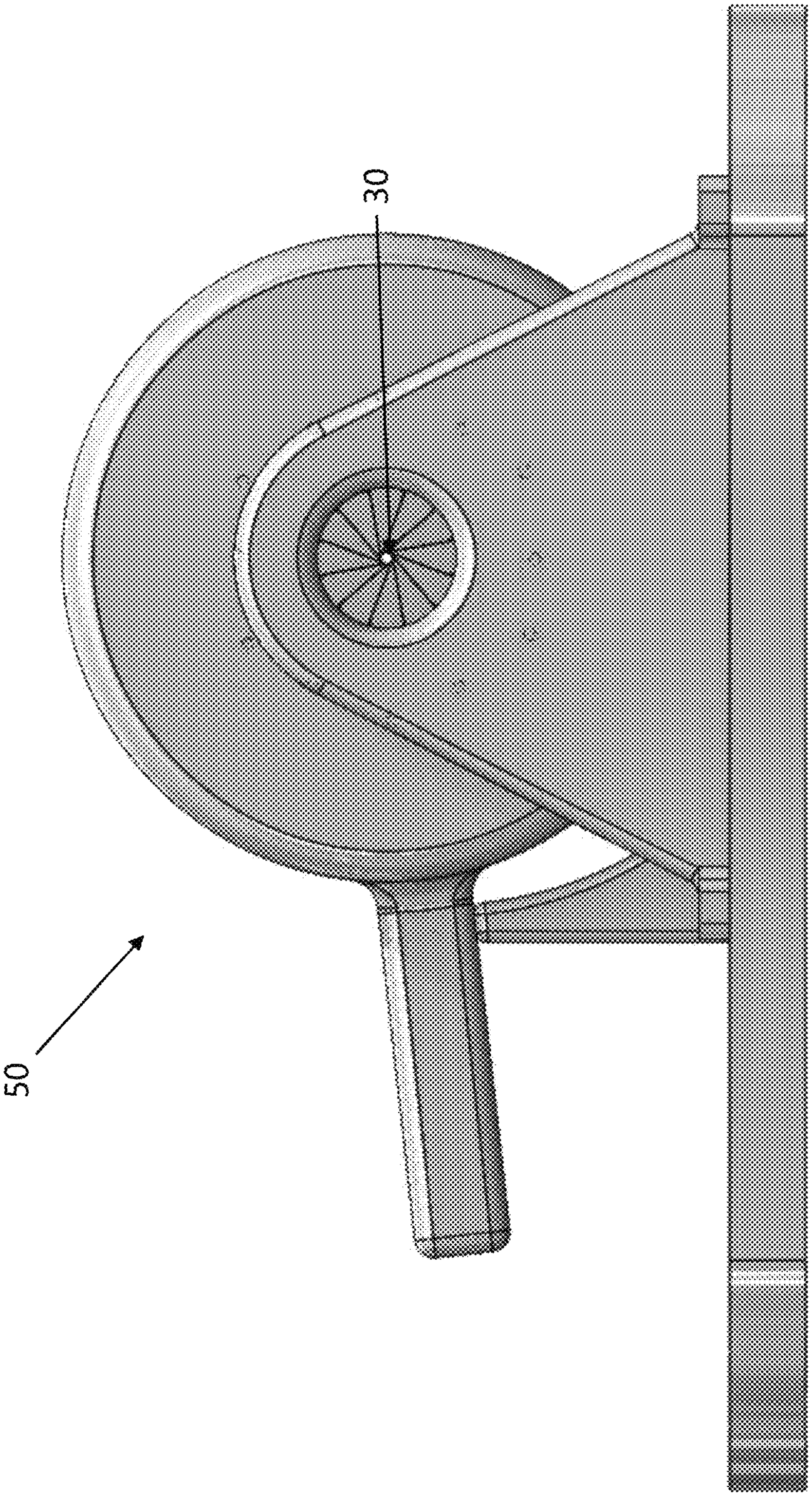

Referring now to FIGS. 3-4, a non-limiting crimper device 50 is illustrated that can be used to crimp the prosthetic heart valve. Crimper device 50 includes an opening 30 wherein the prosthetic heart valve is placed to be crimped.

Figure 5:
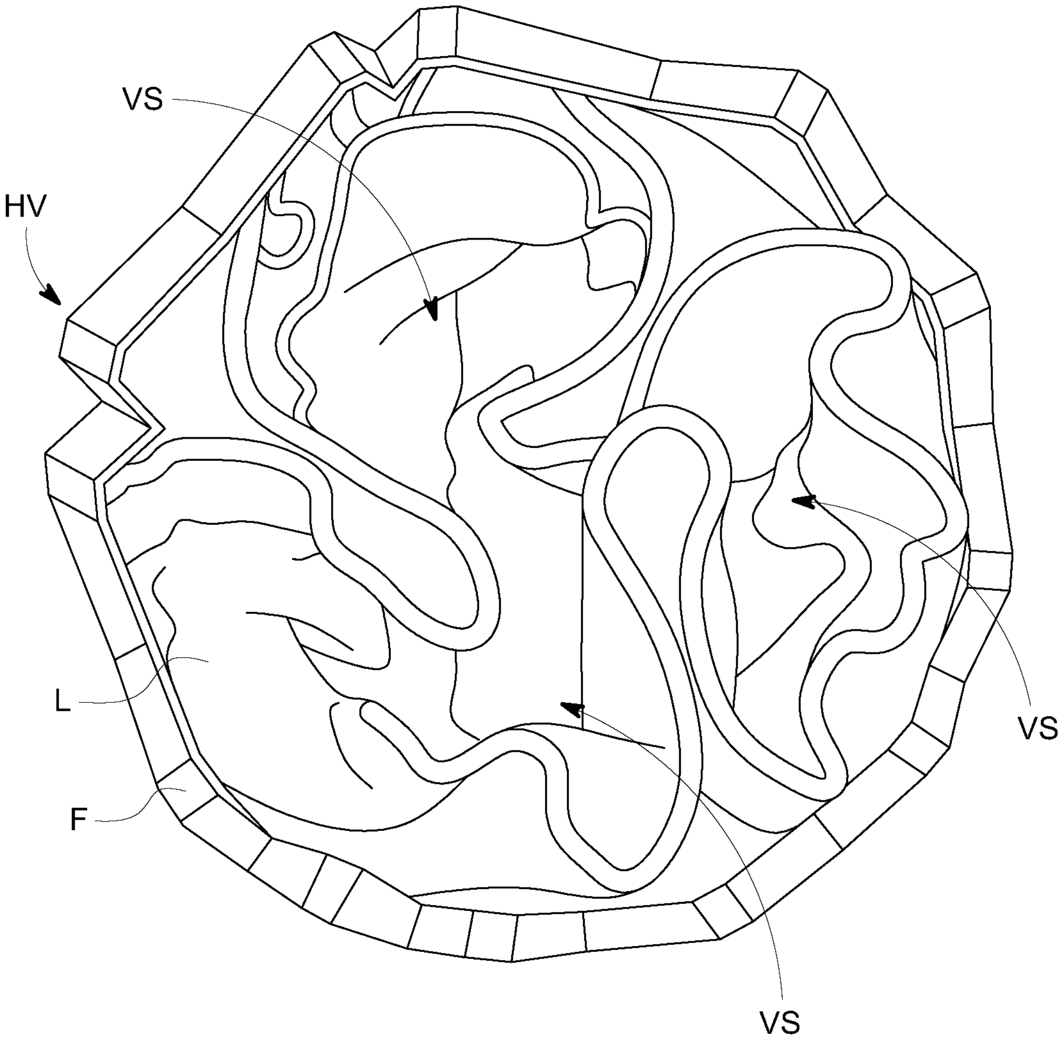
FIG. 5 illustrates the folding profile of leaflets in a partially crimped prosthetic heart valve by use of the crimping process in accordance with the present disclosure wherein the leaflets are being to align so that void spaces are reduced once the frame is fully crimped.

Referring now to FIG. 5, there is illustrated a rear-end view or outflow side end view of a crimped prosthetic heart valve that is has been partially crimped by the crimper device and crimping process as disclosed herein. As illustrated in FIG. 5, the leaflets are illustrated as beginning to be folded in an organized manner that reduces the number and volume of void spaces existing about the folded leaflets.

Figure 6:
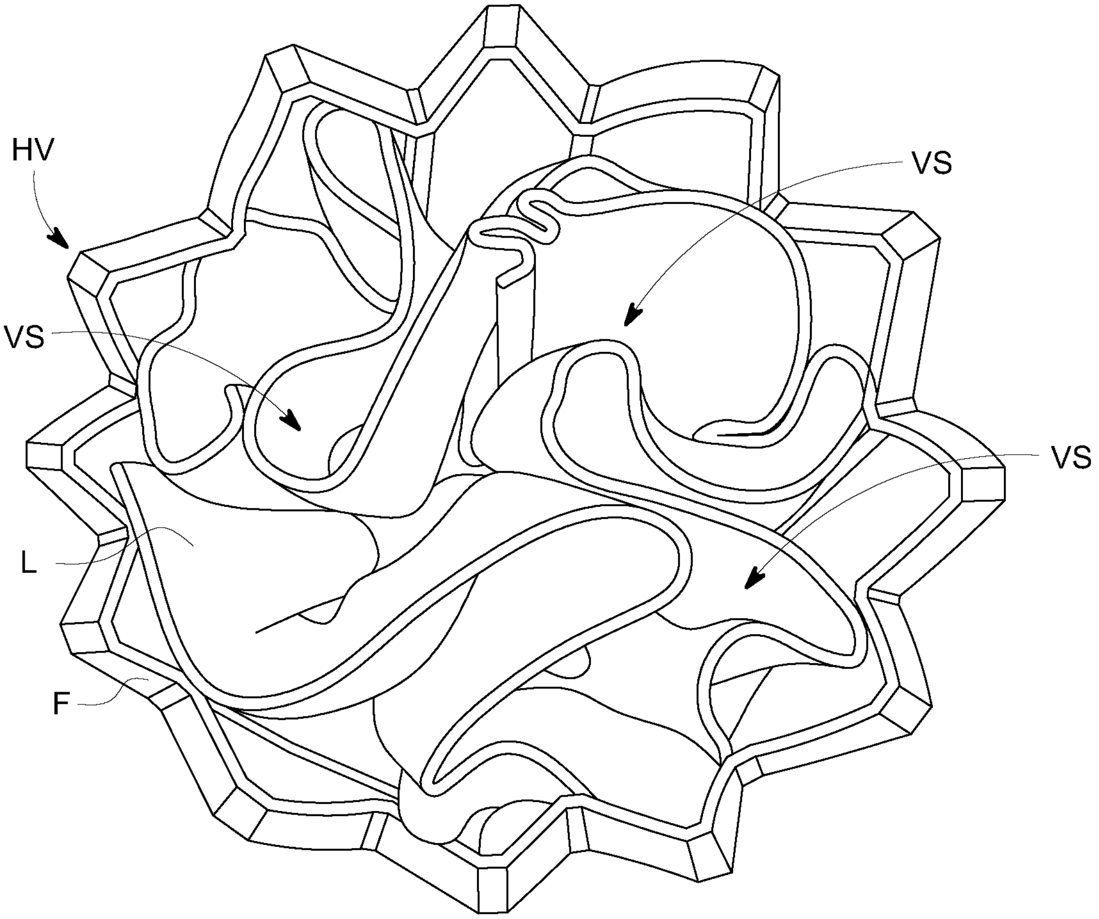
FIG. 6 illustrates the folding profile of leaflets in the fully crimped prosthetic heart valve, wherein the prosthetic heart valve was crimped by the crimper device in accordance with the present disclosure and wherein the leaflets were caused to be folded in accordance with the one or more methods of the present disclosure, and wherein there is a reduction of void spaces about the folded leaflets when the frame valve is in the fully crimped state.

Referring now to FIG. 6, there is illustrated a rear-end view or outflow side end view of a crimped prosthetic heart valve showing the folding profile of leaflets in the fully crimped prosthetic heart valve that has been crimped by the crimper device and crimping process as disclosed herein. The prosthetic heart valve was crimped in such a way as to cause the leaflets to be folded in an organized manner that reduces the number and volume of void spaces about the folded leaflets, thereby enabling the frame of the prosthetic heart valve to be crimped to a smaller outer diameter.

Figure 7A:
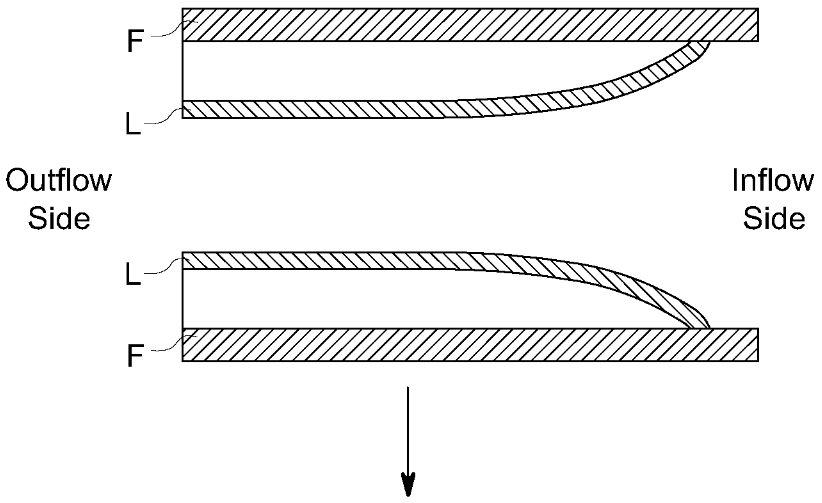
FIGS. 7A-7C illustrates one non-limiting crimping method for progressively or stepwise crimping a prosthetic heart valve to obtain a leaflet folding arrangement by use of the crimper device in accordance with the present disclosure so as to obtain a leaflet folding arrangement of FIGS. 5 & 6.
Figure 7B:
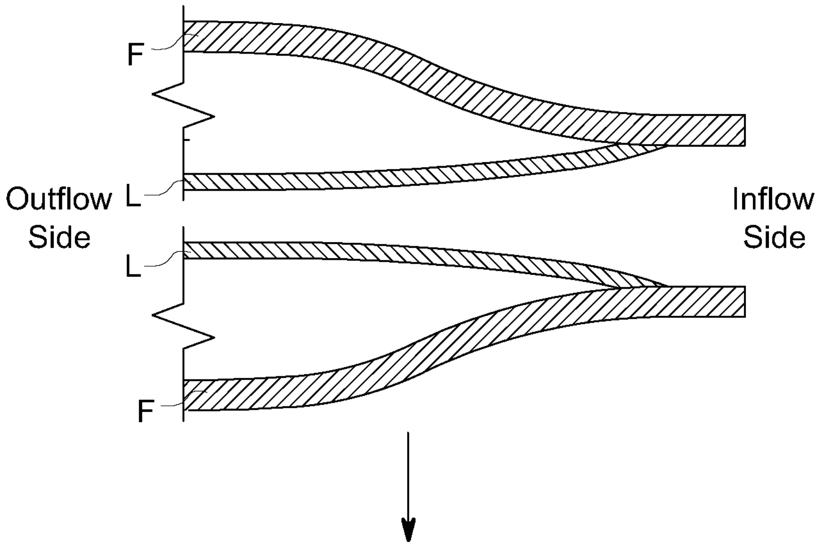
Figure 7C:
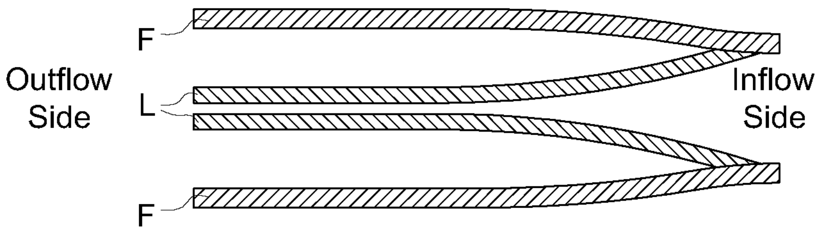
Figure 8A:
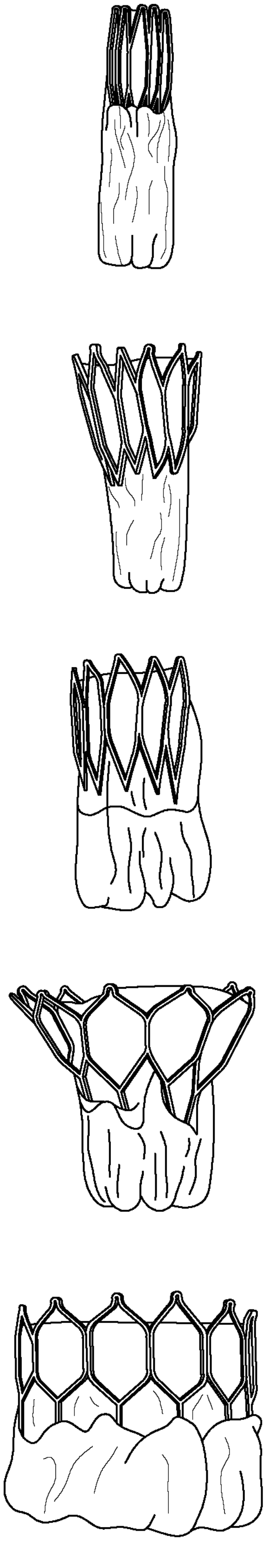
FIGS. 8A-8B illustrate a side view and end view of the prosthetic heart valve that has been subjected to a non-limiting continuous progressive crimping process in accordance with the present disclosure.
Figure 8B:
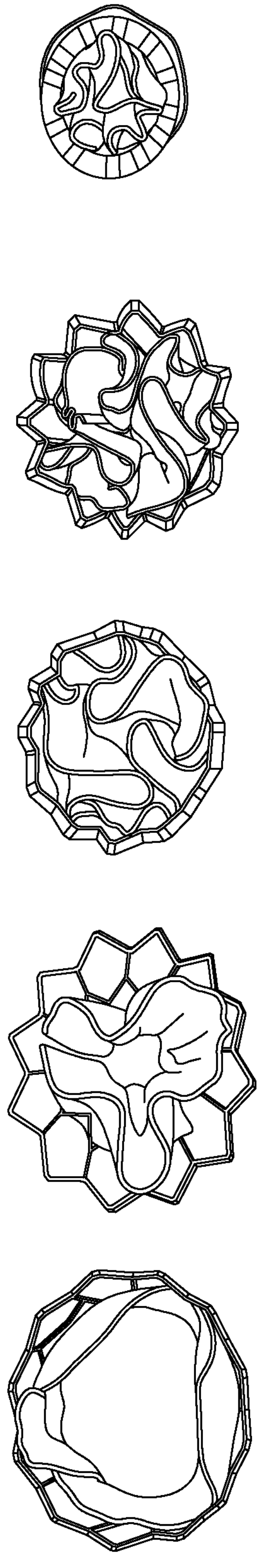

Referring now to FIGS. 7A-7C, there is illustrated a three cross-sectional portions of a prosthetic heart valve along the longitudinal axis of the prosthetic heart valve wherein two leaflets are connected to the frame of the prosthetic heart valve. FIGS. 7A-7C18 illustrate the inflow side and outflow side of the prosthetic heart valve. The leaflets are illustrated as being connected to the frame at or near the inflow side of the prosthetic heart valve.

FIG. 7A illustrates a cross-sectional portion of the prosthetic heart valve prior to the frame being subjected to a crimping force by the crimper device. For example, when the handle is in the fully open position and the prosthetic heart valve is positioned in opening 30, the diameter or cross-sectional area of opening 30 can be such that no crimping force is applied to the prosthetic heart valve.

FIG. 7B illustrates a cross-sectional portion of the prosthetic heart valve wherein the inflow region of the frame has been subjected to a crimping force to cause a reduction in diameter or cross-sectional area of the crimped frame; however, the outflow region of the frame has not yet been subjected to a crimping force, thus there has been no reduction in diameter or cross-sectional area of this region of the frame. For example, as the handle is moved from the fully opened position to the fully closed or smallest diameter or cross-sectional area position for opening 30, the a first set of jaws of the crimper device can be configured to first contacting and applying a crimping force to the inflow region of the prosthetic heart valve prior to a second set of jaws contacting and applying a crimping force to the outflow region of the prosthetic heart valve.

FIG. 7C illustrates a cross-sectional portion of the prosthetic heart valve wherein both the inflow region and outflow regions of the frame has been subjected to a crimping force to cause a reduction in diameter or cross-sectional area of the crimped frame. For example, as the handle is continued to be moved to the fully closed or smallest diameter or cross-sectional area position for opening 30, the second set of jaws eventually contact and apply a crimping force to the outflow region of the prosthetic heart valve while the first set of jaws continue to apply a crimping force to the inflow region of the prosthetic heart valve.

Figure 9A:
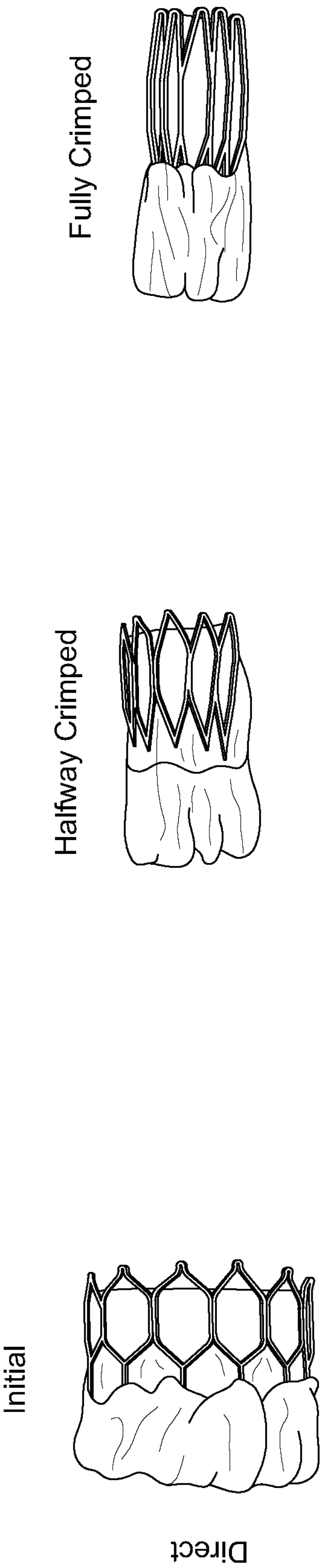
FIGS. 9A-9B illustrate a side view and end view of the prosthetic heart valve that has been subjected to a non-limiting stepwise crimping process in accordance with the present disclosure.
Figure 9B:
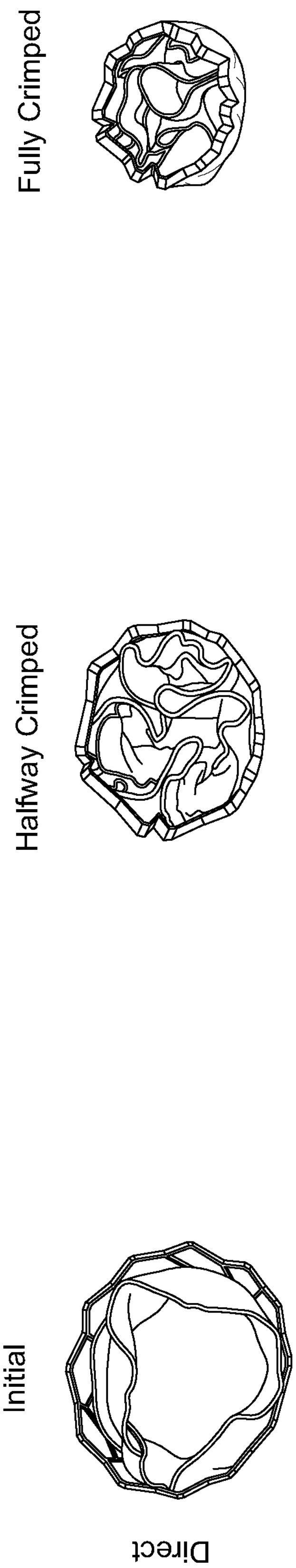
Figure 11:
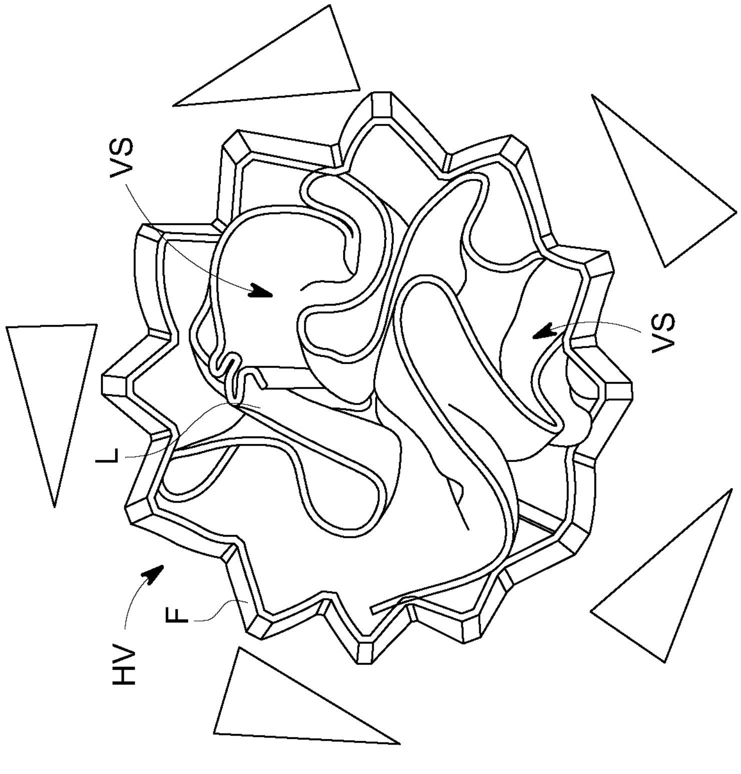
FIG. 11 illustrates the outflow end of a fully crimped frame of a prosthetic heart valve and wherein the arrows illustrate the counter-clockwise folding profile pattern of the leaflets so as to reduce the void spaced about the leaflets, and wherein the counter-clockwise folding profile pattern of the leaflets by the use of the crimping method in accordance with the present disclosure and the optional use of the leaflet folding device illustrated in FIG. 10.

Referring now to FIGS. 8A, 8B, 9A, 9B, there are illustrated non-limiting crimping methods for a prosthetic heart valve using the disclosed crimper device, wherein: a) the prosthetic heart valve is progressively and continuously crimped along its longitudinal axis starting from the inflow end and progressing to and end at the outflow end (Sec FIGS. 8A-8B), or b) the inflow side portion of the prosthetic heart valve is first partially or fully crimped, and thereafter the outflow side portion of the prosthetic heart valve is partially or fully crimped (See FIGS. 9A-9B). Such a crimping method results in an organized leaflet profile of the crimped prosthetic heart valve that is the same or similar to the folded leaflet profile as illustrated in FIGS. 5, 6 and 11.

Figure 10:
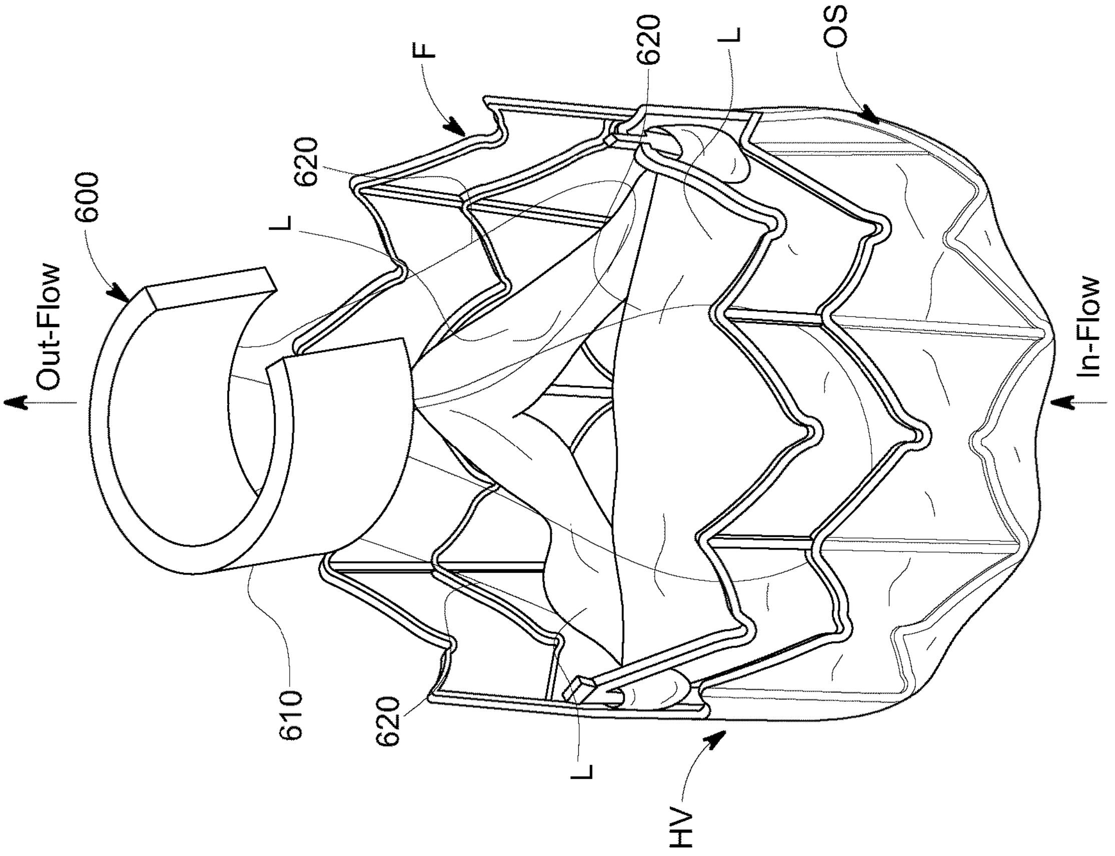
FIG. 10 illustrates a non-limiting leaflet folding device that can optionally be used with the crimper device in accordance with the present disclosure to facilitate in obtaining a leaflet folding configuration during the crimping of the frame of a prosthetic heart valve so as to obtain a folded leaflet configuration after the frame has been fully crimped as illustrated in FIGS. 5, 6, 8A-8B, and 9A-9B.

Referring R now to FIG. 10, there is illustrated a prosthetic heart valve HV that includes a frame F, three leaflets L, and an inner skirt and an outer skirt OS. A leaflet folding device 600 is illustrated which can optionally be used with the crimper device to facilitate in obtaining a desired leaflet folding configuration during the crimping of the frame of a prosthetic heart valve. The leaflet folding device 600 includes a handle 610 and three leaflet engagement members 620 in the form of wire loops (e.g., metal wire loop, plastic wire loop, etc.) that are attached to and extend from the handle 610. FIG. 10 only illustrates a portion of the handle 610. Generally, the handle 610 is sized and shaped to such that it can be grasped by a user to enable the user to position the leaflet engagement members into a portion of the prosthetic heart valve to cause the bending of the one or more leaflets.

The leaflet engagement members 620 are attached to the distal end or distal end portion of the handle portion and are illustrated as extending radially outwardly from the central longitudinal axis of the handle portion. Generally, the leaflet engagement members have the same size, shape, and/or be formed of the same material; however, this is not required.

The leaflet engagement members can be formed of a flexible material that enables the leaflet engagement members to flex and/or bend a) when positioning the leaflet engagement members about one or more leaflets, and/or b) during the crimping of the frame of the prosthetic heart valve and while the leaflet engagement members are still engaged with the one or more leaflets during the crimping of the frame.

The leaflet folding device is configured to inwardly bend one or more or all of the end portions of the leaflets that are located at or near the outflow end of the prosthetic heart valve toward the central axis of the frame of the prosthetic heart valve. Such bending of the one or more leaflets by the leaflet folding device generally occurs a) prior to the initial crimping of the frame of the prosthetic heart valve, and/or b) during the crimping of the frame of the prosthetic heart valve. Generally, the leaflet folding device is removed from or disengaged from the one or more leaflets prior to the outflow end of the frame of the prosthetic heart valve being fully crimped to as to not interfere with the complete crimping of the frame of the prosthetic heart valve.

When the leaflet folding device 600 is optionally used, one non-limiting method of use is as follows: a) the leaflet folding device is moved along the longitudinal axis of the frame and toward the frame until the one or more leaflet engagement members engage the end or end portion of the one or more leaflets, b) thereafter, the leaflet folding device is continued to be moved along the longitudinal axis of the frame such that the end or end portion of the one or more leaflet engagement members move between the one or more leaflets and the inner surface of the frame, and c) thereafter, the leaflet folding device is continued to be moved along the longitudinal axis of the frame such that the angular orientation of the one or more leaflet engagement members relative to the central axis of the handle portion of the leaflet folding device causes the end and end portions of the leaflets to be bent toward the central axis of the frame. Generally, one or more leaflet engagement members are inserted only through a portion of the longitudinal length of the frame and are spaced from the region of the frame wherein the one or more leaflets are connected to the frame. Prior to and/or during the crimping of the frame, the handle portion of the leaflet folding device can be optionally rotated about the longitudinal axis of the frame so as to facilitate in the folding of the leaflets during the crimping of the frame. Such rotation is illustrated by the arrows in FIG. 11.

Figure 12:
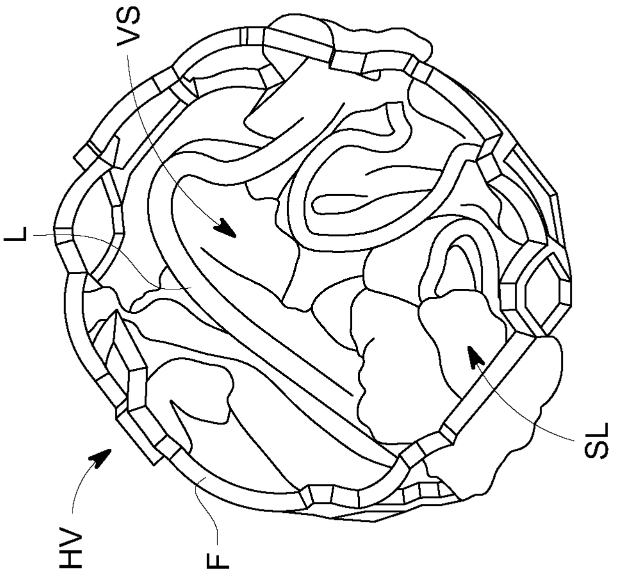
FIG. 12 illustrates the outflow of a fully crimped frame of a prosthetic heart valve wherein the frame has been fully crimped by a prior art crimper and prior art crimping method, and wherein the leaflet configuration is disorganized which there by results in large void spaces between the leaflets and the crushing and the potential damaging of one or more of the leaflets.

As illustrated in FIG. 12, when the leaflets of the prosthetic heart valve are not properly folded, the leaflets can be subjected to damage (e.g., leaflet tearing, damage between the connection of the leaflet and frame, damage to the connection between leaflets, creasing of the leaflet that adversely alters the shape of the leaflet when the frame is expanded at the treatment site, etc.), and the frame typically is prevented from being crimped to its smallest profile. Repeated applied crimping pressure to the frame to attempt to obtain smaller frame crimping profiles can result in a) no further crimping profile reduction, b) damage or further damage to one or more leaflets, c) damage to the inner and/or outer skirt, and/or d) damage to the frame. FIG. 12 illustrates a typically folding profile of leaflets F after the frame F of a prosthetic heart valve HV has been crimped by prior art crimping devices and methods. As illustrated in FIG. 12, the folding of the leaflets L is not organized as compared to the leaflet folding arrangement illustrated in FIG. 11. Also, there are significant void spaces VS about the folded leaflets L in the crimped prosthetic heart valve HV illustrated in FIG. 12. FIG. 11 illustrates a significantly less number and volume of void spaces VS between the organized folding of the leaflets L. FIG. 12 also illustrates some of the leaflets being smashed together (smashed Leaflets-SL) which can result in damage to the leaflets L. Such undesirable smashing of the leaflets L is illustrated in FIG. 11.

Figure 13:
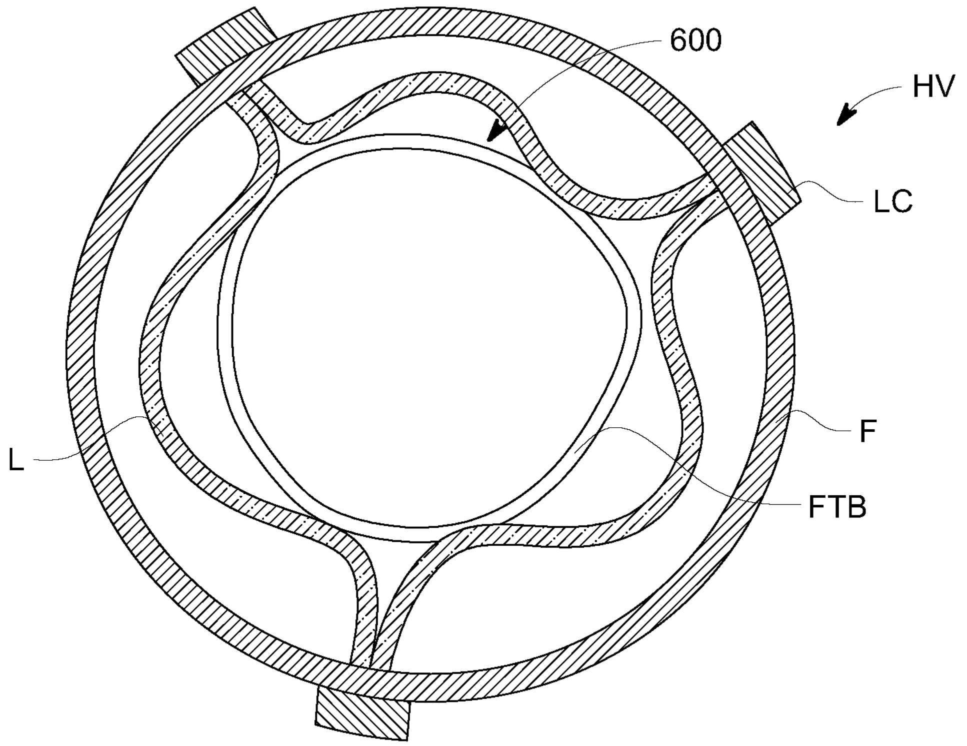
FIG. 13 illustrates a non-limiting radially collapsible insert that can be used in a crimping method for crimping a prosthetic heart valve to obtain a leaflet folding arrangement that is the same or similar to the leaflet folding arrangement of FIGS. 5, 6 and 11.
Figure 14:
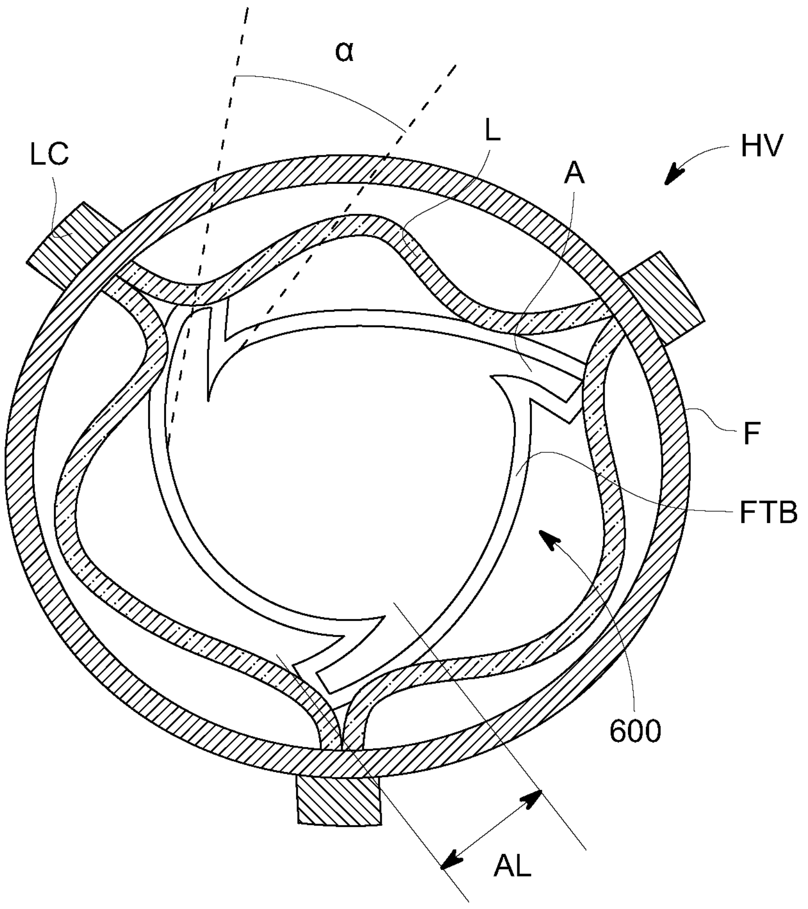
FIG. 14 illustrates another non-limiting radially collapsible insert that includes one or more arms that can be used in a crimping method for crimping a prosthetic heart valve to obtain a leaflet folding arrangement that is the same or similar to the leaflet folding arrangement of FIGS. 5, 6 and 11.

Referring now to FIGS. 13-14, there is illustrated a front-end view or inflow side end view of a prior art prosthetic heart valve showing the use of two different leaflet folding devices 600 in the form of collapsible folding tube bodies FTB in accordance with the present disclosure that are used to obtain the leaflet folding arrangement that is the same or similar to the one illustrated in FIGS. 5, 6, and 11. The prosthetic heart valve HV includes a crimpable frame F, a plurality of leaflets L that are connected to the frame at one or more leaflet connection regions LC. FIG. 13 illustrates a folding tube body FTB that has a generally hollow cylindrical tube shape. FIG. 14 illustrates the folding tube body FTB having a similar shape to the folding tube body of FIG. 13, but also including three radially extending collapsible arms A. The angle $\alpha$ at which each arm initially extends from the outer surface of the body of the radially collapsible insert is 5-175° (and all values and ranges therebetween). The length of the arms AL is generally 3-10 mm (and all values and ranges therebetween). The collapsible folding tube bodies FTB are configured to be partially or fully inserted in the interior of the prosthetic heart valve prior to the crimping of the prosthetic heart valve. Once the collapsible folding tube body FTB is inserted in the interior of the prosthetic heart valve, the prosthetic heart valve is partially crimped which results in the partial or full collapse of the radially collapsible insert. Thereafter, the collapsible folding tube body FTB is removed from the prosthetic heart valve and the prosthetic heart valve is then again subjected to crimping until the prosthetic heart valve is fully crimped.

The leaflet folding device can optionally be rotated and/or moved longitudinally along the longitudinal axis of the frame of prosthetic heart during the crimping of the prosthetic heart valve.

Figure 15:
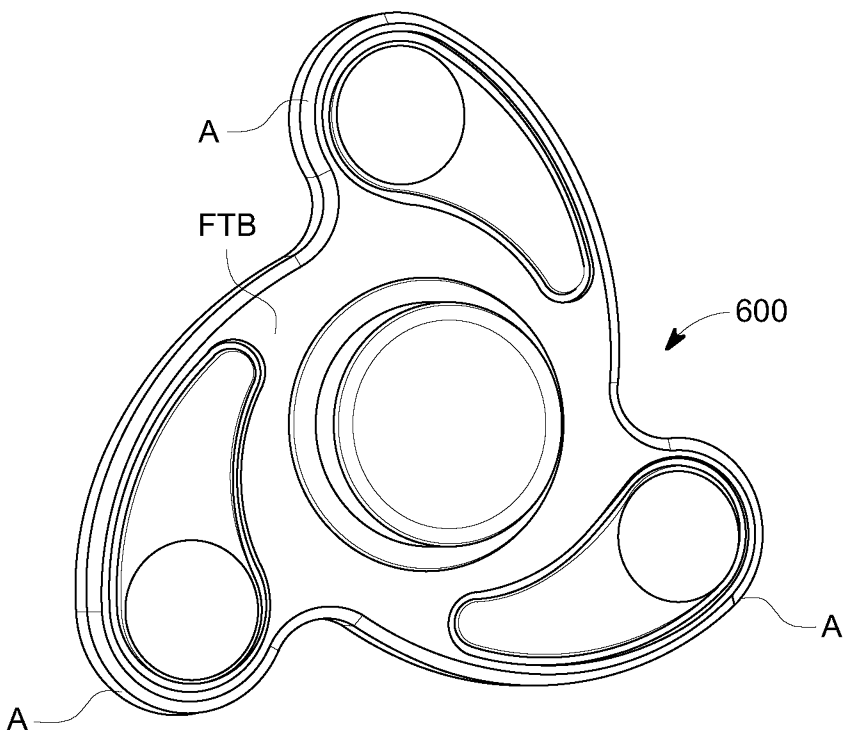
FIG. 15 illustrates a non-limiting forming shaft that includes one or more arms that can be used in a crimping method for crimping a prosthetic heart valve to obtain a leaflet folding arrangement that is the same or similar to the leaflet folding arrangement of FIGS. 5, 6 and 11.

Referring now to FIG. 15, there is illustrated a leaflet folding device 600 in the form of a forming shaft FTB that includes three arms A that operates in a similar manner as the leaflet folding devices discussed above with reference to FIGS. 13 and 14, except that the body of the forming shaft is not collapsible. The arms on the forming shaft are used to obtain the leaflet folding arrangement that is the same or similar to the one illustrated in FIGS. 5, 6 and 11. The forming shaft is partially or fully inserted in the interior of the prosthetic heart valve prior to the crimping of the prosthetic heart valve. Once the forming shaft is inserted in the interior of the prosthetic heart valve such that the arms of the forming shaft are at least partially positioned in the interior of the prosthetic heart valve, the prosthetic heart valve is partially crimped. Thereafter, the forming shaft is removed from the prosthetic heart valve and the prosthetic heart valve is then again subjected to crimping until the prosthetic heart valve is fully crimped. The leaflet folding device can optionally be rotated and/or moved longitudinally along the longitudinal axis of the frame of prosthetic heart during the crimping of the prosthetic heart valve.

Figure 16:
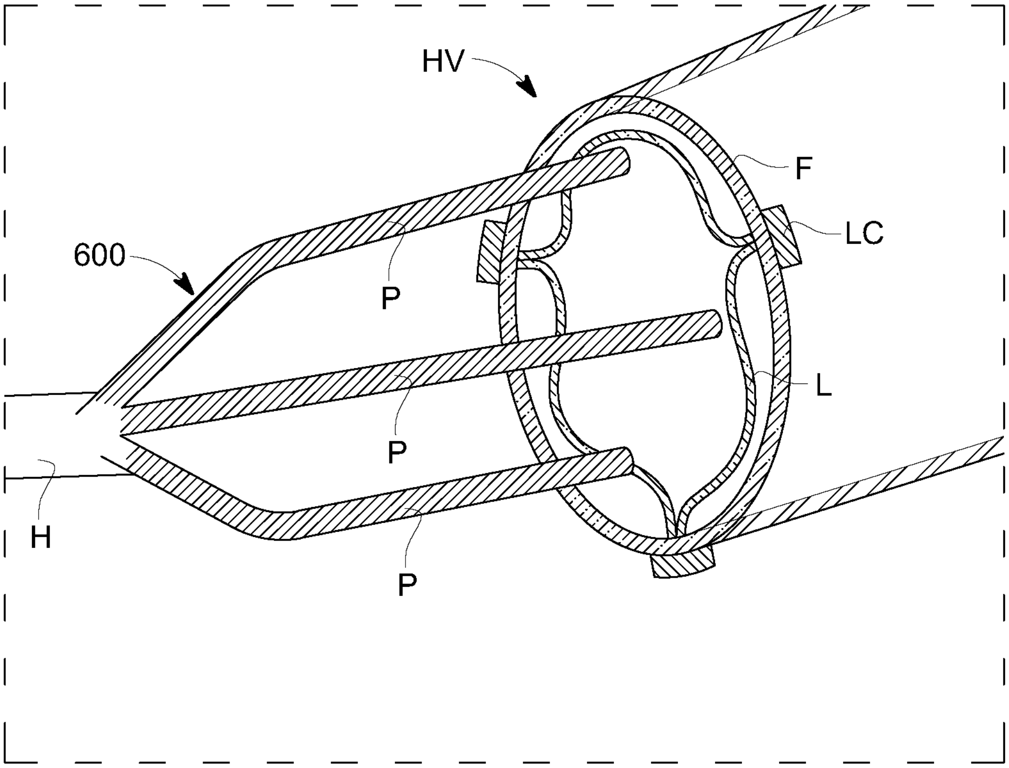
FIG. 16 illustrates a fold guide instrument that includes a plurality of prongs that can be used in a crimping method for crimping a prosthetic heart valve to obtain a leaflet folding arrangement that is the same or similar to the leaflet folding arrangement of FIGS. 5, 6 and 11; and, FIG. 17 is a table that illustrates the difference in the crimped outer diameter and the expanded outer diameter of the same prosthetic heart valve wherein one prosthetic heart valve was crimped by a traditional prior art crimping method and the other prosthetic heart valve was crimped by using one or more of the crimping methods in accordance with the present disclosure.

Referring now to FIG. 16, there is illustrated a front end or inflow side prospective view of a prosthetic heart valve HV showing the use of a leaflet folding device 600 in accordance with the present disclosure that is used to obtain the leaflet folding arrangement that is the same or similar to the one illustrated in FIGS. 5, 6 and 11. The leaflet folding device 600 includes a handle H and a plurality of prongs P that extend forwardly and radially outwardly from the central axis of the handle H. The prongs P are configured to be partially or fully inserted in the interior of the prosthetic heart valve prior to and/or during the crimping of the prosthetic heart valve HV. Once the prongs of the leaflet folding device 600 are inserted in the interior of the prosthetic heart valve, the prosthetic heart valve is partially crimped which results in the partial bending of the prongs. During the partial crimping of the prosthetic heart valve, the leaflet folding device 600 can be optionally rotated. Prior to the complete crimping of the prosthetic heart valve, the prongs of the leaflet folding device 600 are removed from the prosthetic heart valve and the prosthetic heart valve is then again subjected to crimping until the prosthetic heart valve is fully crimped.

Referring now to FIG. 17, a table is shown comparing the outer crimped diameter of a prosthetic heart valve without using the crimping methods in accordance with the present disclosure to the crimped diameter of a prosthetic heart valve that has used one or more of the crimping methods in accordance with the present disclosure. The second column illustrates that a prior art prosthetic heart valve that is crimped without using the crimping methods in accordance with the present disclosure has a maximum fully crimped outer diameter of 7.86 mm and a 64.4% reduction in diameter compared to the diameter of the prosthetic heart valve prior to being crimped. The second column also illustrates the same prior art prosthetic heart valve that is crimped using one or more of the crimping methods in accordance with the present disclosure has a maximum fully crimped outer diameter of 5.98 mm and a 73.8% reduction in diameter compared to the diameter of the prosthetic heart valve prior to being crimped. As such, by controlling the folding profile of the leaflets by using one or more of the crimping methods in accordance with the present disclosure, a significantly smaller final crimped outer diameter of the prosthetic heart valve can be obtained.

The first column of FIG. 17 also compares the outer expanded diameter of a prosthetic heart valve that has been expanded from its crimped state wherein the prosthetic heart valve was crimped by a traditional prior art crimping method to the outer expanded diameter of a prosthetic heart valve that has been expanded from its crimped state wherein the prosthetic heart valve was crimped by using one or more of the crimping methods in accordance with the present disclosure. The prosthetic heart valve crimped by a traditional prior art crimping method is shown to obtain a smaller maximum outer diameter when expanded as compared to a prosthetic heart valve crimped by using one or more of the crimping methods in accordance with the present disclosure. It is believed that this increased outer diameter is due in part to the uniform folding of the leaflets that results from using one or more of the crimping methods in accordance with the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall there between. The disclosure has been described with reference to the certain embodiments. These and other modifications of the disclosure will be obvious from the disclosure herein, whereby the foregoing descriptive matter is to be interpreted merely as illustrative of the disclosure and not as a limitation. It is intended to include all such modifications and alterations insofar as they come within the scope of the appended claims.

To aid the Patent Office and any readers of this application and any resulting patent in interpreting the claims appended hereto, Applicant does not intend any of the appended claims or claim elements to invoke 35 U.S.C. 112 (f) unless the words "means for" or "step for" are explicitly used in the particular claim.

What is claimed:

1. A method for reducing an outer diameter of a crimped prosthetic heart valve comprising:

providing said prosthetic heart valve that is in a non-fully crimped state; said prosthetic heart valve includes a frame and a leaflet structure that is at least partially supported by said frame;

said frame is in a non-fully crimped state;

providing a diameter reducing device that is configured to reduce an outer diameter of said prosthetic heart valve and an outer diameter of said frame by applying a crimping force to said prosthetic heart valve frame; said diameter reducing device includes a device opening; said device opening is configured to receive at least a portion of said frame; said device opening is configured to reduce in cross-sectional area during operation of said diameter reducing device;

at least partially inserting said prosthetic heart valve in said device opening of said diameter reducing device such that at least a portion of said frame is positioned in said device opening; and initially reducing an outer diameter of said frame of said prosthetic heart valve by use of said diameter reducing device by reducing said cross-sectional area of said device opening; and wherein said step of initially reducing includes applying a crimping force on said frame of the prosthetic heart valve along a longitudinal length of said prosthetic heart valve; and wherein said step of initially reducing further includes either A) gradual progressive application of said crimping force in a continuously progressive manner along a longitudinal length of said frame by i) initially applying said crimping force to said frame by causing reduction of said cross-sectional area of said device opening at an inflow end of said frame and then ii) subsequently applying said crimping force in a progressive manner along at least a portion of a longitudinal length of said frame at a different locations on said frame to cause said progressive reduction of said cross-sectional area of said device opening at locations that are spaced from said inflow end of said frame until said crimping force is applied to an outer surface of said frame along at least 50% of said longitudinal length of said frame; or B) stepwise application of said crimping force along a longitudinal length of said frame by i) initially applying said crimping force on said frame by causing reduction of said cross-sectional area of said device opening at an inflow region of said frame until a portion or all of said inflow region of said frame is crimped to 10-100% of a fully crimped diameter or cross-sectional area, ii) partially or fully removing said crimping force from said frame, and then iii) subsequently applying said crimping force by causing reduction of said cross-sectional area of said device opening at one or more locations that are spaced from said inflow region of said frame to crimped said one or more locations that are spaced from said inflow region of said frame to 10-100% of a fully crimped diameter or cross-sectional area, and wherein said inflow region of said frame extends from an inflow end of said frame to 5-75% of said longitudinal length of said frame, and wherein said outflow region of said frame extends from an outflow end of said frame to 5-75% of said longitudinal length of said frame.

2. The method as defined in claim 1, wherein said prosthetic heart valve is subjected to a further secondary crimping process after said step of initially reducing; said secondary crimping process includes one of a) simultaneously subjecting said prosthetic heart valve to said crimping force along 80-100% of said longitudinal length of said frame, b) applying said gradual application of said crimping force in a continuously progressive manner along 80-100% of said longitudinal length of said frame, or c) applying said stepwise application of said crimping force along 80-100% of said longitudinal length of said frame.

3. The method as defined in claim 1, further including the steps of:

providing a leaflet folding device that is configured to facilitate in folding of said leaflet structure during said step of initially reducing;

at least partially inserting said leaflet folding device inside at least a portion of said prosthetic heart valve prior to or during said step of initially reducing;

reducing a diameter or cross-sectional area of at least a portion of said frame while said leaflet folding device is at least partially inserted in said prosthetic heart valve; and removing said leaflet folding device from said prosthetic heart valve prior to completion of step of initially reducing.

4. The method as defined in claim 3, further including the step of a) moving said leaflet folding device along said longitudinal length of said frame during said step of initially reducing while said leaflet folding device is at least partially inserted in said prosthetic heart valve, and/or b) rotating said leaflet folding device in said frame during said step of initially reducing while said leaflet folding device is at least partially inserted in said prosthetic heart valve.

5. The method as defined in claim 3, wherein said leaflet folding device includes a radially collapsible insert portion.

6. The method as defined in claim 5, wherein said radially collapsible insert portion has a generally circular or oval cross-sectional shape along 25%-100% of a longitudinal length of said radially collapsible insert portion.

7. The method as defined in claim 5, wherein said radially collapsible insert portion has a generally constant cross-sectional area along 60-100% said longitudinal length of said radially collapsible insert portion.

8. The method as defined in claim 5, wherein said radially collapsible insert portion includes a hollow interior cavity along 25-100% of said longitudinal length of said radially collapsible insert portion.

9. The method as defined in claim 8, wherein said hollow interior cavity has a generally circular or oval cross-sectional shape.

10. The method as defined in claim 5, wherein said radially collapsible insert portion includes one or more arms that extend outwardly from an outer surface of said radially collapsible insert portion.

11. The method as defined in claim 10, wherein said one or more arms are collapsible and said radially collapsible insert portion includes an internal cavity.

12. The method as defined in claim 5, wherein at least a portion of said radially collapsible insert portion is configured to at least partially collapse and/or reduce in cross-sectional area during said step of initially reducing while said leaflet folding device is at least partially inserted in said prosthetic heart valve.

13. The method as defined in claim 3, wherein said leaflet folding device includes a forming shaft that is configured to maintain its cross-sectional shape and cross-sectional area during said step of initially reducing while said leaflet folding device is at least partially inserted in said prosthetic heart valve.

14. The method as defined in claim 13, wherein said forming shaft has a generally circular or oval cross-sectional shape along 25%-100% of a longitudinal length of said forming shaft.

15. The method as defined in claim 13, wherein said forming shaft has a generally constant cross-sectional size along 60-100% said longitudinal length of said forming shaft.

16. The method as defined in claim 13, wherein said forming shaft includes a hollow interior cavity along 25-100% of said longitudinal length of said forming shaft.

17. The method as defined in claim 13, wherein said forming shaft includes one or more arms that extend outwardly from an outer surface of said forming shaft.

18. The method as defined in claim 13, wherein said forming shaft including a plurality of prongs that extend both radially outward from said forming shaft and extend forwardly from an end of said forming shaft.

19. The method as defined in claim 18, wherein a number of prongs is equal to a number of leaflets in said leaflet structure in said prosthetic heart valve.

20. The method as defined in claim 3, further including the step of positioning at least a portion of said leaflet folding device between said one or more leaflets of said leaflet structure and frame of said prosthetic heart valve to facilitate in a) bending at least a portion of one or more of said leaflets toward a central longitudinal axis of said frame of said prosthetic heart valve during said step of initially reducing, and/or b) rotating at least a portion of one or more of said leaflets about said central longitudinal axis of said frame of said prosthetic heart valve during said step of initially reducing.

21. The method as defined in claim 20, wherein said leaflet folding device includes a handle portion and one or more leaflet engagement members that are attached to and extend from said handle portion; said one or more leaflet engagement members are at least partially formed of a flexible material that enables said one or more leaflet engagement members to flex and/or bend a) when positioning said one or more leaflet engagement members about one or more of said leaflets, and/or b) as said frame of said prosthetic heart valve reduces in diameter or cross-sectional area as said crimping force is applied on said frame of said prosthetic heart valve.

22. The method as defined in claim 21, wherein said one or more leaflet engagement members include a wire loop.

23. The method as defined in claim 20, further including the step of positioning a portion or one or more of said leaflet engagement members between a portion of one or more of said leaflets and said frame of said prosthetic heart valve to cause at least a portion of said one or more of said leaflets to bend towards said central longitudinal axis of said frame of said prosthetic heart valve.

24. A method for reducing the profile of a frame of a medical device; said method comprising:

providing said medical device that includes said frame that has a crimpable or plastically deformable portion;

providing a crimping device; said crimping device includes a crimping assembly that has a device opening; said device opening is configured to receive at least a portion of said frame of said medical device; said device opening is configured to reduce in diameter or cross-sectional area during operation of said crimping device;

inserting at least a portion of said crimpable or plastically deformable portion of said frame of said medical device into said device opening; and operating said crimping device to cause at least a portion of said device opening to reduce in diameter or cross-sectional area to thereby exert a crimping force initially on only a first portion of said crimpable or plastically deformable portion of said frame of said medical device which causes said first portion of said crimpable or plastically deformable portion of said frame of said medical device to reduce in cross-sectional area, and thereafter continuing to use said crimping device to subsequently exert a crimping force on a second portion of said crimpable or plastically deformable portion of said frame of said medical device which causes said second portion of said crimpable or plastically deformable portion of said frame of said medical device to reduce in cross-sectional area; said first portion of said crimpable or plastically deformable portion of said frame of said medical device constitutes 0.01%-75% of a longitudinal length of said crimpable or plastically deformable portion of said frame of said medical device.

25. The method as defined in claim 24, wherein said crimping device is configured to continue to exert said crimping force on both said first and second portions of said crimpable or plastically deformable portion of said frame of said medical device after initially exerting said crimping force on said second portion so as to further reduce said diameter or cross-sectional area of both said first and second portions of said crimpable or plastically deformable portion of said frame of said medical device.

26. The method as defined in claim 25, wherein said crimping device is configured to exert said crimping force on said first portion of said crimpable or plastically deformable portion of said frame of said medical device until said diameter or cross- sectional area of said first portion of said crimpable or plastically deformable portion of said frame of said medical device is reduced by at least 1% prior to said crimping device initially exerting said crimping force on said second portion of said crimpable or plastically deformable portion of said frame of said medical device.

27. The method as defined in claim 25, wherein said crimping device is configured to exert said crimping force on said first portion of said crimpable or plastically deformable portion of said frame of said medical device until said diameter or cross-sectional area of said first portion of said crimpable or plastically deformable portion of said frame of said medical device is reduced by at least 5% prior to said crimping device initially exerting said crimping force on said second portion of said crimpable or plastically deformable portion of said frame of said medical device.

28. The method as defined in claim 25, wherein said crimping device is configured to exert said crimping force on said first portion of said crimpable or plastically deformable portion of said frame of said medical device until said diameter or cross-sectional area of said first portion of said crimpable or plastically deformable portion of said frame of said medical device is reduced by at least 25% prior to said crimping device initially exerting said crimping force on said second portion of said crimpable or plastically deformable portion of said frame of said medical device.

29. The method as defined in claim 25, wherein said crimping device is configured to exert said crimping force on said first portion of said crimpable or plastically deformable portion of said frame of said medical device until said diameter or cross-sectional area of said first portion of said crimpable or plastically deformable portion of said frame of said medical device is reduced by at least 50% prior to said crimping device initially exerting said crimping force on said second portion of said crimpable or plastically deformable portion of said frame of said medical device.

30. The method as defined in claim 24, wherein said first and second portions of said crimpable or plastically deformable portion of said frame of said medical device are both simultaneously positioned in said device opening during reduction of said diameter or cross-sectional area of said first and second portions of said crimpable or plastically deformable portion of said frame of said medical device by said crimper device.

31. The method as defined in claim 24, wherein said first portion of said crimpable or plastically deformable portion of said frame of said medical device includes an inflow end portion of said medical device.

32. The method as defined in claim 24, wherein said second portion of said crimpable or plastically deformable portion of said frame of said medical device includes an outflow end portion of said medical device.

33. The method as defined in claim 24, wherein said medical device includes one or more leaflets that are connected to said crimpable or plastically deformable portion of said frame of said medical device.

34. The method as defined in claim 33, wherein said medical device is a prosthetic heart valve.

35. The method as defined in claim 33, further including the step of causing at least a portion of one or more of said leaflets to be bent toward a central longitudinal axis of said frame of said medical device a) prior to applying said crimping force on said crimpable or plastically deformable portion of said frame of said medical device, and/or b) while applying said crimping force to said crimping of said crimpable or plastically deformable portion of said frame of said medical device.

36. The method as defined in claim 33, further includes the step of applying a rotational force about a central longitudinal axis of said frame to one or more of said leaflets a) prior to applying said crimping force on said crimpable or plastically deformable portion of said frame of said medical device, and/or b) while applying said crimping force to said crimping of said crimpable or plastically deformable portion of said frame of said medical device.

37. The method as defined in claim 33, further providing a leaflet folding device that is configured to facilitate in folding said one or more of said leaflet during said step of applying said crimping force on said crimpable or plastically deformable portion of said frame of said medical device.

38. The method as defined in claim 37, further including the steps of:

at least partially inserting said leaflet folding device inside at least a portion of said crimpable or plastically deformable portion of said frame of said medical device prior to fully crimping said crimpable or plastically deformable portion of said frame of said medical device;

applying said crimping force to said crimpable or plastically deformable portion of said frame of said medical device while said leaflet folding device is at least partially inserted in said crimpable or plastically deformable portion of said frame of said medical device;

removing said leaflet folding device from said crimpable or plastically deformable portion of said frame of said medical device prior to said crimpable or plastically deformable portion of said frame of said medical device being fully crimped; and further subjecting said said crimpable or plastically deformable portion of said frame of said medical device to said crimping force after said step of removing said leaflet folding device.

39. The method as defined in claim 37, further including the step of a) moving said leaflet folding device along said longitudinal length of said crimpable or plastically deformable portion of said frame of said medical device during said step of applying said crimping force to said crimpable or plastically deformable portion of said frame of said medical device while said leaflet folding device is at least partially inserted in said crimpable or plastically deformable portion of said frame of said medical device, and/or b) rotating said leaflet folding device in said crimpable or plastically deformable portion of said frame of said medical device during said step of applying said crimping force to said crimpable or plastically deformable portion of said frame of said medical device while said leaflet folding device is at least partially inserted in said crimpable or plastically deformable portion of said frame of said medical device.

40. The method as defined in claim 37, further including the step of positioning at least a portion of said leaflet folding device between said one or more leaflets and said crimpable or plastically deformable portion of said frame of said medical device to facilitate in a) bending at least a portion of one or more of said leaflets toward said central longitudinal axis of said crimpable or plastically deformable portion of said frame of said medical device, and/or b) rotating at least a portion of one or more of said leaflets about said central longitudinal axis of said crimpable or plastically deformable portion of said frame of said medical device.

41. The method as defined in claim 37, further includes the step of fully disengaging said leaflet folding device from one or more of said leaflets prior to completion of applying said crimping force on said crimpable or plastically deformable portion of said frame of said medical device.

42. The method as defined in claim 37, wherein said leaflet folding device includes a handle portion and one or more leaflet engagement members that are attached to and extend from said handle portion; said one or more leaflet engagement members are at least partially formed of a flexible material that enables said one or more leaflet engagement members to flex and/or bend a) when positioning said one or more leaflet engagement members about one or more leaflets, and/or b) as said crimpable or plastically deformable portion of said frame of said medical device reduces in diameter or cross-sectional area as said crimping force is applied on said crimpable or plastically deformable portion of said frame of said medical device.

43. The method as defined in claim 42, wherein said one or more leaflet engagement members include a wire loop.

44. The method as defined in claim 42, further including the step of positioning a portion or one or more of said leaflet engagement members between a portion of one or more of said leaflets and said crimpable or plastically deformable portion of said frame of said medical device to cause at least a portion of said one or more of said leaflets to bend towards said central longitudinal axis of said crimpable or plastically deformable portion of said frame of said medical device.

45. The method as defined in claim 37, wherein said leaflet folding device includes a radially collapsible insert portion.

46. The method as defined in claim 45, wherein said radially collapsible insert portion has a generally circular or oval cross-sectional shape along 25%-100% of a longitudinal length of said radially collapsible insert portion.

47. The method as defined in claim 45, wherein said radially collapsible insert portion has a generally constant cross-sectional size along 60-100% said longitudinal length of said radially collapsible insert portion.

48. The method as defined in claim 45, wherein said radially collapsible insert portion includes a hollow interior cavity along 25-100% of said longitudinal length of said radially collapsible insert portion.

49. The method as defined in claim 48, wherein said hollow interior cavity has a generally circular or oval cross-sectional shape.

50. The method as defined in claim 45, wherein said radially collapsible insert portion includes one or more arms that extend outwardly from an outer surface of said radially collapsible insert portion.

51. The method as defined in claim 50, wherein said one or more arms are collapsible and said radially collapsible insert portion includes an internal cavity.

52. The method as defined in claim 45, wherein at least a portion of said radially collapsible insert portion at least partially collapses and/or reduces in cross- sectional area during said step of applying said crimping force to said crimpable or plastically deformable portion of said frame of said medical device while said leaflet folding device is at least partially inserted in said crimpable or plastically deformable portion of said frame of said medical device.

53. The method as defined in claim 37, wherein said leaflet folding device includes a forming shaft that is configured to maintain its cross-sectional shape and cross-sectional area during said step of applying said crimping force to said crimpable or plastically deformable portion of said frame of said medical device while said leaflet folding device is at least partially inserted in said crimpable or plastically deformable portion of said frame of said medical device.

54. The method as defined in claim 53, wherein said forming shaft has a generally circular or oval cross-sectional shape along 25%-100% of a longitudinal length of said forming shaft.

55. The method as defined in claim 53, wherein said forming shaft has a generally constant cross-sectional size along 60-100% said longitudinal length of said forming shaft.

56. The method as defined in claim 53, wherein said forming shaft includes a hollow interior cavity along 25-100% of said longitudinal length of said forming shaft.

57. The method as defined in claim 53, wherein said forming shaft includes one or more arms that extend outwardly from an outer surface of said forming shaft.

58. The method as defined in claim 53, wherein said forming shaft including a plurality of prongs that extend both radially outward from said forming shaft and extend forwardly from an end of said forming shaft.

59. The method as defined in claim 58, wherein a number of prongs is equal to a number of said leaflets in said medical device.

* * * * *